(12) United States Patent
Goel et al.

(10) Patent No.: US 10,570,398 B2
(45) Date of Patent: Feb. 25, 2020

(54) METHODS AND COMPOSITIONS INVOLVING TRANSMEMBRANE AND COILED-COIL DOMAINS 3 (TM-CO3) IN CANCER

(71) Applicant: BAYLOR RESEARCH INSTITUTE, Dallas, TX (US)

(72) Inventors: Ajay Goel, Dallas, TX (US); Kunitoshi Shigeyasu, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 37 days.

(21) Appl. No.: 15/559,362

(22) PCT Filed: Mar. 17, 2016

(86) PCT No.: PCT/US2016/022757
§ 371 (c)(1),
(2) Date: Sep. 18, 2017

(87) PCT Pub. No.: WO2016/149445
PCT Pub. Date: Sep. 22, 2016

(65) Prior Publication Data
US 2018/0298386 A1 Oct. 18, 2018

Related U.S. Application Data

(60) Provisional application No. 62/135,028, filed on Mar. 18, 2015.

(51) Int. Cl.
| | | |
|---|---|---|
| *A61K 48/00* | (2006.01) | |
| *C07H 21/02* | (2006.01) | |
| *C07H 21/04* | (2006.01) | |
| *C12N 15/113* | (2010.01) | |
| *C12Q 1/6886* | (2018.01) | |
| *G01N 33/574* | (2006.01) | |
| *A61P 35/04* | (2006.01) | |
| *A61P 35/00* | (2006.01) | |
| *C07K 16/28* | (2006.01) | |
| *C07K 16/32* | (2006.01) | |

(52) U.S. Cl.
CPC ......... *C12N 15/1138* (2013.01); *A61P 35/00* (2018.01); *A61P 35/04* (2018.01); *C07K 16/28* (2013.01); *C07K 16/32* (2013.01); *C12N 15/1135* (2013.01); *C12Q 1/6886* (2013.01); *G01N 33/57419* (2013.01); *C12N 2310/11* (2013.01); *C12N 2310/14* (2013.01); *C12N 2310/531* (2013.01); *C12Q 2600/158* (2013.01)

(58) Field of Classification Search
CPC ........................... A61K 31/713; C12N 15/113
See application file for complete search history.

(56) References Cited

U.S. PATENT DOCUMENTS

| | | | | |
|---|---|---|---|---|
| 8,318,925 B2 * | 11/2012 | Tang | .................. | A61K 31/7052 435/320.1 |
| 2012/0082659 A1 | 4/2012 | Land et al. | ................ | 424/133.1 |
| 2014/0363372 A1 | 12/2014 | Yu et al. | ...................... | 424/1.49 |

OTHER PUBLICATIONS

Chokshi et al. (Indian J. Surg. Dec. 2009; 71 (6): 350-5).*
International Search Report Issued in Corresponding PCT Application No. PCT/US2016/022757, dated Jun. 27, 2016.
Partial Search Report Issued in Corresponding European Application No. 16765711, dated Nov. 22, 2018.
Shigeyasu, et al., "TMCO3—A Novel Na+/H+ Transporter Protein with a Promising Potential as a Prognostic Biomarker in Colorectal Cancer," *Gastroenterology*, 148(4), Suppl. 1; S353, 2015.
Wang & Yu, et al., "Abstract 3317: The Roles of TMCC3 in Breast Cancer Cells," *Cancer Research*, 72, No. 8 Suppl., 3317-3317, 2012.
Chanroj et al., "Conserved and diversified gene families of monovalent cation/h(+) antiporters from algae to flowering plants," *Frontiers in Plant Science*, 2012, 3:25.
Harguindey et al., "Proton transport inhibitors as potentially selective anticancer drugs." *Anticancer Research*, 2009, 29:2127-36.
Kaiser et al., "Transcriptional recapitulation and subversion of embryonic colon development by mouse colon tumor models and human colon cancer" *Genome Biology*, 2007, 8:R131.
Skrzypczak et la., "Modeling oncogenic signaling in colon tumors by multidirectional analyses of microarray data directed for maximization of analytical reliability" *PloS one*, 2010, 5(10):e13091.
Xie et al., "Molecular Mechanisms Underlying the Cholesterol-lowering Effect of Ginkgo biloba Extract in Hepatocytes: a Comparative Study with Lovastatin." *Acta Pharmacologica Sinica*, 2009, 30:1262-1275.

* cited by examiner

*Primary Examiner* — Amy H Bowman
(74) *Attorney, Agent, or Firm* — Norton Rose Fulbright US LLP

(57) ABSTRACT

Certain embodiments provide methods and compositions related to clinical management of cancer patients based on the expression level of TMCO3. Further embodiments involve methods and compositions related to treatment of cancer patients or patients determined to have an increased TMCO3 level relative to a control or a reference level that is normal or indicating favorable prognosis.

19 Claims, 24 Drawing Sheets
Specification includes a Sequence Listing.

c
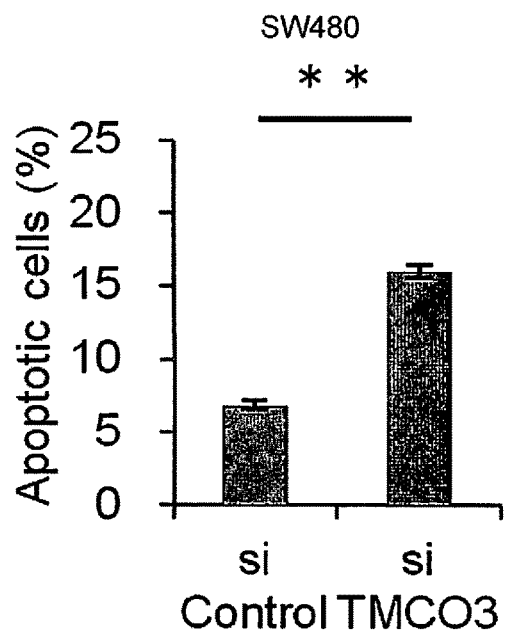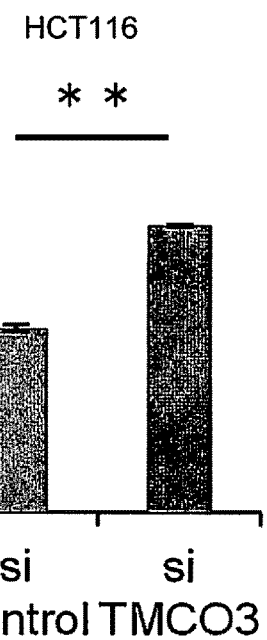
d
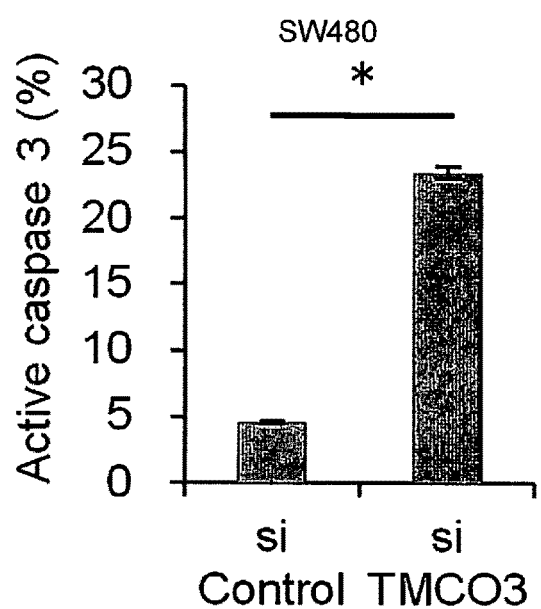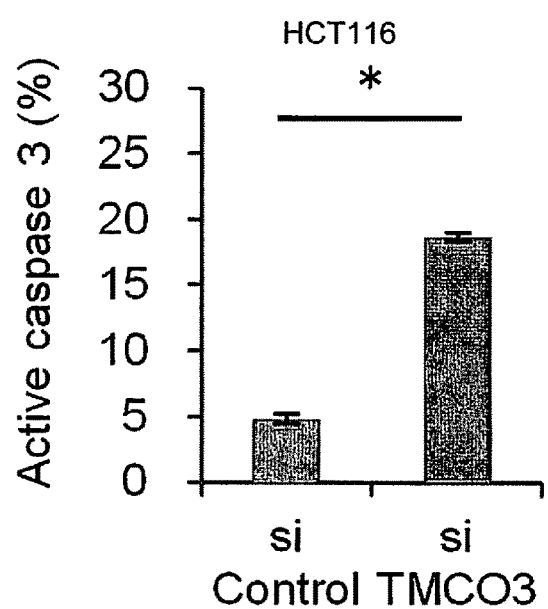
FIG. 10C - 10D a
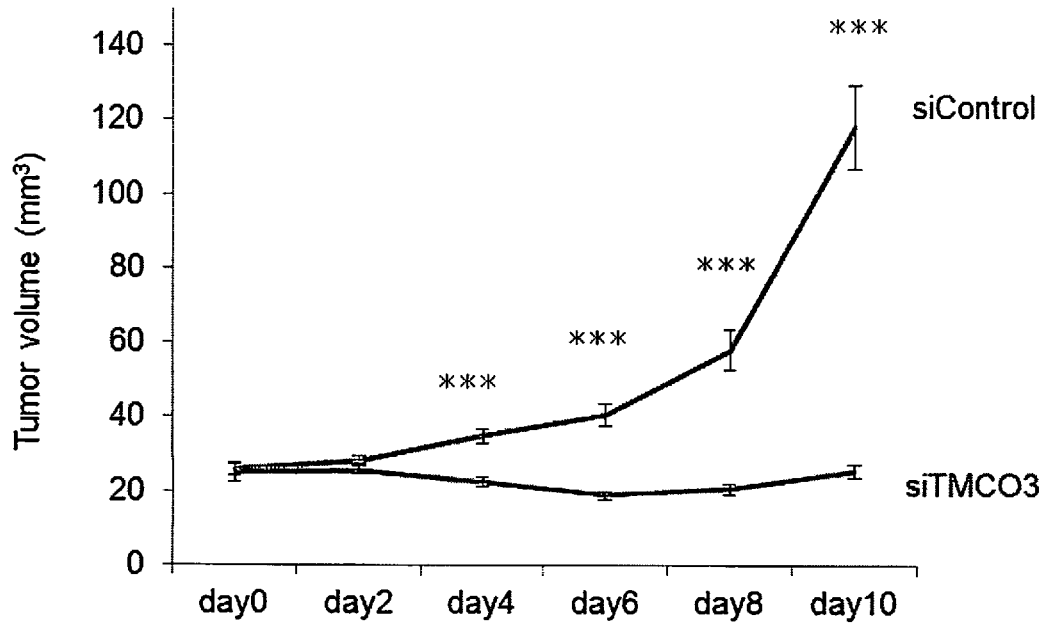
b
c
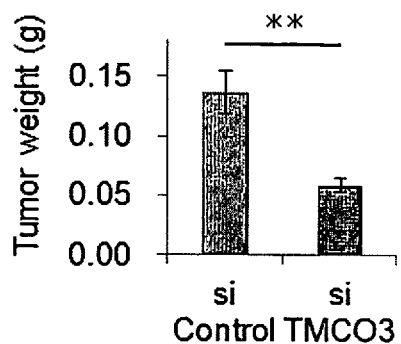
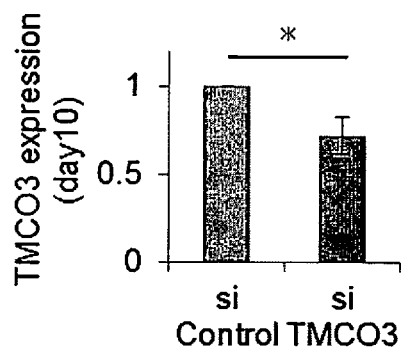
FIG. 11A - 11C a b a b

METHODS AND COMPOSITIONS INVOLVING TRANSMEMBRANE AND COILED-COIL DOMAINS 3 (TM-CO3) IN CANCER

CROSS-REFERENCE TO RELATED APPLICATIONS

This application is a national phase under 35 U.S.C. § 371 of International Application No. PCT/US2016/022757, filed Mar. 17, 2016, which claims the benefit of priority to U.S. Provisional Patent Application No. 62/135,028, filed Mar. 18, 2015, the entire contents of each of which are hereby incorporated by reference in their entirety.

This invention was made with government support under Grant Nos. R01 CA72851 and 181572 from the National Cancer Institute, National Institutes of Health. The government has certain rights in the invention.

BACKGROUND OF THE INVENTION

1. Field of the Invention

The present invention relates generally to the field of molecular biology and oncology. More particularly, it concerns methods and compositions involving TMCO3 and cancer prognosis and treatment.

2. Description of Related Art

Colorectal cancer (CRC) is one of the most common malignancies worldwide, and is a major cause of cancer-related deaths (Siegel 2012). Survival rates of patients with CRC have increased in the past few years, possibly as a result of earlier diagnosis and improved treatment regimens, nonetheless, approximately 30-50% of patients who undergo curative resection subsequently experience local tumor recurrence or metastasis (Lieberman 2012). This subgroup of patients usually receive chemotherapy often in combination with monoclonal antibody therapy, with a median overall survival duration of ~20 months, and the response rates at best around 50% (Halama 2008). However, the substantial financial costs associated with CRC treatment not only present an economic burden, but also treatment of all patients with chemotherapy without a priori selection leads to overtreatment of patients with toxic agents that produce severe adverse effects (Meropol 2007).

In order to overcome this clinical challenge, there is a clear need to identify biomarkers that will facilitate the identification of patients with a poor prognosis, and permit personalized treatment strategies for such patients.

SUMMARY OF THE INVENTION

Certain embodiments provide predictive, prognostic and/or diagnostics methods for clinical management and treatment of subjects have elevated TMCO3 levels as compared to a control or reference level, or cancer patients, particularly colorectal cancer patients or patients at risk or determined to have colorectal cancer. Methods and compositions are based, in part, on the discovery that expression of TMCO3 in cancer patients is associated with poor prognosis, and can, therefore, provide basis for designing treatment strategies; and also the discovery that inhibition of TMCO3 in cancer patients has therapeutic significance.

In some embodiments, the subjects have an elevated level of a downstream target of TMCO3. In some embodiments, the downstream target is TFDP1.

Thus, methods of treating a cancer are provided, such as a colorectal cancer, gastric cancer, lung cancer, or melanoma, in a patient that comprise administering to the patient a pharmaceutical composition comprising an effective amount of an inhibitor of transmembrane and coiled-coil domains 3 (TMCO3) or a downstream target thereof and a pharmaceutical acceptable carrier. In further embodiments, the patient to be treated may be determined to have a higher expression level of TMCO3 as compared to a control or reference level that is normal or indicating favorable prognosis prior to or during the treatment.

In certain embodiments, the inhibitor is an isolated nucleic acid molecule that hybridizes with a nucleic acid molecule encoding TMCO3 (or a downstream target thereof), such as an siRNA, a double stranded RNA, a short hairpin RNA, or an antisense oligonucleotide.

In further embodiments, the inhibitor is an antibody that binds to a TMCO3 protein (or a downstream target thereof) and inhibits the activity of TMCO3 (or a downstream target thereof). In still further embodiments, the inhibitor is a small molecule compound, such as the TMCO3 inhibitor identified from pyrazine derivatives like amiloride, EIPA, HMA, DMA; benzoylgunidines like HOE-694, cariporide, eniporide, zoniporide, SM20550, BMC-284640, T-162559 (S), T-162559 (R), TY-12533, SL-591227, S03226, T-162559S, KB-R9032; phenoxazine derivatives like Phx-1, Phx-3; or Harmaline, Cimetidine, Clonidine, or any combinations or derivatives therefrom. In particular embodiments, the TMCO3 inhibitor is determined to inhibit TMCO3 function or activity. In some embodiments, the inhibitor inhibits TMCO3's activity of modulation of pH homeostasiss The chemical structures and descriptions of the candidate TMCO3 inhibitors can be any inhibitors of one or more Na+/H+ exchanger isoforms, for example, as described in Reshkin 2013 or Masereel 2003.

Lipids may be used to facilitate the delivery of pharmaceutical compositions. For example, the pharmaceutical composition further comprises cholesterol, polyethyleneglycol (PEG), 1,2-dioleoyl-sn-glycero-3-phosphatidylcholine (DOPC), egg phosphatidylcholine ("EPC"), dilauryloyl-phosphatidylcholine ("DLPC"), dimyristoylphosphatidylcholine ("DMPC"), dipalmitoylphosphatidylcholine ("DPPC"), di stearoylphosphatidylcholine ("DSPC"), 1-myristoyl-2-palmitoyl phosphatidylcholine ("WPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), lysophosphatidylcholine, dilinoleoylphosphatidylcholine distearoylphophatidylethanolamine ("DSPE"), dimyristoyl phosphatidylethanolamine ("DMPE"), dipalmitoyl phosphatidylethanolamine ("DPPE"), palmitoyloeoyl phosphatidylethanolamine ("POPE"), lysophosphatidylethanolamine, phosphatidylserine, phosphatidylglycerol, dimyristoyl phosphatidylserine ("DMPS"), dipalmitoyl phosphatidylserine ("DPPS"), brain phosphatidylserine ("BPS"), dilauryloylphosphatidylglycerol ("DLPG"), dimyristoylphosphatidylglycerol ("DWG"), dipalmitoylphosphatidylglycerol ("DPPG"), di stearoylphosphatidylglycerol ("DSPG"), dioleoylphosphatidylglycerol ("DOPG"), or any combination, or a liposome thereof.

In further embodiments, the pharmaceutical composition is administered intravenously, intramuscularly, intraperitoneally, intracerobrospinally, subcutaneously, intra-articularly, intrasynovially, intrathecally, orally, topically, through inhalation, or through a combination of two or more routes of administration.

There may be further provided a method for classifying or prognosing a patient, such as a colorectal cancer patient, comprising: measuring the level of expression of TMCO3 in a colorectal cancer sample of the patient; and classifying the patient as having a favorable prognosis based on a lower expression of TMCO3 in the sample as compared to a control or reference level that is normal or indicating favorable prognosis, or classifying the patient as having a poor prognosis based on a higher expression level as compared to the control or a reference level.

In certain embodiments, the methods may comprise obtaining a sample. Non-limiting examples of the sample include a tissue sample, a whole blood sample, a urine sample, a saliva sample, a serum sample or a fecal sample. In particular embodiments, the sample is a rectum sample, a colon sample, a cecum sample, or more particularly, a colorectal cancer sample.

The methods of obtaining a sample provided herein may include methods of obtaining a biopsy such as fine needle aspiration, core needle biopsy, vacuum assisted biopsy, incisional biopsy, excisional biopsy, punch biopsy, shave biopsy or skin biopsy. In certain embodiments, the sample is obtained from a biopsy from rectal, cecum, or colon tissue by any of the biopsy methods previously mentioned. In other embodiments, the sample may be obtained from any of the tissues provided herein that include but, are not limited to, gall bladder, skin, heart, lung, breast, pancreas, liver, muscle, kidney, smooth muscle, bladder, intestine, brain, prostate, esophagus, or thyroid tissue.

Alternatively, the sample may include, but is not be limited to, blood, serum, sweat, hair follicle, buccal tissue, tears, menses, urine, feces, or saliva. In particular embodiments, the sample may be a tissue sample, a whole blood sample, a urine sample, a saliva sample, a serum sample, a plasma sample or a fecal sample. In particular embodiments, the sample may be a bodily fluid sample, including, but not limited to, a whole blood sample, a urine sample, a saliva sample, a tear sample, a serum sample, or a plasma sample. In further embodiments, the sample may be a sample that has been enriched for certain exosomes.

Some embodiments further involve isolating nucleic acids such as ribonucleic or RNA from a biological sample or in a sample of the patient. In certain aspects, isolating nucleic acids may not be needed or may be avoided. Other steps may or may not include amplifying a nucleic acid in a sample and/or hybridizing one or more probes to an amplified or non-amplified nucleic acid.

The methods may further comprise assaying nucleic acids in a sample. In certain embodiments, a microarray or any methods known in the art may be used to measure or assay the level of TMCO3 expression in a sample. The nucleic acid assay methods may further include, but not be limited to, PCR, digital PCR, dd PCR (digital droplet PCR), nCounter (nanoString), BEAMing (Beads, Emulsions, Amplifications, and Magnetics) (Inostics), ARMS (Amplification Refractory Mutation Systems), RNA-Seq, TAm-Seg (Tagged-Amplicon deep sequencing), PAP (Pyrophosphorolysis-activation polymerization), RT-PCR, in situ hybridization, northern hybridization, hybridization protection assay (HPA)(GenProbe), branched DNA (bDNA) assay (Chiron), rolling circle amplification (RCA), single molecule hybridization detection (US Genomics), Invader assay (ThirdWave Technologies), and/or Bridge Litigation Assay (Genaco), next generation RNA sequencing, or a combination thereof. The methods may further comprise recording the TMCO3 expression level in a tangible medium or reporting the expression level to the patient, a health care payer, a physician, an insurance agent, or an electronic system.

In further embodiments, measuring the level of TMCO3 expression may comprise measuring protein expression in the sample. For example, measuring protein expression may comprise performing ELISA, RIA, FACS, dot blot, Western Blot, immunohistochemistry, antibody-based radioimaging, mass spectroscopy, or a combination thereof.

Certain aspects of the methods are provided for patients that are stage I, II, III or IV colorectal cancer patients or any combinations thereof.

In certain embodiments, methods described herein may further comprise monitoring the patient for colorectal cancer under intensive surveillance after the patient has been classified as having a poor prognosis. In other embodiments, methods may comprise monitoring the patient for colorectal cancer under regular surveillance after the patient has been classified as having a favorable prognosis.

In additional embodiments, methods may comprise treating the patient for colorectal cancer with a pharmaceutical composting comprising a TMCO3 inhibitor (or downstream target thereof) after the patient has been classified as having a poor prognosis; or, alternatively, treating the patient for colorectal cancer under regular surveillance if the patient is classified as having a favorable prognosis.

The methods may further comprise recording the TMCO3 expression level (or downstream target thereof) in a tangible, computer-readable medium or a tangible data storage device, or reporting the expression level to the patient, a health care payer, a physician, an insurance agent, an electronic system, or a tangible data storage device.

Further aspects relate to a method for treating a patient for early or advanced colorectal cancer comprising: treating the patient for advanced colorectal cancer after the patient is determined to have an elevated level of TMCO3 expression in a biological sample from the patient compared to a biological sample from a patient with early colorectal cancer; or treating the patient for early colorectal cancer after the patient is determined to have a TMCO3 level of expression that is lower than or not significantly different than a level of TMCO3 expression in a biological sample from a patient with early colorectal cancer.

In some embodiments, early colorectal cancer comprises category T1 or T2 colorectal cancer. In some embodiments, early colorectal cancer comprises category T1 colorectal cancer. In some embodiments, early colorectal cancer excludes category T2 colorectal cancer. In some embodiments, advanced colorectal cancer excludes category T1 or T2 colorectal cancer. In some embodiments, advanced colorectal cancer excludes category T1 colorectal cancer. In some embodiments, early colorectal cancer comprises category N0 colorectal cancer. In some embodiments, advanced colorectal cancer excludes category N0 colorectal cancer. In some embodiments, early colorectal cancer comprises category M0 colorectal cancer. In some embodiments, advanced colorectal cancer excludes category M0 colorectal cancer.

In some embodiments, the treatment for early colorectal cancer comprises surgical incision of the primary tumor. In some embodiments, the treatment for early colorectal cancer excludes surgical incision of the primary tumor. In some embodiments, the treatment for early colorectal cancer excludes chemotherapy. In some embodiments, the treatment for early colorectal cancer comprises chemotherapy. In some embodiments, the treatment for the advanced colorectal cancer comprises surgical removal of one or more secondary tumors. In some embodiments, the treatment for the early colorectal cancer excludes surgical removal of one or more secondary tumors.

Further aspects relate to a biomarker for colorectal cancer cells, wherein the biomarker is an elevated level of expression or activity of TMCO3. In some embodiments, the elevated level of expression or activity of TMCO3 indicates that the cells are colorectal cancer cells. In some embodiments, a high elevated level of expression or activity of TMCO3 is a biomarker for advanced colorectal cancer and a low elevated level of expression or activity of TMCO3 is a biomarker for early colorectal cancer. In some embodiments, a low elevated level corresponds to a level of expression or activity in a sample from a patient with early colorectal cancer.

Yet further aspects relate to a method for diagnosing a patient with advanced or early colorectal cancer comprising: diagnosing the patient as having or likely to have advanced colorectal cancer or providing an analysis or report that the patient has or likely has advanced colorectal cancer when the expression or activity level of TMCO3 in a biological sample from the patient is determined to be elevated compared to the expression or activity level of TMCO3 in a biological sample from a patient with early colorectal cancer; and diagnosing the patient as having or likely to have early colorectal cancer or providing an analysis or report that the patient has or likely has early colorectal cancer when the expression or activity level of TMCO3 in the biological sample from the patient is determined to be not significantly different or lower than the expression or activity level of TMCO3 in a biological sample from a patient with early colorectal cancer.

In some embodiments, the method further comprises comparing the expression or activity level of TMCO3 (or downstream target thereof) in the biological sample from the patient to a control level of expression. In some embodiments, the biological sample from the patient is a sample from a primary colorectal cancer tumor. In some embodiments, the method further comprises treating the patient for early or advanced colorectal cancer.

Further method aspects relate to a method for determining whether a biological sample comprises colorectal cancer cells comprising: measuring the expression or activity level of TMCO3 (or downstream target thereof) in the biological sample; comparing the expression or activity level of TMCO3 (or downstream target thereof) in the biological sample to the expression or activity level of TMCO3 (or downstream target thereof) in a non-cancerous biological sample; determining that the biological sample comprises colorectal cancer cells when the expression or activity level of TMCO3 (or downstream target thereof) in the biological sample is higher than the expression or activity level of TMCO3 (or downstream target thereof) in the non-cancerous biological sample; and determining that the biological sample is non-cancerous when the expression or activity level of TMCO3 (or downstream target thereof) in the biological sample is not significantly different than the expression or activity level of TMCO3 (or downstream target thereof) in the non-cancerous biological sample. In some embodiments, the biological sample is tissue adjacent to a surgical site of a colorectal cancer patient. In some embodiments, the biological sample is comprises lymph node tissue.

In some embodiments, the method further comprises measuring the expression or activity level of TMCO3 (or downstream target thereof) in a biological sample from the patient. In some embodiments, the expression or activity level of TMCO3 (or downstream target thereof) is determined by a method described herein. In some embodiments, the mRNA expression level of TMCO3 (or downstream target thereof) is or was determined in the patient. In some embodiments, the protein expression level of TMCO3 (or downstream target thereof) is or was determined in the patient. In some embodiments, the activity level of TMCO3 (or downstream target thereof) is or was determined in the patient.

In some embodiments, the subject has and/or has been diagnosed with advanced colorectal cancer. In some embodiments, the advanced colorectal cancer comprises category T3 or T4 colorectal cancer. In some embodiments, the advanced colorectal cancer comprises category T4 colorectal cancer. In some embodiments, the advanced colorectal cancer excludes category T3 colorectal cancer. In some embodiments, the early colorectal cancer excludes category T3 or T4 colorectal cancer. In some embodiments, the early colorectal cancer excludes category T4 colorectal cancer. In some embodiments, the advanced colorectal cancer comprises lymph node metastasis. In some embodiments, the early colorectal cancer excludes lymph node metastasis. In some embodiments, the advanced colorectal cancer comprises category N1 and/or N2 colorectal cancer. In some embodiments, the advanced colorectal cancer comprises category N2 colorectal cancer. In some embodiments, the advanced colorectal cancer excludes category N1 colorectal cancer. In some embodiments, the early colorectal cancer excludes category N1 and/or N2 colorectal cancer. In some embodiments, the advanced colorectal cancer comprises distant metastasis. In some embodiments, the early colorectal cancer excludes distant metastasis. In some embodiments, the distant metastasis is liver metastasis. In some embodiments, the advanced colorectal cancer comprises category M1 colorectal cancer. In some embodiments, the early colorectal cancer excludes category M1 colorectal cancer.

In some embodiments, the advanced colorectal cancer comprises Stage II, Stage III, and/or Stage IV colorectal cancer. In some embodiments, the advanced colorectal cancer comprises Stage III and/or Stage IV colorectal cancer. In some embodiments, the advanced colorectal cancer comprises Stage IV colorectal cancer. In some embodiments, the advanced colorectal cancer excludes Stage I and Stage II colorectal cancer. In some embodiments, the advanced colorectal cancer excludes Stage I, Stage II, and Stage III colorectal cancer. In some embodiments, early colorectal cancer comprises Stage I colorectal cancer. In some embodiments, early colorectal cancer excludes Stage II, Stage III and/or Stage IV colorectal cancer. In some embodiments, early colorectal cancer excludes Stage III and/or Stage IV colorectal cancer. In some embodiments, advanced colorectal cancer excludes Stage I and/or II colorectal cancer. In some embodiments, advanced colorectal cancer excludes Stage I colorectal cancer.

In some embodiments, early colorectal cancer comprises category T1 or T2 colorectal cancer. In some embodiments, early colorectal cancer comprises category T1 colorectal cancer. In some embodiments, early colorectal cancer excludes category T2 colorectal cancer. In some embodiments, advanced colorectal cancer excludes category T1 or T2 colorectal cancer. In some embodiments, advanced colorectal cancer excludes category T1 colorectal cancer. In some embodiments, early colorectal cancer comprises category N0 colorectal cancer. In some embodiments, advanced colorectal cancer excludes category N0 colorectal cancer. In some embodiments, early colorectal cancer comprises category M0 colorectal cancer. In some embodiments, advanced colorectal cancer excludes category M0 colorectal cancer.

In some embodiments, the cancer is recurrent. In some embodiments, the patient or subject is one that has already been treated for the cancer.

In some embodiments, the method further comprises administration of one or more of cetuximab, fluorouracil, oxaliplatin, irinotecan, bevacizumab, panitumuman, afibercept, leucovorin, and radiotherapy. In some embodiments, the method excludes administration of one or more of cetuximab, fluorouracil, oxaliplatin, irinotecan, bevacizumab, panitumuman, afibercept, leucovorin, and radiotherapy. In some embodiments, the treatment for advanced colorectal cancer comprises administration of one or more of cetuximab, fluorouracil, oxaliplatin, irinotecan, bevacizumab, panitumuman, afibercept, leucovorin, and radiotherapy. In some embodiments, the treatment for advanced colorectal cancer excludes administration of one or more of cetuximab, fluorouracil, oxaliplatin, irinotecan, bevacizumab, panitumuman, afibercept, leucovorin, and radiotherapy. In some embodiments, the treatment for early colorectal cancer comprises administration of one or more of cetuximab, fluorouracil, oxaliplatin, irinotecan, bevacizumab, panitumuman, afibercept, leucovorin, and radiotherapy. In some embodiments, the treatment for early colorectal cancer excludes administration of one or more of cetuximab, fluorouracil, oxaliplatin, irinotecan, bevacizumab, panitumuman, afibercept, leucovorin, and radiotherapy.

In some embodiments, the method further comprises comparing the level of TMCO3 (or downstream target thereof) in the biological sample from the patient to a cut-off value. In some embodiments, the method further comprises comparing the expression level or activity level of TMCO3 (or downstream target thereof) in the biological sample from the patient to the expression or activity level of TMCO3 (or downstream target thereof) from a non-cancerous biological sample. The expression level or activity level from a non-cancerous biological sample may be an average value, a normalized value, a cut-off value, or an average normalized value. The expression level or activity level may be an average ort mean obtained from a significant proportion of patient samples. The expression or activity level may also be an average or mean from one or more samples from the patient.

In some embodiments, the colorectal cancer treatment comprises surgical incision of the primary tumor. In some embodiments, the colorectal cancer treatment for advanced colorectal cancer comprises surgical incision of the primary tumor.

In some embodiments, the method further comprises comparing the expression or activity level of TMCO3 (or downstream target thereof) in the biological sample from the patient to the expression or activity level of TMCO3 (or downstream target thereof) in a biological sample from a patient with early colorectal cancer. In some embodiments, the method further comprises comparing the expression or activity level of TMCO3 (or downstream target thereof) in the biological sample from the patient to the expression or activity level of TMCO3 (or downstream target thereof) in a biological sample from a patient with advanced colorectal cancer.

The expression or activity levels described herein may be normalized values, means, averages, statistically significant or cut-off values.

In some embodiments, the treatment for early colorectal cancer comprises surgical incision of the primary tumor. In some embodiments, the treatment for early colorectal cancer excludes surgical incision of the primary tumor. In some embodiments, the treatment for early colorectal cancer excludes chemotherapy. In some embodiments, the treatment for early colorectal cancer comprises chemotherapy. In some embodiments, the treatment for the advanced colorectal cancer comprises surgical removal of one or more secondary tumors. In some embodiments, the treatment for the early colorectal cancer excludes surgical removal of one or more secondary tumors.

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to the level of expression of TMCO3 (or downstream target thereof) in a colorectal cancer sample of a patient suspected of having or determined to have a colorectal cancer; and b) determining a difference value in the expression level of TMCO3 (or downstream target thereof) using the information corresponding to the level of expression of TMCO3 (or downstream target thereof) in the colorectal cancer sample as compared to a control or reference level that is normal or indicating favorable prognosis. In further embodiments, the receiving information comprises receiving the information corresponding to the expression level from a tangible data storage device.

In additional embodiments the medium further comprises computer-readable code that, when executed by a computer, causes the computer to perform one or more additional operations comprising sending information corresponding to the difference value to a tangible data storage device; calculating a prognosis score for the patient; classifying the patient as having a favorable prognosis or poor prognosis; or determining a management, surveillance or treatment plan for the patient.

In further embodiments, there may be provided a method of managing a patient suspected of having or determined to have a colorectal cancer in a patient comprising: monitoring the patient for colorectal cancer by performing colonoscopy after the patient has been determined to have increased expression of TMCO3 (or downstream target thereof) in a sample of the patient as compared to a control or reference level that is normal or indicating favorable prognosis.

In still further embodiments, there may be provided a method of treating a patient suspected of having or determined to have a colorectal cancer in a patient comprising: treating the patient for colorectal cancer after the patient has been determined to have increased expression of TMCO3 (or downstream target thereof) in a sample of the patient as compared to a control or reference level that is normal or indicating favorable prognosis.

In some embodiments, the elevated level is at least 1, 1.5, 2, 2.5, 3, 3.5, 4, 4.5, 5, 5.5, 6, 7, 8, 9, 10, 12, 14, 16, 18, 20, 50, 100, 150, 200, 250, 500, or 1000 fold (or any derivable range therein) or at least 10, 20, 30, 40, 50, 60, 70, 80, 90, 100, 200, 300, 400, 500, 600, 700, 800, or 900%, or any derivable range therein.

In some embodiments, the biological sample from the patient is a sample from a primary colorectal cancer tumor. In some embodiments, the biological sample is from a tissue or organ as described herein. In still further embodiments, the method may comprise obtaining a sample of the subject or patient or obtaining a sample from the subject or patient. Non-limiting examples of the sample include a tissue sample, a whole blood sample, a urine sample, a saliva sample, a serum sample or a fecal sample. In particular embodiments, the sample is a rectum sample, a colon sample or a cecum sample.

The term subject or patient may refer to an animal (for example a mammal), including but not limited to humans, non-human primates, rodents, dogs, or pigs. The methods of obtaining provided herein include methods of biopsy such as fine needle aspiration, core needle biopsy, vacuum assisted biopsy, incisional biopsy, excisional biopsy, punch biopsy, shave biopsy or skin biopsy.

In certain embodiments the sample is obtained from a biopsy from rectal, cecum, or colon tissue by any of the biopsy methods previously mentioned. In other embodiments the sample may be obtained from any of the tissues provided herein that include but are not limited to gall bladder, skin, heart, lung, breast, pancreas, liver, muscle, kidney, smooth muscle, bladder, intestine, brain, prostate, esophagus, or thyroid tissue.

Alternatively, the sample may include but not be limited to blood, serum, sweat, hair follicle, buccal tissue, tears, menses, urine, feces, or saliva. In particular embodiments, the sample may be a tissue sample, a whole blood sample, a urine sample, a saliva sample, a serum sample, a plasma sample or a fecal sample.

In certain aspects the sample is obtained from cystic fluid or fluid derived from a tumor or neoplasm. In yet other embodiments the cyst, tumor or neoplasm is in the digestive system. In certain aspects of the current methods, any medical professional such as a doctor, nurse or medical technician may obtain a biological sample for testing. In further aspects of the current methods, the patient or subject may obtain a biological sample for testing without the assistance of a medical professional, such as obtaining a whole blood sample, a urine sample, a fecal sample, a buccal sample, or a saliva sample.

In further embodiments, the sample may be a fresh, frozen or preserved sample or a fine needle aspirate. In particular embodiments, the sample is a formalin-fixed, paraffin-embedded (FFPE) sample. An acquired sample may be placed in short term or long term storage by placing in a suitable medium, excipient, solution, or container. In certain cases storage may require keeping the sample in a refrigerated, or frozen environment. The sample may be quickly frozen prior to storage in a frozen environment. In certain instances the frozen sample may be contacted with a suitable cryopreservation medium or compound. Examples of cryopreservation mediums or compounds include but are not limited to: glycerol, ethylene glycol, sucrose, or glucose.

Some embodiments further involve isolating nucleic acids such as ribonucleic or RNA from a biological sample or in a sample of the patient. Other steps may or may not include amplifying a nucleic acid in a sample and/or hybridizing one or more probes to an amplified or non-amplified nucleic acid. The methods may further comprise assaying nucleic acids in a sample. Further embodiments include isolating or analyzing protein expression in a biological sample for the expression of TMCO3 polypeptides.

In certain embodiments, a microarray may be used to measure or assay the level of TMCO3 expression in a sample. The methods may further comprise recording the TMCO3 expression or activity level in a tangible medium or reporting the expression or activity level to the patient, a health care payer, a physician, an insurance agent, or an electronic system.

In some embodiments, methods will involve determining or calculating a prognosis score based on data concerning the expression or activity level of TMCO3, meaning that the expression or activity level of TMCO3 is at least one of the factors on which the score is based. A prognosis score will provide information about the patient, such as the general probability whether the patient is sensitive to a particular therapy or has poor survival or high chances of recurrence. In certain embodiments, a prognosis value is expressed as a numerical integer or number that represents a probability of 0% likelihood to 100% likelihood that a patient has a chance of poor survival or cancer recurrence or poor response to a particular treatment.

In some embodiments, the prognosis score is expressed as a number that represents a probability of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% likelihood (or any range derivable therein) that a patient has a chance of poor survival or cancer recurrence or poor response to a particular treatment. Alternatively, the probability may be expressed generally in percentiles, quartiles, or deciles.

A difference between or among weighted coefficients or expression or activity levels or between or among the weighted comparisons may be, be at least or be at most about 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 times or -fold (or any range derivable therein).

In some embodiments, determination of calculation of a diagnostic, prognostic, or risk score is performed by applying classification algorithms based on the expression values of biomarkers with differential expression p values of about, between about, or at most about 0.005, 0.006, 0.007, 0.008, 0.009, 0.01, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.1, 0.2, 0.3, 0.4, 0.5, 0.6, 0.7, 0.8, 0.9 or higher (or any range derivable therein). In certain embodiments, the prognosis score is calculated using one or more statistically significantly differentially expressed biomarkers (either individually or as difference pairs), including expression or activity levels in a gene or protein encoding TMCO3 (or downstream target thereof).

Embodiments concern determining that the level of expression or activity of TMCO3. In some embodiments, that level is compared to a control in order to determine whether the expression level or activity of TMCO3 is elevated as compared to the level in non-cancerous colorectal tissue. The control may be a non-cancerous colorectal tissue or it may be a cancerous colorectal tissue. If the control is a cancerous colorectal tissue a sample may be determined to have an elevated level of TMCO3 because the levels in the control and the patient sample are similar, such as within, at least or at most 1, 2, 3, or 4 standard deviations (or any range derivable therein) of one another.

In some aspects, methods are provided for treatment of a patient for early or advanced colorectal cancer based on the TMCO3 level. One skilled in the art would understand that, if the control represents a level indicative of that in an advanced colorectal cancer patient, one would be treated or diagnosed with advanced colorectal cancer because the levels in the control and the patient sample are similar, such as within, at least or at most 1, 2, 3, or 4 standard deviations (or any range derivable therein) of one another. Furthermore, if the control represents a level indicative of that in an early colorectal cancer patient, one would be treated or diagnosed with early colorectal cancer because the levels in the control and the patient sample are similar, such as within, at least or at most 1, 2, 3, or 4 standard deviations (or any range derivable therein) of one another.

Also provided are kits containing the disclosed compositions or compositions used to implement the disclosed methods. In some embodiments, kits can be used to evaluate one or more the expression of TMCO3 (or downstream target thereof).

In certain embodiments, a kit contains probes or primers that may specifically hybridize under stringent conditions to TMCO3 (or downstream target thereof) mRNA or any fragment thereof. In other embodiments, kits or methods may involve 1, 2, or more probes or primers, which may be capable of specifically detecting any other biomarkers for expression. Also included may be enzymes suitable for amplifying or assaying nucleic acids including various polymerases (RT, Taq, Sequenase™ etc.), deoxynucleotides and buffers to provide the necessary reaction mixture for amplification.

The kits may also include antibody vials for assaying protein expressions and control samples. Such kits may also comprise, in suitable means, distinct containers for each individual reagent and enzyme as well as for each primer or probe.

The kits may further comprise instructions for using the kit for assessing expression, means for converting the expression data into expression values and/or means or medians for analyzing the expression values to generate scores that predict response, diagnosis, survival, prognosis or indicate recommendations for treatment choices. Possible means for converting the expression data into expression values and/or means or medians and for analyzing the expression values and/or means or medians to generate scores that predict response, diagnosis, survival or prognosis or indicate recommendations for treatment choices may also be included.

The terms "ameliorating," "inhibiting," or "reducing," or any variation of these terms, when used in the claims and/or the specification includes any measurable decrease or complete inhibition to achieve a desired result.

Throughout this application, the term "effective amount" is used to indicate that any therapeutic agents are administered at an amount sufficient to treat a condition in a subject in need thereof. In some embodiments, the condition is, but is not limited to, cancer.

As used herein, "increased expression" or "decreased expression" refers to an expression level of a biomarker in the subject's sample as compared to a reference level representing the same biomarker or a different biomarker. In certain aspects, the reference level may be a reference level of expression from a normal sample, such as a non-cancerous tissue from the same subject, particularly normal mucosa, or a sample from a different subject that does not have the cancer to be treated. Alternatively, the reference level may be a reference level of expression from a different subject or group of subjects, such as a reference level of expression from a subject or a group of subjects that have a favorable prognosis of cancer, such as having at most 20, 30, 40, or 50, 60, 70, 80% recurrence risk (or any range derivable therefrom) or at least 50, 60, 70, 80, or 90% survival chance (or any range derivable therefrom) of cancer relative to a group of poor prognosis or favorable prognosis subjects or a combination thereof. Alternatively, the reference level may be a reference level of expression from a subject or a group of subjects that has a poor prognosis, such as having a high recurrence risk of more than 50, 60, 70, 80, or 90 (or any range derivable therefrom) or at most 20, 30, 40, or 50, 60, 70, 80% survival chance (or any range derivable therefrom) relative to a group of poor prognosis or favorable prognosis subjects or a combination thereof. The combined group may be randomly selected or may be a group of clinical trial subjects, subjects in a particular geographic area, an age group, a gender group, or a stage of colorectal cancer, or any group based on one or more predetermined classification criteria, like inclusion or exclusion of patients that have favorable or poor prognosis.

A person of ordinary skill in the art understands that an expression level from a test subject may be determined to have an elevated level of expression, a similar level of expression or a decreased level of expression compared to a reference level.

"Diagnosis" may refer to the process of attempting to determine or identify a possible disease or disorder, or to the opinion reached by this process. From the point of view of statistics the diagnostic procedure may involve classification tests.

"Prognosis" may refer to a prediction of how a patient will progress, and whether there is a chance of recovery. "Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. Prognosis may also include prediction of favorable responses to cancer treatments, such as a conventional cancer therapy.

By "subject" or "patient" is meant any single subject for which therapy is desired, including humans, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls.

As used herein, the term "colorectal cancer" includes the well-accepted medical definition that defines colorectal cancer as a medical condition characterized by cancer of cells of the intestinal tract below the small intestine (i.e., any portion of the large intestine (colon), including the cecum, ascending colon, transverse colon, descending colon, sigmoid colon, or rectum). Additionally, as used herein, the term "colorectal cancer" also further includes medical conditions, which are characterized by cancer of cells of the duodenum and small intestine (jejunum and ileum).

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 10A-D—Analyses of intracellular pH and apoptotic status: (a) Intracellular pH level was analysed in siTMCO3 CRC cells using intracellular pH Indicator followed by flow cytometry. (b) Intra-cellular pH significantly decreased in siTMCO3 transfected cells. (c) The rate of apoptotic cells appeared to be raised in siTMCO3 cells in both SW480 and HCT116 cell lines. (d) Activation of caspase-3 in siTMCO3 cells supported induction of apoptosis in siTMCO3 CRC cells.

FIGS. 11A-C: Xenograft model (a) Xenograft tumours were made using HCT116 cells transfected with either siTMCO3 or siControl injected $3\times10^6$ cells subcutaneously to the flanks nude mice. 10 days following the initial injection, the tumour volume and weight were significantly lower in recipients of siTMCO3-transfected cells, compared with recipients of siControl-transfected cells. (b,c) TMCO3 expression level was significantly lower in siTMCO3 tumours than in scramble control transfected tumours.

DESCRIPTION OF ILLUSTRATIVE EMBODIMENTS

Figure 1:
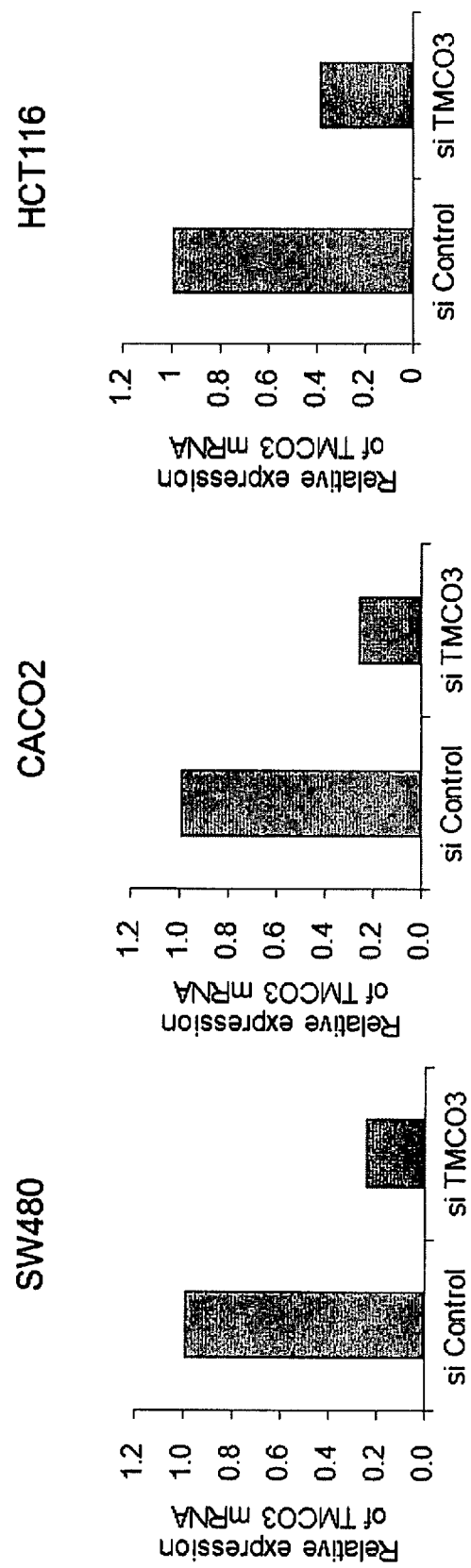
FIG. 1—siRNA transfection of TMCO3. 50 nM of siRNA transfection against TMCO3 was performed using silencer select siRNA system. TMCO3 is effectively knock-downed (Approximately to 20%).

Enhancer is a key element of the modulation of gene expression, which can activate specific promoter and control target gene expression. Recently activation of oncogenic enhancer is thought to be a key event in tumorigenesis. On the other hand, as per Warburg effect, the pH in the cancerous lesions is significantly lower than that of corresponding normal area. Cancer cells up-regulate acid transportation proteins to maintain intra-cellular pH homeostasis. However, relation between cancer specific enhancer and pH regulator remains unclear.

The inventors analysed cancer specific enhancer activation using FANTOM5 public enhancer database. The relation between enhancer and target promoter was analysed using the database of Chromatin Interaction Analysis with Paired-End-Tag sequencing (ChIA-PET). Additionally, the expression level of candidate gene was analysed using two clinical cohorts. The role of candidate gene was analysed in vitro and in vivo experiments using siRNA knockdown.

The inventors identified Transmembrane and coiled-coil domain-containing protein 3 (TMCO3) as the cancer specific enhancer from FANTOM5 database. Interestingly, TMCO3 had Na+/H+ antiporter domain. TMCO3 upregulation in CRC showed worse clinicopathological features. Furthermore, siRNA of TMCO3 showed intracellular acidification followed by reduced cell proliferation, invasion, migration. Intracellular acidification simultaneously induced apoptosis. On the other hand, acidic culture of cancer cells up-regulated TMCO3. The target of enhancer in TMCO3 was the promoter of oncogenic transcription factor TFDP1. The expression level of TFDP1 was significantly positively correlated with that of TMCO3. We conclude that TMCO3 has oncogenic enhancer activity and simultaneously act as key modulator of pH.

Enhancer can play a key role in tumorigenesis, which activate specific promoter and control target gene expression. However, comprehensive analysis of cancer specific enhancer activation is technically difficult. On the other hand, in cancer cells, glycolytic metabolism is superior to oxidative phosphorylation even in aerobic condition. This phenomenon was at first described by Warburg and is known as Warburg effect. However, pH control mechanism in cancer remains unclear.

The inventors at first recognised TMCO3 as the host gene of cancer specific enhancer. Enhancer in TMCO3 can activate promoter of oncogenic transcription factor TFDP1. The expression levels of TMCO3 and TFDP1 is significantly positively correlated, suggesting that this TMCO3-TFDP1 complex can act as cancer specific enhancer-promoter combination. TMCO3 can also act as cation/H+ anti transporter and maintain pH homeostasis in cancellous lesion. This means that TMCO3 can act as cancer specific enhancer and pH regulator and play an important role in tumorigenesis in CRC.

The experimental evidences described in the examples identifies TMCO3 as a critical modulator of carcinogenesis. TMCO3 may be a target of molecular targeting therapy because TMCO3 is a membrane protein and the block of TMCO3 can induce anti-tumour effect. Additionally TMCO3 has a potential as prognostic marker.

I. TMCO3 GENE

The mRNA sequence of TMCO3 is:
[SEQ ID NO. 1]
ttaaaggggg cagtgactgc ggctgggcgg gagtccgggt cggcttggct gagcggggc ggtgctgggc agggcggcgg ccgctccctc ccggactccc ggcctcccgg cctccctggt

```
cccgcctggg aagggatgca aggaagccct ccggcgctgc
gctccgaggc gggagacagc gtcccctcc gccctcggg
tcctggcgcc tcagagcccg gcccaggccg cggaacggtg
atgctcggc cggacgggcg ggcgcggatc cctgcgtccc
gctgaaaatg tgtgtctgac atgcaagctc agtggggcag
agaccgtgg attgctgtgc cctgccctcc ggacctggat
catgaaggtg ttgggaagaa gcttcttctg ggtgctgttt
cccgtcctc cctggcggt gcaggctgtg gagcacgagg
aggtggcgca gcgtgtgatc aaactgcacc gcgggcgagg
ggtggctgcc atgcagagcc ggcagtgggt ccgggacagc
tgcaggaagc tctcagggct tctccgccag aagaatgcag
ttctgaacaa actgaaaact gcaattggag cagtggagaa
agacgtgggc ctgtcggatg aagagaaact gtttcaggtg
cacacgtttg aaatttcca gaaagagctg aatgaaagtg
aaaattccgt tttccaagct gtctacggac tgcagagagc
cctgcagggg gattacaaag atgtcgtgaa catgaaggag
agcagccggc agcgcctgga ggccctgaga gaggctgcaa
taaaggaaga aacagaatat atggaacttc tggcagcaga
aaaacatcaa gttgaagccc ttaaaaatat gcaacatcaa
aaccaaagtt tatccatgct tgacagagatt cttgaagatg
taagaaaggc agcggatcgt ctggaggaag agatagagga
acatgctttt gacgacaata aatcagtcaa gggggtcaat
tttgaggcag ttctgagggt ggaggaagaa gaggccaatt
ctaagcaaaa tataacaaaa cgagaagtgg aggatgactt
gggtcttagc atgctgattg actcccagaa caaccagtat
attttgacca agcccagaga ttcaaccatc ccacgtgcag
atcaccactt tataaggac attgttacca taggaatgct
gtccttgcct tgtggctggc tatgtacagc cataggattg
cctacaatgt ttggttatat tatttgtggt gtacttctgg
gaccttcagg actaaatagt attaagtcta ttgtgcaagt
ggagacatta ggagaattttg gggtgttttt tactcttttt
cttgttggct tagaattttc tccagaaaag ctaagaaagg
tgtggaagat ttccttacaa gggccgtgtt acatgacact
gttaatgatt gcatttggct tgctgtgggg gcatctcttg
cggatcaaac ccacgcagag cgtcttcatt tccacgtgtc
tgtccttgtc aagcacaccc ctcgtgtcca ggttcctcat
gggcagtgct cggggtgaca agaaggcga cattgactac
agcaccgtgc tcctcggcat gctggtgacg caggacgtgc
agctcgggct cttcatggcc gtcatgccga ctctcataca
ggcgggcgcc agtgcatctt ctagcattgt cgtggaagtt
ctccgaatcc tggttttgat tggtcagatt cttttttcac
tagcggcggt ttttcttta tgtcttgtta taagaagta
tctcattgga ccctattatc ggaagctgca catggaaagc
aaggggaaca aagaaatcct gatcttggga atatctgcct
ttatcttctt aatgttaacg gtcacggagc tgctggacgt
ctccatggag ctgggctgtt tcctggctgg agcgctcgtc
tcctctcagg gccccgtggt caccgaggag atcgccacct
ccatcgaacc catccgcgac ttcctggcca tcgttttctt
cgcctccata gggctccacg tgttcccac gtttgtggcg
tacgagctca cggtgctggt gttcctcacc ttgtcagtgg
tggtgatgaa gtttctcctg gcggcgctgg tcctgtctct
cattctgccg aggagcagcc agtacatcaa gtggatcgtc
tctgcgggc ttgcccaggt cagcgagttt tcctttgtcc
tggggagccg ggcgcgaaga gcgggcgtca tctctcggga
ggtgtacctc cttatactga gtgtgaccac gctcagcctc
ttgctcgccc cggtgctgtg gagagctgca atcacgaggt
gtgtgccag accgagaga cggtccagcc tctgatggct
cggagatgat ggaccgtgga agggaagcgt ctgtggggag
tgagcgctta gatgccagc agctgctcct tctgggaagc
tcgcaccttg gcaacagaac agccctctag cagagcgtca
gtgcagtcgt gttatcccgg cttttacaga atattcttgt
cctatttag aattttccgg agtagtttat ttgcagtctg
ttgattatgt gcagtagacc cgggacactg cgttttaccg
atcaccttga atgtggtgcc tggatgtgcc ttttttttt
ttccctgaaa ttattattaa ttttctattg tgagttcatc
agttcatagt tttttagta aagaagcaaa attaaaaggc
ttttaaaaat gtacaacttc agaattataa tctgttagtc
aaatatttgt tattaaacat ttctgtaata tgaagttgta
atcctggccg tgagcttgga agcttacttt tgattcttaa
agcctatgtt ttctaaaatg agacaaatac ggatgtctat
ttgcctttta ttgtaacttt taaatgaaat aatttcatgt
caatttctat tagatatatc acttaaaata tttggtttta
aatcacaaga atatgtattc tttaataaag ataatttatg
atcatggtat aattaattga aatttattaa aatctgtttt
tattaaaaaa aaaaaaaaaa aa.
```

The protein sequence of TMCO3 is mkvlgrsffw vlfpvlpwav qaveheevaq rviklhrgrg vaamqsrqwv rdscrklsgl lrqknavink lktaigavek dvglsdeekl fqvhtfeifq kelnesensv fqavyglqra lqgdykdvvn mkessrqrle alreaaikee teymellaae khqvealknm qhqnqslsml deiledvrka adrleeeiee hafddnksvk gvnfeavlry eeeeanskqn itkreveddl glsmlidsqn nqyiltkprd stipradhhf ikdivtigml slpcgwlcta iglptmfgyi icgvllgpsg lnsiksivqv etlgefgvff tlflvglefs peklrkvwki slqgpcymtl lmiafgllwg hllrikptqs vfistclsls stplvsrflm gsargdkegd idystvllgm lvtqdvqlgl fmavmptliq agasassiv vevlrilvli gqilfslaav fllclvikky ligpyyrklh meskgnkeil ilgisafifl mltvtelldv smelgcflag alvssqgpvv teeiatsiep irdflaivff asiglhvfpt fvayeltvlv fltlsvvvmk fllaalvlsl ilprssqyik wivsaglaqv sefsfvlgsr arragvisre vyllilsvtt lslllapvlw raaitrcvpr perrssl [SEQ ID NO. 2].

II. METHODS AND COMPOSITIONS

Certain embodiments are directed to the use of technology involving transmembrane and coiled-coil domains 3 (TMCO3) in cancer management and/or treatment. Embodiments are based, in part, on the discovery that knockdown of TMCO3 reduces cell proliferation and induces apoptosis in colorectal cancer cells. In further embodiments, cancer management and treatment methods and compositions involving the expression of TMCO3 are also provided, based, in part, on the discovery that the TMCO3 up-regulated CRC clinical samples shows significantly lower overall survival and disease-free survival than those of TMCO3 down-regulated CRC clinical samples.

Methods and compositions in certain embodiments may be described in detail below, such as TMCO3 inhibitors that may be used, samples, nucleic acids and protein expression assays, and cancer management and treatment methods.

III. TMCO3 INHIBITORS

A TMCO3 inhibitor may refer to any member of the class of compound or agents having an IC50 of 100 μM or lower concentration for a TMCO3 activity, for example, at least or at most or about 200, 100, 80, 50, 40, 20, 10, 5, 1 μM, 100, 10, 1 nM or lower concentration (or any range or value derivable therefrom) or any compound or agent that inhibits the expression of TMCO3. Examples of TMCO3 activity or function may include, but not be limited to, the regulation of Na+/H+ levels in cells, intracellular pH, secretion of ions into medium apoptosis, cell proliferation, cell cycle, cell death, or cell viability. In particular embodiments, the regulation can be an increase or decrease as compared with a control level or sample. In further embodiments, functional assay such as intra cellular pH calculation, acid loading test to culture media, crystal analysis of TMCO3, electron microscope may be used. In additional embodiments, MTT assay, colony formation assay, invasion assay, apoptosis assay, or cell cycle analysis may be used to test the TMCO3 inhibitors.

A. TMCO3 Inhibitory Nucleic Acids

Inhibitory nucleic acids or any ways of inhibiting gene expression of TMCO3 known in the art are contemplated in certain embodiments. Examples of an inhibitory nucleic acid include but are not limited to siRNA (small interfering RNA), short hairpin RNA (shRNA), double-stranded RNA, an antisense oligonucleotide, a ribozyme and a nucleic acid encoding thereof. An inhibitory nucleic acid may inhibit the transcription of a gene or prevent the translation of a gene transcript in a cell. An inhibitory nucleic acid may be from 16 to 1000 nucleotides long, and in certain embodiments from 18 to 100 nucleotides long. The nucleic acid may have nucleotides of at least or at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 50, 60, 70, 80, 90 or any range derivable therefrom.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

Inhibitory nucleic acids are well known in the art. For example, siRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

Particularly, an inhibitory nucleic acid may be capable of decreasing the expression of TMCO3 by at least 10%, 20%, 30%, or 40%, more particularly by at least 50%, 60%, or 70%, and most particularly by at least 75%, 80%, 90%, 95% or more or any range or value in between the foregoing.

In further embodiments, there are synthetic nucleic acids that are TMCO3 inhibitors. An inhibitor may be between 17 to 25 nucleotides in length and comprises a 5' to 3' sequence that is at least 90% complementary to the 5' to 3' sequence of a mature TMCO3 mRNA. In certain embodiments, an inhibitor molecule is 17, 18, 19, 20, 21, 22, 23, 24, or 25 nucleotides in length, or any range derivable therein. Moreover, an inhibitor molecule has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature TMCO3 mRNA, particularly a mature, naturally occurring mRNA. One of skill in the art could use a portion of the probe sequence that is complementary to the sequence of a mature mRNA as the sequence for an mRNA inhibitor. Moreover, that portion of the probe sequence can be altered so that it is still 90% complementary to the sequence of a mature mRNA.

B. TMCO3 Inhibitory Antibodies

In certain embodiments, an antibody or a fragment thereof that binds to at least a portion of TMCO3 protein and inhibits TMCO3 activity in Na+-H+ transportation; its associated use in treatment of diseases is contemplated in embodiments.

In some embodiments, the anti-TMCO3 antibody is a monoclonal antibody or a polyclonal antibody. In some embodiments, the antibody is a chimeric antibody, an affinity matured antibody, a humanized antibody, or a human antibody. In some embodiments, the antibody is an antibody fragment. In some embodiments, the antibody is a Fab, Fab', Fab'-SH, F(ab')2, or scFv. In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a mouse. In one embodiment, an antigen binding sequence is synthetic, e.g., obtained by mutagenesis (e.g., phage display screening, etc.). In one embodiment, a chimeric antibody has murine V regions and human C region. In one embodiment, the murine light chain V region is fused to a human kappa light chain or a human IgG1 C region.

Examples of antibody fragments include, without limitation: (i) the Fab fragment, consisting of VL, VH, CL and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker which allows the two domains to associate to form a binding domain; (viii) bi-specific single chain Fv dimers (see U.S. Pat. No. 5,091,513) and (ix) diabodies, multivalent or multispecific fragments constructed by gene fusion (U.S. Patent Pub. 2005/0214860). Fv, scFv or diabody molecules may be stabilized by the incorporation of disulphide bridges linking the VH and VL domains. Minibodies comprising a scFv joined to a CH3 domain may also be made (Hu et al, 1996).

A monoclonal antibody is a single species of antibody wherein every antibody molecule recognizes the same epitope because all antibody producing cells are derived from a single B-lymphocyte cell line. Hybridoma technology involves the fusion of a single B lymphocyte from a mouse previously immunized with a TMCO3 antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced. However, in therapeutic applications a goal of hybridoma technology is to reduce the immune reaction in humans that may result from administration of monoclonal antibodies generated by the non-human (e.g. mouse) hybridoma cell line.

Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent and human amino acid sequences. In "humanized" monoclonal antibodies, only the hypervariable CDR is derived from mouse monoclonal antibodies, and the framework regions are derived from human amino acid sequences. It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

It is possible to create engineered antibodies, using monoclonal and other antibodies and recombinant DNA technology to produce other antibodies or chimeric molecules which retain the antigen or epitope specificity of the original antibody, i.e., the molecule has a binding domain. Such techniques may involve introducing DNA encoding the immunoglobulin variable region or the CDRs of an antibody to the genetic material for the framework regions, constant regions, or constant regions plus framework regions, of a different antibody. See, for instance, U.S. Pat. Nos. 5,091,513, and 6,881,557, which are incorporated herein by this reference.

By known means as described herein, polyclonal or monoclonal antibodies, binding fragments and binding domains and CDRs (including engineered forms of any of the foregoing), may be created that are specific to TMCO3 protein, one or more of its respective epitopes, or conjugates of any of the foregoing, whether such antigens or epitopes are isolated from natural sources or are synthetic derivatives or variants of the natural compounds.

Antibodies may be produced from any animal source, including birds and mammals. Particularly, the antibodies may be ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by this reference. These techniques are further described in: Marks (1992); Stemmer (1994); Gram et al. (1992); Barbas et al. (1994); and Schier et al. (1996).

Methods for producing polyclonal antibodies in various animal species, as well as for producing monoclonal antibodies of various types, including humanized, chimeric, and fully human, are well known in the art. Methods for producing these antibodies are also well known. For example, the following U.S. patents and patent publications provide enabling descriptions of such methods and are herein incorporated by reference: U.S. Patent publication Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent publications, and other publications cited herein and therein are hereby incorporated by reference in the present application.

It is fully expected that antibodies to TMCO3 will have the ability to neutralize or counteract the effects of the TMCO3 regardless of the animal species, monoclonal cell line or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into binding fragments having the binding domain or CDR. Removal of the Fc portion reduces the likelihood that the antigen binding fragment will elicit an undesirable immunological response and, thus, antibodies without Fc may be particularly useful for prophylactic or therapeutic treatments. As described above, antibodies may also be constructed so as to be chimeric, partially or fully human, so as to reduce or eliminate the adverse immunological consequences resulting from administering to an animal an antibody that has been produced in, or has sequences from, other species.

C. TMCO3 Inhibitory Small Molecules

As used herein, a "small molecule" refers to an organic compound that is either synthesized via conventional organic chemistry methods (e.g., in a laboratory) or found in nature. Typically, a small molecule is characterized in that it contains several carbon-carbon bonds, and has a molecular weight of less than about 1500 grams/mole. In certain embodiments, small molecules are less than about 1000 grams/mole. In certain embodiments, small molecules are less than about 550 grams/mole. In certain embodiments, small molecules are between about 200 and about 550 grams/mole. In certain embodiments, small molecules exclude peptides (e.g., compounds comprising 2 or more amino acids joined by a peptidyl bond). In certain embodiments, small molecules exclude nucleic acids.

For example, a small molecule TMCO3 inhibitory may be any small molecules that is determined to inhibit TMCO3 function or activity. Such small molecules may be determined based on functional assays in vitro or in vivo. The candidate molecules for such testing may include amiloride, EIPA, HMA, DMA, HOE-694, cariporide, eniporide, zoniporide, SM20550, BMC-284640, T-162559 (S), T-162559 (R), TY-12533, SL-591227, S03226, Harmaline, Cimetidine, Clonidine, or any combinations or derivatives therefrom.

IV. PHARMACEUTICAL COMPOSITIONS

Methods and compositions may be provided for the treatment of cancer, particularly colorectal cancer. In certain embodiments, there may be provided methods and compositions involving pharmaceutical compositions that comprise one or more therapeutic agents as described herein.

The therapeutic agents useful in the methods may be in the form of free acids, free bases, or pharmaceutically acceptable addition salts thereof. Such salts can be readily prepared by treating the agents with an appropriate acid. Such acids include, by way of example and not limitation, inorganic acids such as hydrohalic acids (hydrochloric, hydrobromic, hydrofluoric, etc.), sulfuric acid, nitric acid, and phosphoric acid, and organic acids such as acetic acid, propanoic acid, 2-hydroxyacetic acid, 2-hydroxypropanoic acid, 2-oxopropanoic acid, propandioic acid, and butandioic acid. Conversely, the salt can be converted into the free base form by treatment with alkali.

Aqueous compositions in some aspects comprise an effective amount of the therapeutic agent, further dispersed in pharmaceutically acceptable carrier or aqueous medium. The phrase "pharmaceutically or pharmacologically acceptable" refer to compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the pharmaceutical compositions is contemplated. Supplementary active ingredients also can be incorporated into the compositions.

Solutions of pharmaceutical compositions can be prepared in water suitably mixed with a surfactant, such as hydroxypropylcellulose. Dispersions also can be prepared in glycerol, liquid polyethylene glycols, mixtures thereof, and in oils. Under ordinary conditions of storage and use, these preparations contain a preservative to prevent the growth of microorganisms.

The pharmaceutical compositions may be administered in the form of injectable compositions either as liquid solutions or suspensions; solid forms suitable for solution in, or suspension in, liquid prior to injection may also be prepared. These preparations also may be emulsified. For instance, the composition may contain at least about, at most about, or about 1, 5, 10, 25, 50 mg or up to about 100 mg of human serum albumin per milliliter of phosphate buffered saline. Other pharmaceutically acceptable carriers include aqueous solutions, non-aqueous solvents, non-toxic excipients, including salts, preservatives, buffers and the like.

Examples of non-aqueous solvents include propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well-known parameters.

Administration of pharmaceutical compositions may be via any common route so long as the target tissue, cell or intracellular department is available via that route. This includes oral, nasal, buccal, rectal, vaginal or topical. Alternatively, administration may be by orthotopic, intradermal subcutaneous, intramuscular, intraperitoneal or intravenous injection. Such compositions would normally be administered as pharmaceutically acceptable compositions that include physiologically acceptable carriers, buffers or other excipients. Volume of an aerosol may be between about 0.01 mL and 0.5 mL.

Additional formulations may be suitable for oral administration. "Oral administration" as used herein refers to any form of delivery of a therapeutic agent or composition thereof to a subject wherein the agent or composition is placed in the mouth of the subject, whether or not the agent or composition is swallowed. Thus, "Oral administration" includes buccal and sublingual as well as esophageal administration. Absorption of the agent can occur in any part or parts of the gastrointestinal tract including the mouth, esophagus, stomach, duodenum, ileum and colon. Oral formulations include such typical excipients as, for example, pharmaceutical grades of mannitol, lactose, starch, magnesium stearate, sodium saccharine, cellulose, magnesium carbonate and the like. The compositions may take the form of solutions, suspensions, tablets, pills, capsules, sustained release formulations or powders.

In one embodiment, the oral formulation can comprise the therapeutic agent and one or more bulking agents. Suitable bulking agents are any such agent that is compatible with the therapeutic agent including, for example, lactose, microcrystalline cellulose, and non-reducing sugars, such as mannitol, xylitol, and sorbitol. One example of a suitable oral formulation includes spray-dried therapeutic agent-containing polymer nanoparticles (e.g., spray-dried poly(lactide-co-glycolide)/amifostine nanoparticles having a mean diameter of between about 150 nm and 450 nm; see Pamujula, et al., 2004, which is here by incorporated by reference in its entirety). The nanoparticles can contain between about 20 and 50 w/w % therapeutic agent for example, between about 25% and 50%.

In some embodiments, when the route is topical, the form may be a cream, ointment, salve or spray. Topical formulations may include solvents such as, but not limited to, dimethyl sulfoxide, water, N,N-dimethylformamide, propylene glycol, 2-pyrrolidone, methyl-2-pyrrolidone, and/or N-methylforamide. To enhance skin permeability, if necessary, the skin area to be treated can be pre-treated with dimethylsulfoxide; see Lamperti et al., 1990, which is hereby incorporated by reference in its entirety.

In other embodiments, the pharmaceutical compositions may be for subcutaneous administration (e.g., injection and/or implantation). For example, implantable forms may be useful for patients which are expected to undergo multiple CT scans over an extended period of time (e.g., one week, two weeks, one month, etc.). In one example, such subcutaneous forms can comprise the therapeutic agent and a carrier, such as a polymer. The polymers may be suitable for immediate or extended release depending on the intended use. In one example, the therapeutic agent can be combined with a biodegradable polymer (e.g., polylactide, polyglycolide, and/or a copolymers thereof). In another example, subcutaneous forms can comprise a microencapsulated form of the therapeutic agent, see, e.g., Srinivasan et al., 2002, which is hereby incorporated by reference in its entirety. Such microencapsulated forms may comprise the therapeutic agent and one or more surfactant and other excipients (e.g., lactose, sellulose, cholesterol, and phosphate- and/or stearate-based surfactants).

In a further embodiment, the therapeutic agent or pharmaceutical compositions may be administered transdermally through the use of an adhesive patch that is placed on the skin to deliver the therapeutic agent through the skin and into the bloodstream. An advantage of the transdermal drug delivery route relative to other delivery systems such as oral, topical, or intravenous is that the patch provides a controlled release of the therapeutic agent into the patient, usually through a porous membrane covering a reservoir of the therapeutic agent or through body heat melting thin layers of therapeutic agent embedded in the adhesive. In practicing certain aspects, any suitable transdermal patch system may be used, including, without limitation, single-layer drug-in-adhesive, multi-layer drug-in-adhesive, and reservoir.

An effective amount of the pharmaceutical composition may be determined based on the intended goal, such as treating cancer, or inducing apoptosis or inhibiting cell proliferation. The term "unit dose" or "dosage" refers to physically discrete units suitable for use in a subject, each unit containing a predetermined quantity of the therapeutic agent calculated to produce the desired responses, discussed above, in association with its administration, i.e., the appropriate route and treatment regimen.

The quantity to be administered, both according to number of treatments and unit dose, depends on the treatment effect desired. An effective dose is understood to refer to an amount necessary to achieve a particular effect. In the practice in certain embodiments, it is contemplated that doses in the range from 10 mg/kg to 200 mg/kg can affect the protective capability of these agents. Thus, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200, 300, 400, 500, 1000 □g/kg, mg/kg, □g/day, or mg/day or any range derivable therein. Furthermore, such doses can be administered at multiple times during a day, and/or on multiple days, weeks, or months.

In certain embodiments, the effective dose of the pharmaceutical composition is one which can provide a blood level of about 1 μM to 150 μM. In another embodiment, the effective dose provides a blood level of about 4 μM to 100 μM; or about 1 μM to 100 μM; or about 1 μM to 50 μM; or about 1 μM to 40 μM; or about 1 μM to 30 μM; or about 1 μM to 20 μM; or about 1 μM to 10 μM; or about 10 μM to 150 μM; or about 10 μM to 100 μM; or about 10 μM to 50 μM; or about 25 μM to 150 μM; or about 25 μM to 100 μM; or about 25 μM to 50 μM; or about 50 μM to 150 μM; or about 50 μM to 100 μM (or any range derivable therein). In other embodiments, the dose can provide the following blood level of the agent that results from a therapeutic agent being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 μM or any range derivable therein. In certain embodiments, the therapeutic agent that is administered to a subject is metabolized in the body to a metabolized therapeutic agent, in which case the blood levels may refer to the amount of that agent. Alternatively, to the extent the therapeutic agent is not metabolized by a subject, the blood levels discussed herein may refer to the unmetabolized therapeutic agent.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

It will be understood by those skilled in the art and made aware that dosage units of □g/kg or mg/kg of body weight can be converted and expressed in comparable concentration units of □g/ml or mM (blood levels), such as 4 μM to 100 μM. It is also understood that uptake is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein.

V. LIPIDS

In certain aspects, there may be provided methods and compositions for associating or encapsulating a TMCO3 inhibitor with a lipid and/or liposome. The TMCO3 inhibitor may be encapsulated in the aqueous interior of a liposome, interspersed within the lipid bilayer of a liposome, attached to a liposome via a linking molecule that is associated with both the liposome and the polynucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The liposome or liposome/TMCO3 inhibitor-associated compositions are not limited to any particular structure in solution. For example, they may be present in a bilayer structure, as micelles, or with a "collapsed" structure. They may also simply be interspersed in a solution, possibly forming aggregates which are not uniform in either size or shape.

Lipids are fatty substances which may be naturally occurring or synthetic lipids. For example, lipids include the fatty droplets that naturally occur in the cytoplasm as well as the class of compounds which are well known to those of skill in the art which contain long-chain aliphatic hydrocarbons and their derivatives, such as fatty acids, alcohols, amines, amino alcohols, and aldehydes. An example is the lipid dioleoylphosphatidylcholine (DOPC).

"Liposome" is a generic term encompassing a variety of unilamellar, multilamellar, and multivesicular lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, certain embodiments also encompass compositions that have different structures in solution than the normal vesicular structure. For example, the lipids may assume a micellar structure or merely exist as non-uniform aggregates of lipid molecules. Also contemplated are lipofectamine-nucleic acid complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments, the lipid may be associated with a hemaglutinating virus (HVJ). This has been shown to facilitate fusion with the cell membrane and promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. In that such expression vectors have been successfully employed in transfer of a polynucleotide in vitro and in vivo, then they are applicable.

Exemplary lipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), di stearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DWG"), dipalmitoylphosphatidylglycerol ("DPPG"), di stearoylphosphatidylglycerol ("DSPG"), distearoyl sphingomyelin ("DSSP"), distearoylphophatidylethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), palmitoyloeoyl phosphatidylcholine ("POPC"), palmitoyloeoyl phosphatidylethanolamine ("POPE"), lysophosphatidylcholine, lysophosphatidylethanolamine, dilinoleoylphosphatidylcholine, phosphatidylcholines, phosphatidylglycerols, phosphatidylethanolamines, cholesterol.

Liposomes and lipid compositions can be made by different methods. For example, a nucleotide (e.g., siRNA) may be encapsulated in a neutral liposome using a method involving ethanol and calcium (Bailey and Sullivan, 2000).

The size of the liposomes varies depending on the method of synthesis. A liposome suspended in an aqueous solution is generally in the shape of a spherical vesicle, and may have one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Lipids suitable for use can be obtained from commercial sources. For example, dimyristyl phosphatidylcholine ("DMPC") can be obtained from Sigma Chemical Co., dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform may be used as the only solvent since it is more readily evaporated than methanol.

Liposomes can be prepared in accordance with known laboratory techniques. In certain embodiments, liposomes are prepared by mixing liposomal lipids, in a solvent in a container (e.g., a glass, pear-shaped flask). The container may have a volume ten-times greater than the volume of the expected suspension of liposomes. Using a rotary evaporator, the solvent may be removed at approximately 40° C. under negative pressure. The solvent may be removed within about 5 minutes to 2 hours, depending on the desired volume of the liposomes. The composition can be dried further in a desiccator under vacuum. Dried lipids can be hydrated at approximately 25-50 mM phospholipid in sterile, pyrogen-free water by shaking until all the lipid film is resuspended. The aqueous liposomes can be separated into aliquots, each placed in a vial, lyophilized and sealed under vacuum.

Liposomes can also be prepared in accordance with other known laboratory procedures: the method of Bangham et al. (1965), the contents of which are incorporated herein by reference; the method of Gregoriadis (1979), the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

VI. DISEASES

Compositions or methods described herein may be administered to any patient that have an elevated level of TMCO3 as compared to a control or reference level that is normal or indicating favorable prognosis after treatment. In further embodiments, pharmaceutical compositions or therapeutic agents described herein may be administered to treat a cancer. The cancer may be a solid tumor, metastatic cancer, or non-metastatic cancer. In certain embodiments, the cancer may originate in the bladder, blood, bone, bone marrow, brain, breast, esophagus, duodenum, small intestine, large intestine, colon, rectum, anus, gum, head, kidney, liver, lung, nasopharynx, neck, ovary, prostate, skin, stomach, testis, tongue, or uterus.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

VII. SAMPLES

In certain aspects, methods involve obtaining a sample from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from colorectal tissue by any of the biopsy methods previously mentioned. In other embodiments the sample may be obtained from any of the tissues provided herein that include but are not limited to gall bladder, skin, heart, lung, breast, pancreas, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects the sample is obtained from cystic fluid or fluid derived from a tumor or neoplasm. In yet other embodiments the cyst, tumor or neoplasm is colorectal. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, or transported using components of a kit of the present methods. In some cases, multiple samples, such as multiple colorectal samples may be obtained for diagnosis by the methods described herein. In other cases, multiple samples, such as one or more samples from one tissue type (for example colon) and one or more samples from another tissue (for example buccal) may be obtained for diagnosis by the methods. In some cases, multiple samples such as one or more samples from one tissue type (e.g. rectal) and one or more samples from another tissue (e.g. cecum) may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a colorectal or a suspected colorectal tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, genes, gene fragments, expression products, gene expression products, or gene expression product fragments of an individual to be tested. Methods for determining sample suitability and/or adequacy are provided.

In some embodiments, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

VIII. NUCLEIC ACID ASSAYS

Aspects of the methods include assaying nucleic acids to determine expression levels. Arrays can be used to detect differences between two samples. Specifically contemplated applications include identifying and/or quantifying differences between TMCO3 from a sample that is normal and from a sample that is not normal, between a cancerous condition and a non-cancerous condition, or between two differently treated samples. Also, TMCO3 expression levels may be compared between the expression level of the test sample and a reference level indicating favorable prognosis or poor prognosis.

A sample that is not normal is one exhibiting phenotypic trait(s) of a disease or condition or one believed to be not normal with respect to that disease or condition. It may be compared to a cell that is normal with respect to that disease or condition. Phenotypic traits include symptoms of, or susceptibility to, a disease or condition of which a component is or may or may not be genetic or caused by a hyperproliferative or neoplastic cell or cells or include traits of poor prognosis after certain treatment.

An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., 1991), each of which is incorporated by reference in its entirety for all purposes. Techniques for the synthesis of these arrays using mechanical synthesis methods are described in, e.g., U.S. Pat. No. 5,384,261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,770,358, 5,789, 162, 5,708,153, 6,040,193 and 5,800,992, which are hereby incorporated in their entirety for all purposes.

In addition to the use of arrays and microarrays, it is contemplated that a number of difference assays could be employed to analyze TMCO3, their activities, and their effects. Such assays include, but are not limited to, nucleic amplification, polymerase chain reaction, quantitative PCR, RT-PCR, in situ hybridization, digital PCR, dd PCR (digital droplet PCR), nCounter (nanoString), BEAMing (Beads, Emulsions, Amplifications, and Magnetics) (Inostics), ARMS (Amplification Refractory Mutation Systems), RNA-Seq, TAm-Seg (Tagged-Amplicon deep sequencing), PAP (Pyrophosphorolysis-activation polymerization), next generation RNA sequencing, northern hybridization, hybridization protection assay (HPA)(GenProbe), branched DNA (bDNA) assay (Chiron), rolling circle amplification (RCA), single molecule hybridization detection (US Genomics), Invader assay (ThirdWave Technologies), and/or Bridge Litigation Assay (Genaco).

IX. PROTEIN EXPRESSION ASSAYS

In some embodiments, the gene or protein expression of TMCO3 is compared to a control or a reference level. Such methods, like the methods of detecting expression described herein, are useful in providing risk prediction, diagnosis, prognosis, etc., of a disease or cancer.

Methods for measuring transcription and/or translation of a particular gene sequence or biomarker are well known in the art. See, for example, Ausubel, Current Protocols in Molecular Biology, 1987-2006, John Wiley & Sons; and Sambrook and Russell, Molecular Cloning: A Laboratory Manual, 3rd Edition, 2000.

Polypeptides encoded by the TMCO3 gene described herein can be detected and/or quantified by any methods known to those of skill in the art from samples as described herein. In some embodiments, antibodies can also be used to detect polypeptides encoded by the genes described herein. Antibodies to these polypeptides can be produced using well known techniques (see, e.g., Harlow & Lane, 1988 and Harlow & Lane, 1999; Coligan, 1991; Goding, 1986; and Kohler & Milstein, 1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., 1989; Ward et al., 1989).

Once specific antibodies are available, TMCO3 expression can be detected by a variety of immunoassay methods. For a review of immunological and immunoassay procedures, see Basic and Clinical Immunology (1991). Moreover, the immunoassays of certain aspects can be performed in any of several configurations, which are reviewed extensively in Enzyme Immunoassay (1980); and Harlow & Lane, supra).

Immunoassays also often use a labeling agent to specifically bind to and label the complex formed by the antibody and antigen. The labeling agent may itself be one of the moieties comprising the antibody/antigen complex. Thus, the labeling agent may be a labeled polypeptide or a labeled antibody that binds the protein of interest. Alternatively, the labeling agent may be a third moiety, such as a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the labeling agent. These proteins exhibit a strong non-immunogenic reactivity with immunoglobulin constant regions from a variety of species (see, e.g., Kronval et al., 1973; Akerstrom et al., 1985). The labeling agent can be modified with a detectable moiety, such as biotin, to which another molecule can specifically bind, such as streptavidin. A variety of detectable moieties are well known to those skilled in the art.

Commonly used assays include noncompetitive assays, e.g., sandwich assays, and competitive assays. In competitive assays, the amount of polypeptide present in the sample is measured indirectly by measuring the amount of a known, added (exogenous) polypeptide of interest displaced (competed away) from an antibody that binds by the unknown polypeptide present in a sample. Commonly used assay formats include immunoblots, which are used to detect and quantify the presence of protein in a sample. Other assay formats include liposome immunoassays (LIA), which use liposomes designed to bind specific molecules (e.g., antibodies) and release encapsulated reagents or markers. The released chemicals are then detected according to standard techniques (see Monroe et al., 1986).

Any suitable method can be used to detect one or more of the markers described herein. Successful practice can be achieved with one or a combination of methods that can detect and, preferably, quantify the markers. These methods include, without limitation, hybridization-based methods, including those employed in biochip arrays, mass spectrometry (e.g., laser desorption/ionization mass spectrometry), fluorescence (e.g. sandwich immunoassay), surface plasmon resonance, ellipsometry and atomic force microscopy. Expression levels of markers (e.g., polynucleotides or polypeptides) are compared by procedures well known in the art, such as RT-PCR, Northern blotting, Western blotting, flow cytometry, immunocytochemistry, binding to magnetic and/or antibody-coated beads, in situ hybridization, fluorescence in situ hybridization (FISH), flow chamber adhesion assay, ELISA, microarray analysis, or colorimetric assays. Methods may further include, one or more of electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)11, atmospheric pressure photoionization mass spectrometry (APPI-MS), APPI-MS/MS, and APPI-(MS)n, quadrupole mass spectrometry, fourier transform mass spectrometry (FTMS), and ion trap mass spectrometry, where n is an integer greater than zero.

Detection methods may include the use of a biochip array. Biochip arrays include protein and polynucleotide arrays. The protein of interest may be captured on the biochip array and subjected to analysis to detect the level of the protein in a sample.

X. COLORECTAL CANCER STAGING AND TREATMENTS

Methods and compositions may be provided for treating colorectal cancer with particular applications of TMCO3 expression or activity levels. Based on a profile of TMCO3 expression or activity levels, different treatments may be prescribed or recommended for different cancer patients.

A. Cancer Staging

Colorectal cancer, also known as colon cancer, rectal cancer, or bowel cancer, is a cancer from uncontrolled cell growth in the colon or rectum (parts of the large intestine), or in the appendix. Certain aspects of the methods are provided for patients that are stage I-IV colorectal cancer patients. In particular aspects, the patient is a stage IV patient.

The most common staging system is the TNM (for tumors/nodes/metastases) system, from the American Joint Committee on Cancer (AJCC). The TNM system assigns a number based on three categories. "T" denotes the degree of invasion of the intestinal wall, "N" the degree of lymphatic node involvement, and "M" the degree of metastasis. The broader stage of a cancer is usually quoted as a number I, II, III, IV derived from the TNM value grouped by prognosis; a higher number indicates a more advanced cancer and likely a worse outcome. Details of this system are in the table below:

| AJCC stage | TNM stage | TNM stage criteria for colorectal cancer |
| --- | --- | --- |
| Stage 0 | Tis N0 M0 | Tis: Tumor confined to mucosa; cancer-in-situ |
| Stage I | T1 N0 M0 | T1: Tumor invades submucosa |
| Stage I | T2 N0 M0 | T2: Tumor invades muscularis propria |
| Stage II-A | T3 N0 M0 | T3: Tumor invades subserosa or beyond (without other organs involved) |
| Stage II-B | T4 N0 M0 | T4: Tumor invades adjacent organs or perforates the visceral peritoneum |
| Stage III-A | T1-2 N1 M0 | N1: Metastasis to 1 to 3 regional lymph nodes. T1 or T2. |
| Stage III-B | T3-4 N1 M0 | N1: Metastasis to 1 to 3 regional lymph nodes. T3 or T4. |
| Stage III-C | any T, N2 M0 | N2: Metastasis to 4 or more regional lymph nodes. Any T. |
| Stage IV | any T, any N, M1 | M1: Distant metastases present. Any T, any N. |

B. Therapy

For people with localized and/or early colorectal cancer, the preferred treatment is complete surgical removal with adequate margins, with the attempt of achieving a cure. This can either be done by an open laparotomy or sometimes laparoscopically. Sometimes chemotherapy is used before surgery to shrink the cancer before attempting to remove it (neoadjuvant therapy). The two most common sites of recurrence of colorectal cancer is in the liver and lungs. In some embodiments, the treatment of early colorectal cancer excludes chemotherapy. In further embodiments, the treatment of early colorectal cancer includes neoadjuvant therapy (chemotherapy or radiotherapy before the surgical removal of the primary tumor), but excludes adjuvant therapy (chemotherapy and/or radiotherapy after surgical removal of the primary tumor.

In both cancer of the colon and rectum, chemotherapy may be used in addition to surgery in certain cases. In rectal cancer, chemotherapy may be used in the neoadjuvant setting.

In certain embodiments, there may be a decision regarding the therapeutic treatment based on TMCO3 expression. Chemotherapy based on antimetabolites or thymidylate synthase inhibitors such as fluorouracil (5-FU) have been the main treatment for metastatic colorectal cancer. Major progress has been made by the introduction of regimens containing new cytotoxic drugs, such as irinotecan or oxaliplatin. The combinations commonly used, e.g., irinotecan, fluorouracil, and Jeucovorin (FOLFIRI) and oxaliplatin, fluorouracil, and leucovorin (FOLFOX) can reach an objective response rate of about 50%. However, these new combinations remain inactive in one half of the patients and, in addition, resistance to treatment appear in almost all patients who were initially responders. More recently, two monoclonal antibodies targeting vascular endothelial growth factor Avastin® (bevacizumab) (Genentech Inc., South San Francisco Calif.) and epidermal growth factor receptor Erbitux® (cetuximab) (Imclone Inc. New York City) have been approved for treatment of metastatic colorectal cancer but are always used in combination with standard chemotherapy regimens. In some embodiments, the cancer therapy may include one or more of the chemical therapeutic agents including thymidylate synthase inhibitors or antimetabolites such as fluorouracil (5-FU), alone or in combination with other therapeutic agents.

For example, in some embodiments, the first treatment to be tested for response therapy may be antimetabolites or thymidylate synthase inhibitors, prodrugs, or salts thereof. In some embodiments, this treatment regimen is for advanced cancer. In some embodiments, this treatment regimen is excluded for early cancer.

Antimetabolites can be used in cancer treatment, as they interfere with DNA production and therefore cell division and the growth of tumors. Because cancer cells spend more time dividing than other cells, inhibiting cell division harms tumor cells more than other cells. Anti-metabolites masquerade as a purine (azathioprine, mercaptopurine) or a pyrimidine, chemicals that become the building-blocks of DNA. They prevent these substances becoming incorporated in to DNA during the S phase (of the cell cycle), stopping normal development and division. They also affect RNA synthesis. However, because thymidine is used in DNA but not in RNA (where uracil is used instead), inhibition of thymidine synthesis via thymidylate synthase selectively inhibits DNA synthesis over RNA synthesis. Due to their efficiency, these drugs are the most widely used cytostatics. In the ATC system, they are classified under L01B. In some embodiments, this treatment regimen is for advanced cancer. In some embodiments, this treatment regimen is excluded for early cancer.

Thymidylate synthase inhibitors are chemical agents which inhibit the enzyme thymidylate synthase and have potential as an anticancer chemotherapy. As an anti-cancer chemotherapy target, thymidylate synthetase can be inhibited by the thymidylate synthase inhibitors such as fluorinated pyrimidine fluorouracil, or certain folate analogues, the most notable one being raltitrexed (trade name Tomudex). Five agents were in clinical trials in 2002: raltitrexed, pemetrexed, nolatrexed, ZD9331, and GS7904L. Additional non-limiting examples include: Raltitrexed, used for colorectal cancer since 1998; Fluorouracil, used for colorectal cancer; BGC 945; OSI-7904L. In some embodiments, this treatment regimen is for advanced cancer. In some embodiments, this treatment regimen is excluded for early cancer.

In further embodiments, there may be involved prodrugs that can be converted to thymidylate synthase inhibitors in the body, such as Capecitabine (INN), an orally-administered chemotherapeutic agent used in the treatment of numerous cancers. Capecitabine is a prodrug, that is enzymatically converted to 5-fluorouracil in the body. In some embodiments, this treatment regimen is for advanced cancer. In some embodiments, this treatment regimen is excluded for early cancer.

If cancer has entered the lymph nodes, adding the chemotherapy agents fluorouracil or capecitabine increases life expectancy. If the lymph nodes do not contain cancer, the benefits of chemotherapy are controversial. If the cancer is widely metastatic or unresectable, treatment is then palliative. For example, a number of different chemotherapy medications may be used. Chemotherapy agents for this condition may include capecitabine, fluorouracil, irinotecan, leucovorin, oxaliplatin and UFT. Another type of agent that is sometimes used are the epidermal growth factor receptor inhibitors. In some embodiments, this treatment regimen is for advanced cancer. In some embodiments, this treatment regimen is excluded for early cancer.

In certain embodiments, alternative treatments may be prescribed or recommended based on the biomarker profile. In addition to traditional chemotherapy for colorectal cancer patients, cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing. In some embodiments, treatment with one or more of the compounds described herein is for advanced cancer. In some embodiments, treatment with one or more of the compounds described herein is excluded for early cancer.

While a combination of radiation and chemotherapy may be useful for rectal cancer, its use in colon cancer is not routine due to the sensitivity of the bowels to radiation. Just as for chemotherapy, radiotherapy can be used in the neo-adjuvant and adjuvant setting for some stages of rectal cancer. In some embodiments, this treatment regimen is for advanced cancer. In some embodiments, this treatment regimen is excluded for early cancer.

In people with incurable colorectal cancer, treatment options including palliative care can be considered for improving quality of life. Surgical options may include non-curative surgical removal of some of the cancer tissue, bypassing part of the intestines, or stent placement. These procedures can be considered to improve symptoms and reduce complications such as bleeding from the tumor, abdominal pain and intestinal obstruction. Non-operative methods of symptomatic treatment include radiation therapy to decrease tumor size as well as pain medications. In some embodiments, this treatment regimen is for advanced cancer. In some embodiments, this treatment regimen is excluded for early cancer.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. In some embodiments, this treatment regimen is for advanced cancer. In some embodiments, this treatment regimen is excluded for early cancer.

Generally, the tumor cell must bear some marker that is amenable to targeting, i.e., is not present on the majority of other cells. Many tumor markers exist and any of these may be suitable for targeting. Common tumor markers include carcinoembryonic antigen, prostate specific antigen, urinary tumor associated antigen, fetal antigen, tyrosinase (p9'7), gp68, TAG-72, HMFG, Sialyl Lewis Antigen, MucA, MucB, PLAP, estrogen receptor, laminin receptor, erb B and p155. Markers described herein may be used in the context of the current claims for the purposes of developing a targeting moiety. For example, the targeting moiety may be one that binds the tumor marker. In some embodiments, the targeting moiety is an antibody. In further embodiments, the targeting moiety is an aptamer or aptamir.

In yet another embodiment, the treatment is a gene therapy. In certain embodiments, the therapeutic gene is a tumor suppressor gene. A tumor suppressor gene is a gene that, when present in a cell, reduces the tumorigenicity, malignancy, or hyperproliferative phenotype of the cell. This definition includes both the full length nucleic acid sequence of the tumor suppressor gene, as well as non-full length sequences of any length derived from the full length sequences. It being further understood that the sequence includes the degenerate codons of the native sequence or sequences which may be introduced to provide codon preference in a specific host cell. Examples of tumor suppressor nucleic acids within this definition include, but are not limited to APC, CYLD, HIN-I, KRAS2b, p19, p21, p2'7, p27mt, p53, p57, p'73, PTEN, Rb, Uteroglobin, Skp2, BRCA-I, BRCA-2, CHK2, CDKN2A, DCC, DPC4, MADR2/JV18, MEN1, MEN2, MTS1, NF1, NF2, VHL, WRN, WT1, CFTR, C-CAM, CTS-I, zacl, scFV, MMAC1, FCC, MCC, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide and FUS1. Other exemplary tumor suppressor genes are described in a database of tumor suppressor genes at www.cise.uftedu/~yyl/HTML-TSGDB/Homepageiltml. This database is herein specifically incorporated by reference into this and all other sections of the present application. Nucleic acids encoding tumor suppressor genes, as discussed above, include tumor suppressor genes, or nucleic acids derived therefrom {e.g., cDNAs, cRNAs, mRNAs, and subsequences thereof encoding active fragments of the respective tumor suppressor amino acid sequences), as well as vectors comprising these sequences. One of ordinary skill in the art would be familiar with tumor suppressor genes that can be applied.

C. Monitoring

In certain aspects, the biomarker-based method may be combined with one or more other colon cancer diagnosis or screening tests at increased frequency if the patient is determined to be at high risk for recurrence or have a poor prognosis based on the biomarker described above.

The colon monitoring may include any methods known in the art. In particular, the monitoring include obtaining a sample and testing the sample for diagnosis. For example, the colon monitoring may include colonoscopy or coloscopy, which is the endoscopic examination of the large bowel and the distal part of the small bowel with a CCD camera or a fiber optic camera on a flexible tube passed through the anus. It can provide a visual diagnosis (e.g. ulceration, polyps) and grants the opportunity for biopsy or removal of suspected colorectal cancer lesions. Thus, colonoscopy or coloscopy can be used for treatment.

In further aspects, the monitoring diagnosis may include sigmoidoscopy, which is similar to colonoscopy—the difference being related to which parts of the colon each can examine. A colonoscopy allows an examination of the entire colon (1200-1500 mm in length). A sigmoidoscopy allows an examination of the distal portion (about 600 mm) of the colon, which may be sufficient because benefits to cancer survival of colonoscopy have been limited to the detection of lesions in the distal portion of the colon. A sigmoidoscopy is often used as a screening procedure for a full colonoscopy, often done in conjunction with a fecal occult blood test (FOBT). About 5% of these screened patients are referred to colonoscopy.

In additional aspects, the monitoring diagnosis may include virtual colonoscopy, which uses 2D and 3D imagery reconstructed from computed tomography (CT) scans or from nuclear magnetic resonance (MR) scans, as a totally non-invasive medical test.

The monitoring include the use of one or more screening tests for colon cancer including, but not limited to fecal occult blood testing, flexible sigmoidoscopy and colonoscopy. Of the three, only sigmoidoscopy cannot screen the right side of the colon where 42% of malignancies are found. Virtual colonoscopy via a CT scan appears as good as standard colonoscopy for detecting cancers and large adenomas but is expensive, associated with radiation exposure, and cannot remove any detected abnormal growths like standard colonoscopy can. Fecal occult blood testing (FOBT) of the stool is typically recommended every two years and can be either guaiac based or immunochemical. Annual FOBT screening results in a 16% relative risk reduction in colorectal cancer mortality, but no difference in all-cause mortality. The M2-PK test identifies an enzyme in colorectal cancers and polyps rather than blood in the stool. It does not require any special preparation prior to testing. M2-PK is sensitive for colorectal cancer and polyps and is able to detect bleeding and non-bleeding colorectal cancer and polyps. In the event of a positive result people would be asked to undergo further examination e.g. colonoscopy.

XI. SAMPLE PREPARATION

In certain aspects, methods involve obtaining a sample from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from colorectal tissue by any of the biopsy methods previously mentioned. In other embodiments the sample may be obtained from any of the tissues provided herein that include but are not limited to non-cancerous or cancerous tissue and non-cancerous or cancerous tissue from the serum, gall bladder, mucosal, skin, heart, lung, breast, pancreas, blood, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects the sample is obtained from cystic fluid or fluid derived from a tumor or neoplasm. In yet other embodiments the cyst, tumor or neoplasm is colorectal. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, or transported using components of a kit of the present methods. In some cases, multiple samples, such as multiple colorectal samples may be obtained for diagnosis by the methods described herein. In other cases, multiple samples, such as one or more samples from one tissue type (for example colon) and one or more samples from another tissue (for example buccal) may be obtained for diagnosis by the methods. In some cases, multiple samples such as one or more samples from one tissue type (e.g. rectal) and one or more samples from another tissue (e.g. cecum) may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a colorectal or a suspected colorectal tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, proteins, polypeptides, genes, gene fragments, expression products, gene expression products, protein expression products or fragments, or gene expression product fragments of an individual to be tested. Methods for determining sample suitability and/or adequacy are provided.

In some embodiments, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

XII. CANCER MANAGEMENT AND TREATMENT

Methods may involve the determination, administration, or selection of an appropriate cancer "management regimen" and predicting the outcome of the same. As used herein the phrase "management regimen" refers to a management plan that specifies the type of examination, screening, diagnosis, surveillance, care, and treatment (such as dosage, schedule and/or duration of a treatment) provided to a subject in need thereof (e.g., a subject diagnosed with cancer).

The term "treatment" or "treating" means any treatment of a disease in a mammal, including:
 (i) preventing the disease, that is, causing the clinical symptoms of the disease not to develop by administration of a protective composition prior to the induction of the disease;
 (ii) suppressing the disease, that is, causing the clinical symptoms of the disease not to develop by administration of a protective composition after the inductive event but prior to the clinical appearance or reappearance of the disease;
 (iii) inhibiting the disease, that is, arresting the development of clinical symptoms by administration of a protective composition after their initial appearance; and/or
 (iv) relieving the disease, that is, causing the regression of clinical symptoms by administration of a protective composition after their initial appearance.

The selected treatment regimen can be an aggressive one which is expected to result in the best clinical outcome (e.g., complete cure of the disease) or a more moderate one which may relieve symptoms of the disease yet results in incomplete cure of the disease. The type of treatment can include a surgical intervention, administration of a therapeutic drug such as a TMCO3 inhibitor, an exposure to radiation therapy and/or any combination thereof. The dosage, schedule and duration of treatment can vary, depending on the severity of disease and the selected type of treatment, and those of skill in the art are capable of adjusting the type of treatment with the dosage, schedule and duration of treatment.

Biomarkers like TMCO3 that can predict the likelihood of tumor or cancer recurrence or overall survival in cancer patients can be used to identify patients who will receive benefit of a conventional single or combined modality therapy before treatment begins or to modify or design a future treatment plan after treatment. In the same way, those patients who do not receive much benefit from such conventional single or combined modality therapy and can offer them alternative treatment(s) may be identified.

In certain aspects, further cancer or metastasis examination or screening such as fecal occult blood testing, flexible sigmoidoscopy and colonoscopy for colorectal cancer, or further diagnosis such as contrast enhanced computed tomography (CT), positron emission tomography-CT (PET-CT), and magnetic resonance imaging (MRI) may be performed for the detection of CRC or cancer metastasis in patients determined to have poor prognosis based on the TMCO3 expression levels. In alternative aspects, there may be no need for further metastasis detection for patients determined to have favorable prognosis based on the TMCO3 expression levels.

Non-limiting examples of screening tests include fecal occult blood testing, flexible sigmoidoscopy and colonoscopy. Sigmoidoscopy may not screen the right side of the colon where 42% of malignancies are found. Virtual colonoscopy via a CT scan appears as good as standard colonoscopy for detecting cancers and large adenomas but is expensive, associated with radiation exposure, and cannot remove any detected abnormal growths like standard colonoscopy can.

A new screening method is the M2-PK Test. The enzyme biomarker M2-PK has been identified as a key enzyme in colorectal cancers and polyps. M2-PK does not depend on blood in the stool and is specifically related to changes in the tumor metabolism. It does not require any special preparation prior to testing. Only a small stool sample is needed. M2-PK features a high sensitivity for colorectal cancer and polyps and is able to detect bleeding and non-bleeding colorectal cancer and polyps. In the event of a positive result people would be asked to undergo further examination, e.g. colonoscopy.

Fecal occult blood testing of the stool may be recommended every two years and can be either guaiac based or immunochemical. For those at high risk, screenings may be more frequent or more early as compared with recommended guidelines for people with average risk. For people with average risk who have had a high-quality colonoscopy with normal results, the American Gastroenterological Association does not recommend any type of screening in the 10 years following the colonoscopy. For people over 75 or those with a life expectancy of less than 10 years, screening may not be recommended.

In certain aspects, conventional cancer therapy or therapy for early cancer may be applied to a subject wherein the subject is identified or reported as having a favorable prognosis or low risk of metastasis based on the assessment of the biomarker as disclosed. In further embodiments, normal, low or moderate surveillance may be provided for patients with a favorable prognosis or biomarker profile or low risk of cancer or metastasis.

On the other hand, at least an alternative cancer therapy or metastasis therapy or care may be prescribed, as used alone or in combination with conventional cancer therapy, if a poor prognosis or high risk of metastasis is determined by the disclosed methods or kits. In further embodiments, intensive or aggressive surveillance may be provided for patients with an unfavorable or poor prognosis or biomarker profile or high risk of cancer or metastasis.

Conventional cancer therapies include one or more selected from the group of chemical or radiation based treatments and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

Radiation therapy that cause DNA damage and have been used extensively include what are commonly known as y-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Approximately 60% of persons with cancer will undergo surgery of some type, which includes preventative, diagnostic or staging, curative and palliative surgery. Curative surgery is a cancer treatment that may be used in conjunction with other therapies, such as the treatment involving TMCO3 inhibitors, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that compositions and methods described herein may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Alternative cancer therapy includes any cancer therapy other than surgery, chemotherapy and radiation therapy, such as TMCO3-inhibitor-based therapy, immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into an individual's cells and tissues to treat a disease. Antisense therapy is also a form of gene therapy. A therapeutic polynucleotide may be administered before, after, or at the same time of a first cancer therapy. Delivery of a vector encoding a variety of proteins is encompassed in certain embodiments. For example, cellular expression of the exogenous tumor suppressor oncogenes would exert their function to inhibit excessive cellular proliferation, such as p53, p16 and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with compositions and methods described herein to improve the anti-hyperproliferative efficacy of the treatments. Inhibitors of cell adhesion are contemplated to improve the efficacy of compositions and methods described herein. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with compositions and methods described herein to improve the treatment efficacy.

Hormonal therapy may also be used or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

Once the patient has been identified as being at high risk for metastasis or having poor prognosis with an elevated TMCO3 expression level, intensive or frequent surveillance of metastasis may be provided for monitoring metastasis. The high risk of metastasis usually correlates with a patient's likelihood of survival (e.g. the "prognosis").

Once a cancer has metastasized or is determined to be at high risk for metastasis, it may still be treated with radio-surgery, chemotherapy, radiation therapy, biological therapy, hormone therapy, surgery, or a combination of these interventions ("multimodal therapy"). The choice of treatment depends on a large number of factors, including the type of primary cancer, the size and location of the metastases, the patient's age and general health, and the types of treatments used previously, among others. The treatment options currently available are rarely able to cure metastatic cancer, though some tumors, such as testicular cancer and thyroid cancer, are usually still curable.

In some embodiments, it is contemplated that a therapeutic agent such as a TMCO3 inhibitor may be used alone or in combination with other known or available therapeutic agents. The therapeutic agent may be administered to a patient or a patient population that has been determined to have an elevated expression level of TMCO3. The patient or patient population may have cancer, be at risk of having cancer, or be determined to have cancer.

In certain embodiments, the therapeutic agent may be used in conjunction with additional therapeutic agents as part of a treatment regimen. This process may involve contacting cell(s) or administering to the subject the agents at the same time or within a period of time wherein separate administration of the agents produces a desired therapeutic benefit. This may be achieved by contacting the cell, tissue or organism with a single composition or pharmacological formulation that includes two or more agents, or by contacting the cell with two or more distinct compositions or formulations, wherein one composition includes one agent and the other includes another.

The therapeutic agents may precede, be co-current with and/or follow the other agents by intervals ranging from minutes to weeks. In embodiments where the agents are applied separately to a cell, tissue or organism, one would generally ensure that a significant period of time did not expire between the time of each delivery, such that the agents would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the TMCO3 inhibitor. In other aspects, one or more additional agents may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering the TMCO3 inhibitor.

Various combination regimens of the agents may be employed. Non-limiting examples of such combinations are shown below, wherein a TMCO3 inhibitor is "A" and a second agent is "B":

```
A/B/A  B/A/B  B/B/A  A/A/B  A/B/B  B/A/A  A/B/B/B  B/A/B/B
B/B/B/A  B/B/A/B  A/A/B/B  A/B/A/B  A/B/B/A  B/B/A/A
B/A/B/A  B/A/A/B  A/A/A/B  B/A/A/A  A/B/A/A  A/A/B/A
```

In some embodiments, more than one course of therapy may be employed. It is contemplated that multiple courses may be implemented. In certain embodiments, a patient may have previously undergone radiation or chemotherapy for a cancer that turns out to be chemotherapy- or radiation-resistant. Alternatively, a patient may have a recurring cancer.

XIII. GENE DELIVERY

Certain aspects include transferring into a cell an expression construct comprising a TMCO3 inhibitory nucleic acid. Techniques pertaining to the transfer of expression constructs into cells are well-known to those of ordinary skill in the art. Exemplary techniques are discussed below.

A. Viral Vectors

In certain embodiments, transfer of an expression construct into a cell is accomplished using a viral vector. Techniques using "viral vectors" are well-known in the art. A viral vector is meant to include those constructs containing viral sequences sufficient to (a) support packaging of the expression cassette and (b) to ultimately express a recombinant gene construct that has been cloned therein.

In particular embodiments, the viral vector is a lentivirus vector. Lentivirus vectors have been successfully used in infecting stem cells and providing long term expression.

Another method for delivery of a nucleic acid involves the use of an adenovirus vector. Adenovirus vectors are known to have a low capacity for integration into genomic DNA. Adenovirus vectors result in highly efficient gene transfer.

Adenoviruses are currently the most commonly used vector for gene transfer in clinical settings. Among the advantages of these viruses is that they are efficient at gene delivery to both nondividing and dividing cells and can be produced in large quantities. The vector comprises a genetically engineered form of adenovirus (Grunhaus et al, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. A person of ordinary skill in the art would be familiar with experimental methods using adenoviral vectors.

The adenovirus vector may be replication defective, or at least conditionally defective, and the nature of the adenovirus vector is not believed to be crucial to the successful practice of the invention. The adenovirus may be of any of the 42 different known serotypes or subgroups A-F and other serotypes or subgroups are envisioned. Adenovirus type 5 of subgroup C is the starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector. Adenovirus growth and manipulation is known to those of skill in the art, and exhibits broad host range in vitro and in vivo. Modified viruses, such as adenoviruses with alteration of the CAR domain, may also be used. Methods for enhancing delivery or evading an immune response, such as liposome encapsulation of the virus, are also envisioned. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains two long terminal repeat (LTR) sequences present at the 5' and 3' ends of the viral genome. These contain strong promoter and enhancer sequences and are also required for integration in the host cell genome (Coffin, 1990).

In order to construct a retroviral vector, a nucleic acid encoding a nucleic acid or gene of interest is inserted into the viral genome in the place of certain viral sequences to produce a virus that is replication-defective. A person of ordinary skill in the art would be familiar with well-known techniques that are available to construct a retroviral vector.

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin et al., 1984; Laughlin et al, 1986; Lebkowski et al, 1988; McLaughlin et al, 1988), which means it is applicable for use with the present invention. Details concerning the generation and use of rAAV vectors are described in U.S. Pat. Nos. 5,139,941 and 4,797,368, each incorporated herein by reference.

Typically, recombinant AAV (rAAV) virus is made by cotransfecting a plasmid containing the gene of interest flanked by the two AAV terminal repeats (McLaughlin et al, 1988; Samulski et al, 1989; each incorporated herein by reference) and an expression plasmid containing the wild-type AAV coding sequences without the terminal repeats, for example pIM45 (McCarty et al., 1991; incorporated herein by reference). A person of ordinary skill in the art would be familiar with techniques available to generate vectors using AAV virus.

Herpes simplex virus (HSV) has generated considerable interest in treating nervous system disorders due to its tropism for neuronal cells, but this vector also can be exploited for other tissues given its wide host range. Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995). A person of ordinary skill in the art would be familiar with well-known techniques for use of HSV as vectors.

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome.

Other viral vectors may be employed as constructs in the present invention. For example, vectors derived from viruses such as poxvirus may be employed. A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and it has been suggested that VEE may be an extremely useful vector for immunizations (Caley et al., 1997). It is contemplated in the present invention, that VEE virus may be useful in targeting dendritic cells.

A polynucleotide may be housed within a viral vector that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope.

This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

B. Nonviral Gene Transfer

Several non-viral methods for the transfer of nucleic acids into cells also are contemplated by certain aspects of the present invention. These include calcium phosphate precipitation (Graham and Van Der Eb, 1973; Chen and Okayama, 1987; Rippe et al, 1990) DEAE-dextran (Gopal, 1985), electroporation (Tur-Kaspa et al, 1986; Potter et al, 1984), nucleofection (Trompeter et al, 2003), direct microinjection (Harland and Weintraub, 1985), DNA-loaded liposomes (Nicolau and Sene, 1982; Fraley et al, 1979) and lipofectamine-DNA complexes, polyamino acids, cell sonication (Fechheimer et al, 1987), gene bombardment using high velocity microprojectiles (Yang et al, 1990), polycations (Boussif et al, 1995) and receptor-mediated transfection (Wu and Wu, 1987; Wu and Wu, 1988). Some of these techniques may be successfully adapted for in vivo or ex vivo use. A person of ordinary skill in the art would be familiar with the techniques pertaining to use of nonviral vectors, and would understand that other types of nonviral vectors than those disclosed herein are contemplated by the present invention. In a further embodiment of the invention, the expression cassette may be entrapped in a liposome or lipid formulation. Liposomes are vesicular structures characterized by a phospholipid bilayer membrane and an inner aqueous medium. Multilamellar liposomes have multiple lipid layers separated by aqueous medium. Also contemplated is a gene construct complexed with Lipofectamine (Gibco BRL). One of ordinary skill in the art would be familiar with techniques utilizing liposomes and lipid formulations.

XIV. KITS

Certain aspects concern kits containing compositions described herein or compositions to implement methods described herein.

In various aspects, a kit is envisioned containing therapeutic agents and/or other therapeutic and delivery agents. In some embodiments, a kit for preparing and/or administering a therapy described herein may be provided. The kit may comprise one or more sealed vials containing any of the pharmaceutical compositions, therapeutic agents and/or other therapeutic and delivery agents. In some embodiments, the lipid is in one vial, and the therapeutic agent is in a separate vial. The kit may include, for example, at least one inhibitor of TMCO3 expression/activity, one or more lipid component, as well as reagents to prepare, formulate, and/or administer the components described herein or perform one or more steps of the methods. In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill. The instruction information may be in a computer readable media containing machine-readable instructions that, when executed using a computer, cause the display of a real or virtual procedure of delivering a pharmaceutically effective amount of a therapeutic agent.

In some embodiments, kits may be provided to evaluate the expression of TMCO3 or related molecules. Such kits can be prepared from readily available materials and reagents. For example, such kits can comprise any one or more of the following materials: enzymes, reaction tubes, buffers, detergent, primers and probes, nucleic acid amplification, and/or hybridization agents. In a particular embodiment, these kits allow a practitioner to obtain samples in blood, tears, semen, saliva, urine, tissue, serum, stool, colon, rectum, sputum, cerebrospinal fluid and supernatant from cell lysate. In another embodiment, these kits include the needed apparatus for performing RNA extraction, RT-PCR, and gel electrophoresis. Instructions for performing the assays can also be included in the kits.

Kits may comprise components, which may be individually packaged or placed in a container, such as a tube, bottle, vial, syringe, or other suitable container means. The components may include probes, primers, antibodies, arrays, negative and/or positive controls. Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

The kit can further comprise reagents for labeling TMCO3 in the sample. The kit may also include labeling reagents, including at least one of amine-modified nucleotide, poly(A) polymerase, and poly(A) polymerase buffer. Labeling reagents can include an amine-reactive dye or any dye known in the art.

The components of the kits may be packaged either in aqueous media or in lyophilized form. The container means of the kits will generally include at least one vial, test tube, flask, bottle, syringe or other container means, into which a component may be placed, and preferably, suitably aliquotted. Where there is more than one component in the kit (labeling reagent and label may be packaged together), the kit also will generally contain a second, third or other additional container into which the additional components may be separately placed. However, various combinations of components may be comprised in a vial. The kits may also include a means for containing the nucleic acids, antibodies or any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred.

Alternatively, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 µg or at least or at most those amounts of dried dye are provided in kits in certain aspects. The dye may then be resuspended in any suitable solvent, such as DMSO.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits may include a means for containing the vials in close confinement for commercial sale, such as, e.g., injection and/or blow-molded plastic containers into which the desired vials are retained.

A kit may also include instructions for employing the kit components as well the use of any other reagent not included in the kit. Instructions may include variations that can be implemented.

XV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—TMCO3 as an Indispensable Protein in CRC Progression and its Value as a Promising Candidate for Targeted Therapy Background: As per Warburg effect, the pH in the cancerous regions is significantly lower than the corresponding normal area. Dysregulation of pH affects tumor growth, cell viability, proliferation and motility. Cancer cells up-regulate acid transportation proteins to maintain intra-cellular pH homeostasis. TMCO family has been suggested to function as a potential regulator for Na+/H+ levels in the cells, but the basic molecular mechanisms and specific proteins within this family that regulate intracellular pH remain poorly understood.

Methods: Two human CRC cell lines, SW480 and CACO2 were used and were used to perform siRNA knockdown experiments with TMCO3 siRNA (Silencer Select siRNA, Life Technologies). The successful induction of siRNA against TMCO3 was identified by Taqman RT-PCR and western immunoblotting. Cell proliferation ability was analyzed using MTT assay. Cell invasion and migration status was measured with Matrigel Invasion Chambers. Induction of apoptosis was analyzed by Annexin V & Dead Cell Kit (Millipore).

In addition, the transcript levels of TMCO3 were analyzed in matched pairs of tumor and normal mucosa tissues from a cohort of 122 CRC patients. All patients were categorized into TMCO3-Upregulated and TMCO3-Downregulated groups, and clinicopathological features were analyzed.

Figures 2A, 2B:
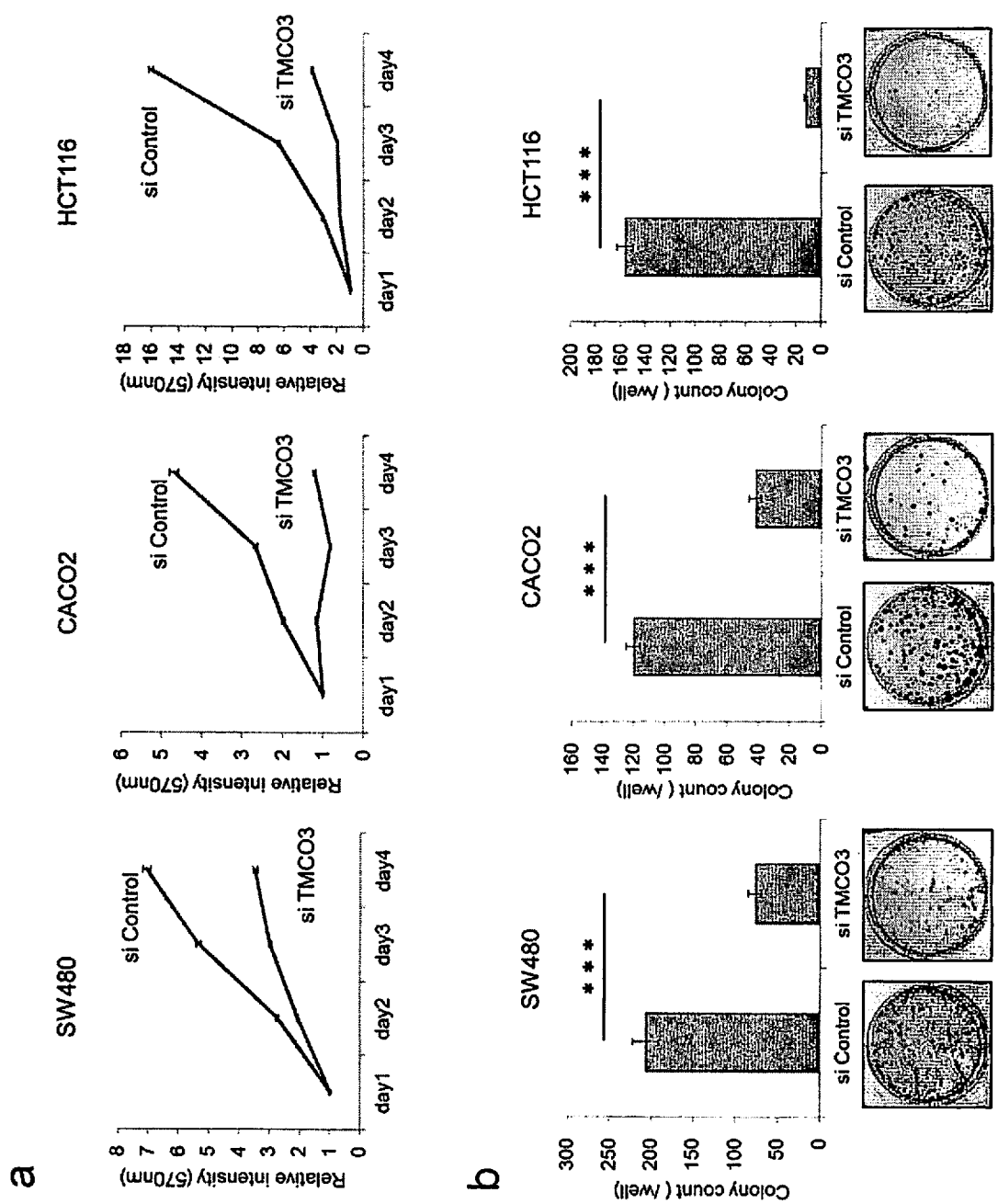
FIGS. 2A-B—MTT and colony formation assay. 50 nM of siRNA transfection against TMCO3 was performed using silencer select siRNA system. siRNA against TMCO3 decreased proliferation ability and colony-formation ability.
Figure 3A:
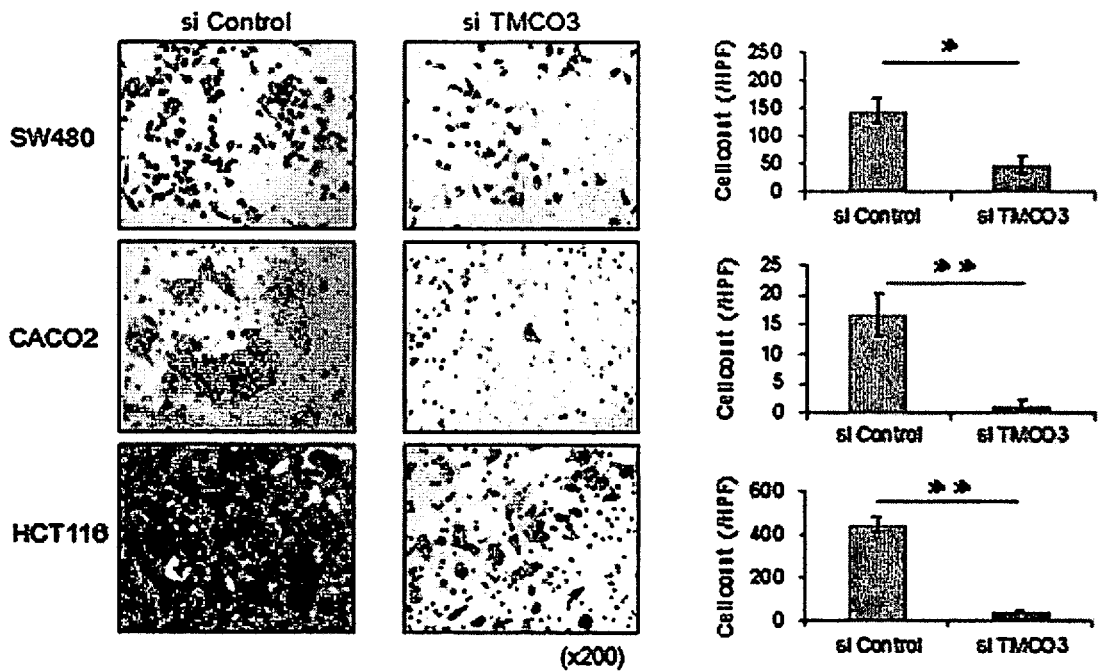
FIGS. 3A-B—Invasion and migration assay. 50 nM of siRNA transfection against TMCO3 was performed using silencer select siRNA system. In SW480, CACO2 and HCT116 cells, knockdown of TMCO3 reduced invasion and migration ability significantly.
Figure 3B:
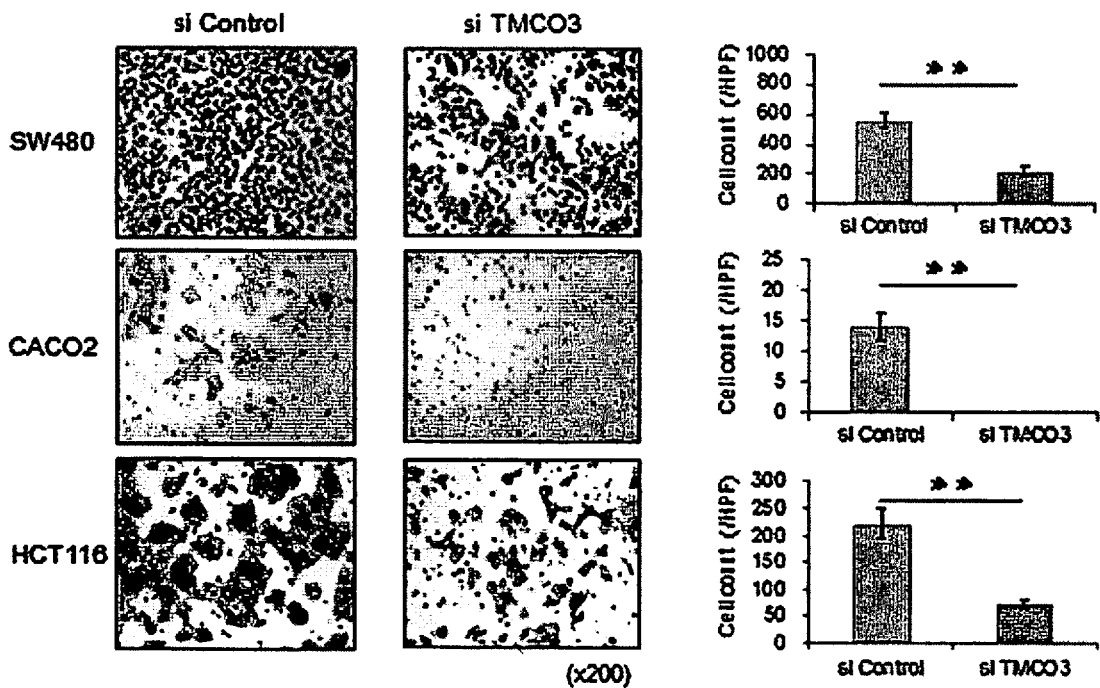
Figures 4A, 4B, 4C:
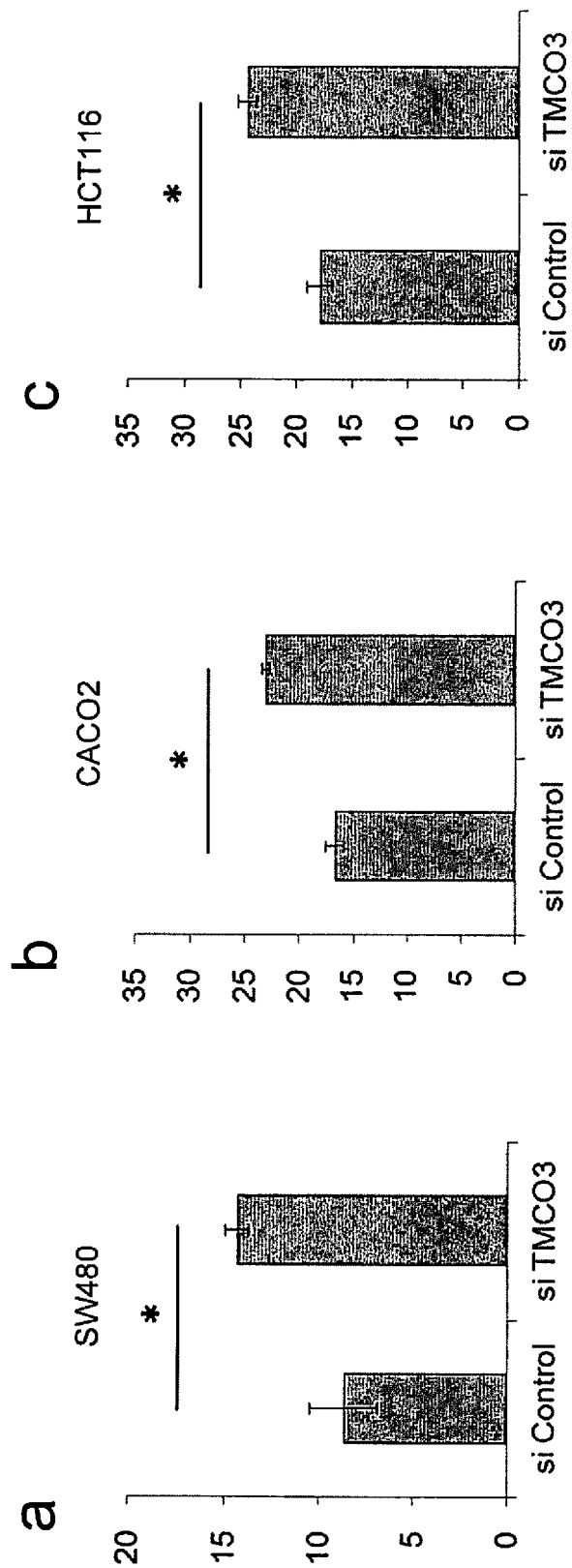
FIGS. 4A-C—Apoptosis assay. Annexin V & Dead Cell assay.
Figure 5A:
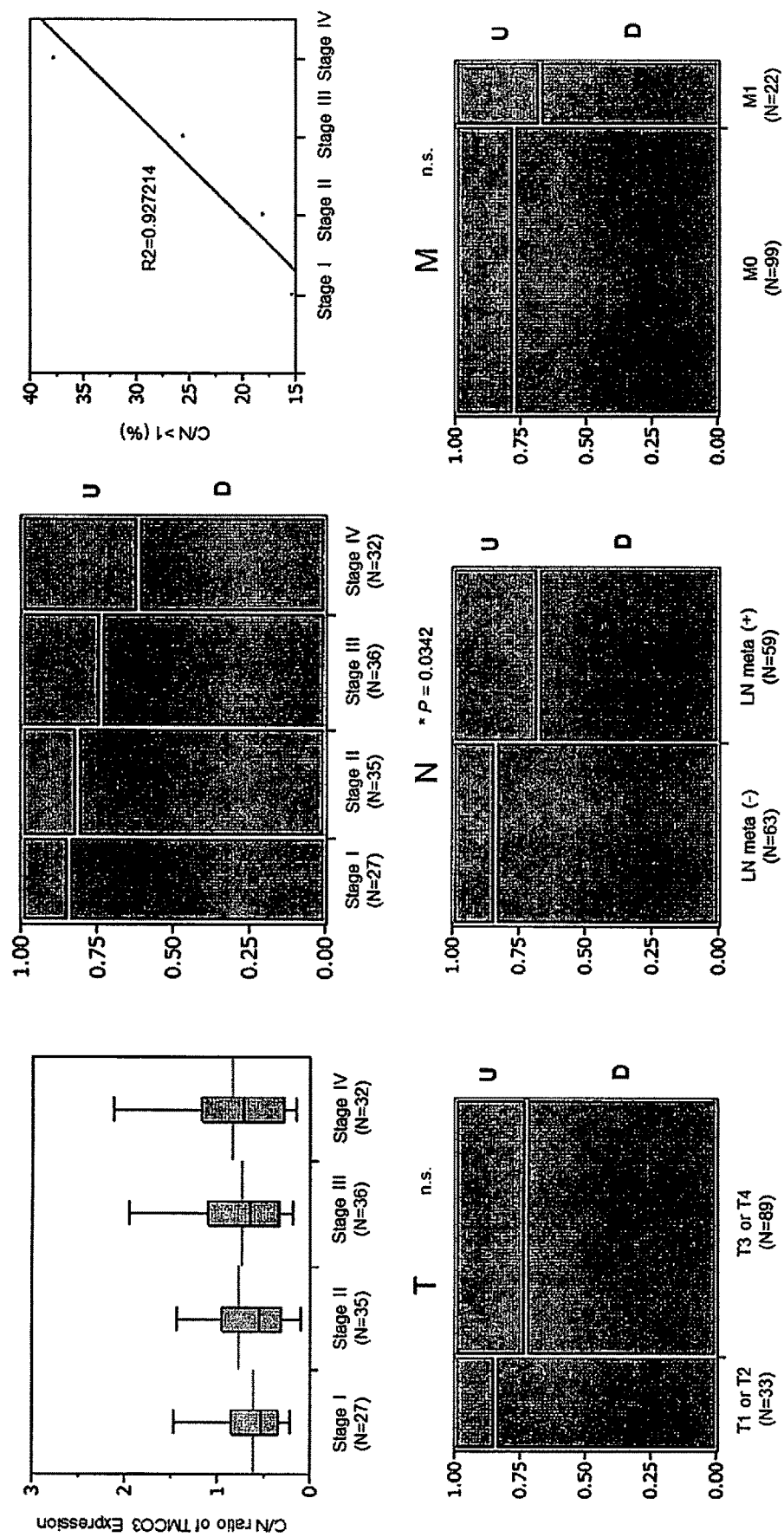
FIGS. 5A-B—TMCO3 expression in CRC (mRNA). In CRC specimens, TMCO3 expression increased in a stepwise manner in stage I-IV tumors, and CRCs with upregulated expression of TMCO3 demonstrated significantly poor overall and disease-free survival compared to the down-regulated group.
Figure 5B:
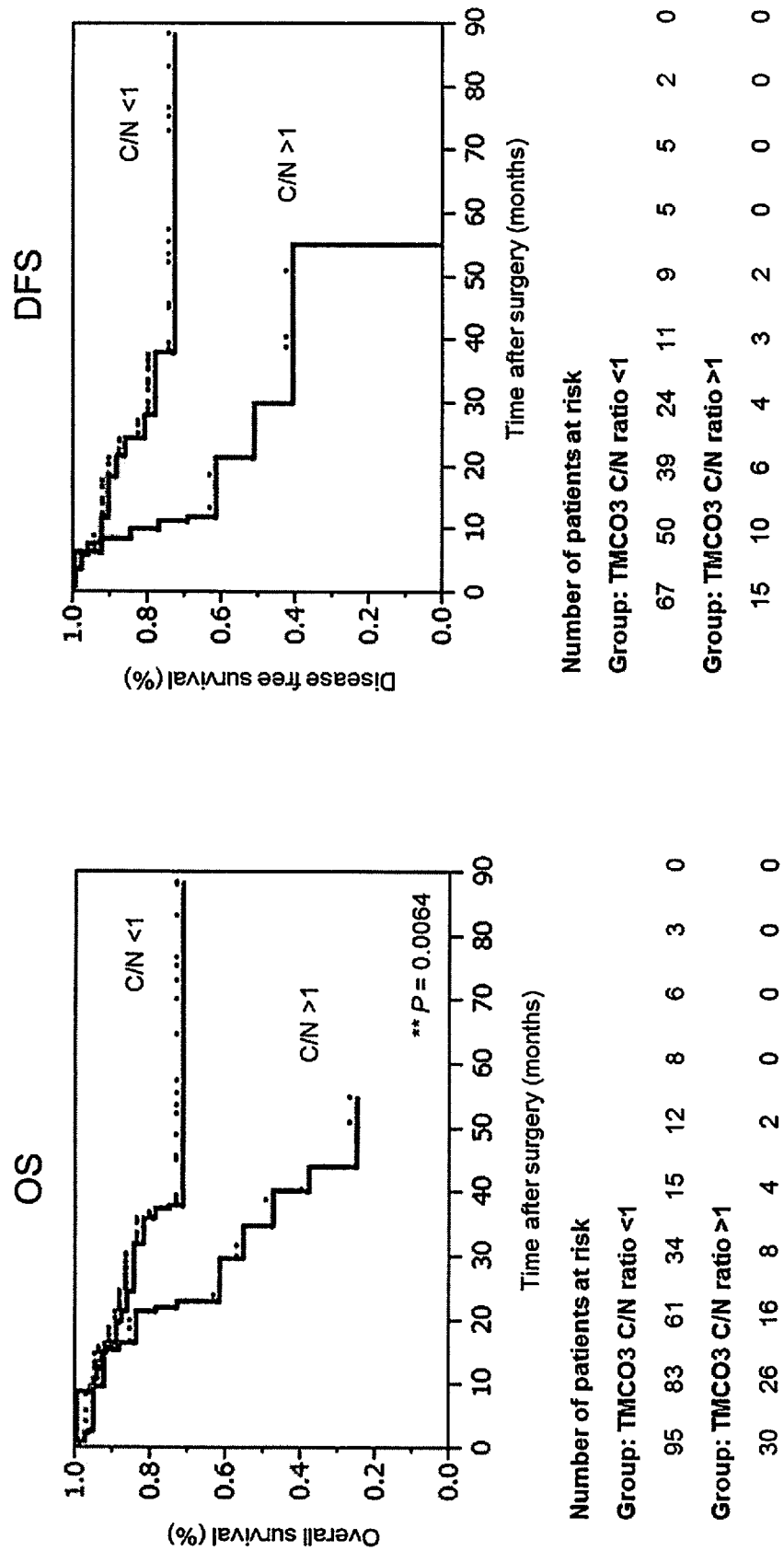

Results: The expression levels of TMCO3 were significantly reduced in si-TMCO3 cells, compared to that of control siRNA cells, in both SW480 and CACO2 cell lines (FIG. 1). TMCO3-knockdown resulted in decreased cellular proliferation (FIG. 2), invasion and migration (FIG. 3), but enhanced apoptosis (FIG. 4), compared to control cells. In CRC specimens, TMCO3 expression increased in a stepwise manner in stage I-IV tumors, and CRCs with upregulated expression of TMCO3 demonstrated significantly poor overall and disease-free survival compared to the down-regulated group (FIG. 5).

Conclusion: These results provide first evidence for the role of TMCO3 in CRC, and illustrate its clinical usefulness as a potential prognostic biomarker in this malignancy. The findings provide a compelling rationale for TMCO3 as an indispensable protein in CRC progression, and for its use in targeted therapy.

Applications: 1.) Prognostic tissue biomarkers for colorectal cancer; 2.) Therapeutic target for colorectal cancer (antibody, small molecule, virus etc.); 3.) Target molecule for colorectal cancer prevention; 4.) Treatment of other types of cancer (Gastric cancer, lung cancer, melanoma etc.)

Strengths of this study: 1.) It is novel to clarify the role of TMCO3 protein. Knockdown of TMCO3 reduces cell proliferation and induce apoptosis. TMCO3 is indispensable for cancer cells. 2.) It is novel to establish anti-cancer therapy by the suppression of TMCO3. This technology can be used as the new drug including antibody, small molecule, and virus vector. 3.) Especially, TMCO3 is on cellular membrane and easy to access using these drugs.

Materials:

Clinical samples: 1.) Matched colorectal cancer and adjacent mucosa samples from Mie University; 2.) (RNA later-stored for RNA and DNA, n=~286); 3.) Matched colorectal cancer and adjacent mucosa samples from Okayama University (Frozen tissue for RNA and DNA, n=~500); 4.) FFPE tissue samples from Okayama University (n=600)

Colon cancer cell lines: SW480, CACO2, HCT116, HCT116-P53−/−, HCT116-P21−/−, WI38

The following experiments will be performed:
A. TMCO3 functional analysis
1. Intra-cellular pH calculation
2. Acid loading test to culture media
3. Crystal analysis of TMCO3
4. Electron microscope B. TMCO3 mRNA expression analysis by real-time RT-PCR and analysis of the association with clinic-pathological findings.
1. Samples: matched CRC and adjacent mucosa, 141-286 pairs
2. Real-time RT-PCR: TaqMan® Gene Expression Assays (Life technologies)

C. In vitro functional analyses and the establishment of siRNA-based cancer treatment system
1. Target protein: TMCO3
2. Cell lines: SW480, CACO2, HCT116, HCT116-P53−/−, HCT116-P21−/−, WI38
3. Knockdown of TMCO3: Silencer Select siRNA and Lipofectamine RNAiMAX reagent (Life technologies)
4. Real-time RT-PCR for TMCO3 to confirm knockdown
5. TaqMan® Gene Expression Assays (Life technologies)
6. MTT assay
7. Colony formation assay
8. Invasion assay
9. Apoptosis assay
10. Cell cycle analysis D. in vivo functional analysis and the establishment of siRNA-based cancer treatment system
1. Target protein: TMCO3
2. Cell lines: SW480, CACO2, HCT116
3. Knockdown of TMCO3: Silencer Select siRNA and Lipofectamine RNAiMAX reagent (Life technologies)
4. Real-time RT-PCR for TMCO3 to confirm knockdown
5. TaqMan® Gene Expression Assays (Life technologies)
6. Injection of anti-TMCO3 siRNA using ateloGene system Example 2: TMCO3—a Novel Oncogenic Enhancer and Intracellular pH Regulator in Colorectal Cancer A. Materials and Methods Patients and sample collection: Cohort 1 (The Cancer Genome Atlas cohort): The Cancer Genome Atlas (TCGA) cohort was analysed as the first cohort. All data were collected in the TCGA Research Network and cBioPortal. mRNA expression levels and clinicopathological features were collected from the TCGA provisional (microarray, Z-score) database. Cohort 2 (Mie University cohort): 125 matched pairs of CRC tissues and corresponding normal tissues were analysed. All tissue specimens were preserved immediately after surgical resection in RNA (QIAGEN, Chatsworth, Calif., USA) and later stored at −80° C. Remaining resected tissues were fixed by paraformaldehyde for immunohistochemical staining. Additionally, clinicopathological information including age, sex, staging, tumour location and survival durations was collected. Written informed consent was obtained from each patient, and the study was approved by the institutional review boards of all involved institutions. Clinicopathological features are in Supplementary Table 1.

SUPLLEMENTARY TABLE 1

| Clinicopathological features of the patients in cohort 1 and cohort 2 | | |
|---|---|---|
| Characteristics | Cohort 1 (TCGA) | Cohort 2 (Original) |
| No. of patients | 222 | 135 |
| Age | 69.5 (68.0-71.0) | 68.1 (66.3-69.9) |

SUPLLEMENTARY TABLE 1-continued

Clinicopathological features of the patients in cohort 1 and cohort 2

| Characteristics | Cohort 1 (TCGA) | Cohort 2 (Original) |
|---|---|---|
| Sex | | |
| Male | 116 (52.3%) | 80 (59.3%) |
| Female | 106 (47.7%) | 55 (40.7%) |
| Location | | |
| Colon | 152 (69.1%) | 81 (60.0%) |
| Rectum | 68 (30.9%) | 54 (40.0%) |
| Tumour depth | | |
| T1 or T2 | 55 (24.8%) | 34 (25.6%) |
| T3 or T4 | 167 (75.2%) | 99 (74.4%) |
| Lymph node metastasis | | |
| Negative | 136 (61.3%) | 68 (51.1%) |
| Positive | 86 (38.7%) | 65 (48.9%) |
| Distant metastasis | | |
| Negative | 186 (84.5%) | 103 (77.4%) |
| Positive | 34 (15.5%) | 30 (22.6%) |
| Stage | | |
| I, II | 132 (59.7%) | 69 (51.9%) |
| III, IV | 89 (40.3%) | 64 (48.1%) |

Cohort for protein expression analysis: In addition to the original cohort, protein expression in normal and cancer tissues were analysed using the Human Protein Atlas database.

Total RNA extraction and complementary DNA synthesis: RNA later-preserved surgical specimens were homogenised using a Mixer Mill MM 300 homogenizer (QIAGEN) and total RNA was isolated from tissues with RNeasy Mini kits (QIAGEN) according to the manufacturer's instructions. Complementary DNA (cDNA) was synthesised from 500 ng of total RNA using random hexamer primers and SuperScript III Reverse Transcriptase (Invitrogen, Carlsbad, Calif., USA).

Real-time quantitative PCR analysis of relative TMCO3 expression levels: Quantitative real-time PCR (qRT-PCR) was performed using the StepOne Real Time PCR System (Applied Biosystems, Foster City, Calif., USA). mRNA expression levels were measured using TaqMan probes specific for TMCO3 (Hs01015362_ml, TaqMan Gene Expression Assays, Life Technologies, Carlsbad, Calif., USA), and TMCO3 expression was normalised to that of GAPDH (Hs02758991_gl, TaqMan Gene Expression Assays, Life Technologies). Expression levels were analysed using StepOne Software v2.1 (Applied Biosystems). The relative expression level of each mRNA was determined using the ΔΔCt method. Upregulated TMCO3 relative expression was determined as the ratio of cancerous tissue and the adjacent normal mucosa. All assays were performed in duplicate.

Real-time quantitative PCR analysis of relative sXBP1, ATF3, ATF4, CHOP and TFDP1 expression levels: Quantitative real-time PCR (qRT-PCR) was performed using the StepOne Real Time PCR System (Applied Biosystems) for the analyses of sXBP1, ATF3, ATF4, CHOP and TFDP1. mRNA expression levels were measured using Power SYBR Green Master Mix (4368577, Life Technologies). Primer sequence is shown in supplementary data (Supplementary Table 2). Expression levels were analysed using StepOne Software v2.1 (Applied Biosystems). The relative expression level of each mRNA was determined using the ΔΔCt method.

Supplementary Table 2
Primer setting of PCR

| qRT-PCR using cDNA | |
|---|---|
| Gene | Primer sequence |
| sXBP1 | Forward: CTGAGTCCGAATCAGGTGCAG [SEQ ID NO. 3]<br>Reverse: ATCCATGGGGAGATGTTCTGG [SEQ ID NO. 4] |
| ATF | Forward: GCCGAAACAAGAAGAAGGAGA [SEQ ID NO. 5]<br>Reverse: TCGTTCTTGAGCTCCTCAATC [SEQ ID NO. 6] |
| ATF4 | Forward: GTTCTCCAGCGACAAGGCTA [SEQ ID NO. 7]<br>Reverse: ATCCTGCTTGCTGTTGTTGG [SEQ ID NO. 8] |
| CHOP | Forward: AGAACCAGGAAACGGAAACAGA [SEQ ID NO. 9]<br>Reverse: TCTCCTTCATGCGCTGCTTT [SEQ ID NO. 10] |
| TFDP1 | Forward: ACACCCCCAGCACTCACTTT [SEQ ID NO. 11]<br>Reverse: GGCCCTTGCCATTCTTCTCT [SEQ ID NO. 12] |
| GAPDH | Forward: CTGCACCACCAACTGCTTAG [SEQ ID NO. 13]<br>Reverse: GTCTTCTGGGTGGCAGTGAT [SEQ ID NO. 14] |
| PCR using DNA | |
| Gene | Primer sequence |
| CHOP binding site in TMCO3 | Forward: GAGGCCCACGTTCTAACCT [SEQ ID NO. 15]<br>Reverse: CGTTAGGAGTCACAGGAGGG [SEQ ID NO. 16] |

Immunohistochemistry: Paraffin embedded sections were deparaffinised by xylene and ethanol. After the elimination of endogenous peroxidase activity by H2O2 and antigen retrieval (autoclave 121° C., 15 minutes), slides were incubated with ainti-TMCO3 antibody (ab154581, abcam, 1:400 dilution) for 1 hour. After the reaction of first antibody, slides were stained with EnVision+Dual Link Kit (DAKO, Carpinteria, Calif., USA) and haematoxylin.

Cell lines for in vitro analysis: The CRC cell lines SW480 and HCT116 CRC cell lines were purchased from the American Type Culture Collection (ATCC, Rockville, Md., USA). All cell lines were cultured according to the manufacturer's specifications. Every few months, all cell lines were tested and authenticated using a panel of genetic and epigenetic markers. These cell lines were maintained in Iscove's Modified Dulbecco's Medium (Invitrogen) containing 10% foetal bovine serum and 1% penicillin-streptomycin at 37° C. in a humidified 5% CO2 atmosphere.

Small interfering RNA transfection: TMCO3-specific validated locked nucleic acid (LNA)-modified Silencer Select siRNA (siTMCO3; Silencer Select Validated siRNA, s29960, Ambion/Life Technologies) and control siRNA (siControl; Silencer Select Negative Control #1 siRNA, 4390843, Ambion) were used for the effective knock down of each gene and prevention of off-target effects by the sense strand. All experiments were performed by forward transfection according to manufacturer's protocol. In brief, a mixture of Optimem I (Invitrogen), Lipofectamine RNAiMAX Transfection Reagent (Thermo Fisher Scientific) and siRNA oligonucleotides (50 nM) was added to seeded cells. Cells were incubated in culture media for 48 h after transfection prior to harvesting for analyses.

Western blotting: Western immunoblotting experiments were performed as described previously. In brief, cells were lysed using 500 µL of 1×SDS sample buffer containing β-mercaptoethanol, and electrophoresis was performed. Anti-TMCO3 antibody (ab154581, abcam, 1:5000 dilution), Anti-c-Myc antibody (sc-40, Santa Cruz Biotechnology, 1:250 dilution), Anti-Cyclin D1 (sc-8396, Santa Cruz Biotechnology, 1:250 dilution), Anti-Cyclin E (sc-247, Santa Cruz Biotechnology, 1:250 dilution), Anti-IRE1α (#3294, Cell Signaling Technology, 1:1000 dilution), Anti-Bip (#3177, Cell Signaling Technology, 1:1000 dilution), Anti-CHOP (#2895, Cell Signaling Technology, 1:1000 dilution) were used for the staining of target gene, and anti-β-actin antibody (A5441, Sigma, 1:5000 dilution) was used as reference. The bands were visualized using G: Box (Syngene, Frederick, Md., USA).

MTT assay: An MTT (3-(4,5-dimethylthiazol-2-yl)-2,5-diphenyltetrazolium bromide) assay (Sigma-Aldrich Corp., St. Louis, Mo., USA) was used to analyse cellular viability and proliferation. First, 1000 cells were seeded into each well of a 96-well plate and cultured for 1, 2, 3 and 4 days each. Next, 10 µl of MTT solution was added to each well, and incubated for 2 hours. After the lysis step using Dimethyl sulfoxide, the absorbance at 570 nm was calculated using an Infinite 200 PRO plate reader (TECAN, Mannedorf, Switzerland) every day for 4 days.

Colony formation assay: A total of 500 cells transfected with siTMCO3 or siControl were seeded into 6-well plates and cultured for 10 days in a humidified CO2 incubator at 37° C. The numbers of colonies containing >50 cells were counted using GeneTools image analysis software (Syngene, Frederick, Md., USA).

Invasion assay: The invasiveness of cancer cells was evaluated using BioCoat Matrigel Invasion Chambers (CORNING, Tewksbury, Mass., USA). A total of 5×105 cells transfected with siTMCO3 or siControl were seeded into the invasion and control chambers in serum-free medium. The chambers were incubated for 48 h at 37° C. prior to fixing and staining the membranes with the Diff-Quick Stain-3 Step Set (Richard Allan Scientific, Kalamazoo, Mich., USA). The number of cells that had invaded to the underside of the membrane was then determined.

Apoptosis assay: Muse Annexin V and Dead Cell Assay Kit (MCH100105, EMD Millipore, Billerica, Mass., USA) was used to quantify apoptotic cells according to the manufacturer's specifications. 100 µl of cell suspension were loaded into the 1.5 ml tube with 100 µl of the Muse Annexin V & Dead Cell Reagent. After the incubation for 20 minutes, cells were analysed using Muse Cell Analyzer (Millipore, Billerica, Mass., USA). Annexin V positive cells were determined as apoptotic cells. Active Caspase-3 was analysed as apoptosis marker using CaspGLOW Fluorescein Active Caspase-3 Staining Kit (88-7004-42, eBioscience, San Diego, Calif., USA) according to the manufacturer's specifications.

Acidic culture model: At first Cells were cultured for 3 days in the same condition to induce endogenous acidification. After that, cells in acidic group were cultured for additional 3 days in the same medium with enough nutrition supply. On the other hand, cells in control group were cultured in normal pH medium changed once a day to keep normal pH for additional 3 days. pH of culture media was confirmed in the beginning and end of experiment using pH meter.

Intracellular pH calculation: pHrodo Green AM Intracellular pH Indicator (P35373, Thermo Fisher Scientific, Waltham, Mass., USA) was used to calculate intracellular pH according to the manufacturer's specifications. Cells were incubated with pHrodo AM Ester staining solution for 30 min. After that, intracellular fluorescent signal was analysed using flow cytometry and FlowJo (FlowJo, FlowJo, Ashland, Oreg., USA).

Xenograft model: Male athymic nude mice were obtained from Harlan Laboratories (Houston, Tex., USA) at 5 weeks of age and kept under controlled conditions (12 h light and dark cycles). The animal protocol was approved by the Institutional Animal Care and Use Committee of the Baylor Research Institute. Xenograft tumours were generated using HCT116 cell line with TMCO3 siRNA or its controls. These cancer cells were suspended in PBS and Matrigel (Corning) (1:1 ratio) and 3×106 cells were subcutaneously injected into the abdominal flanks of each mice. Eleven mice were used in each group. The mice were monitored for twelve days following injection, and subcutaneous tumours were measured every two days. Tumour size was measured using callipers and the volume was calculated using the following formula: (3.14*L*W*H)/6 where L represents length, W width, and H height. At twelve days post-injection, all animals were sacrificed. Tumour samples were dissected and stored in RNA-later (Sigma-Aldrich), and the expression of TMCO3 in xenograft tissues was confirmed by qRT-PCR.

Chromatin Immunoprecipitation assay (Chip assay): High-Sensitivity ChIP Kit (ab185913, abcam) was used to analyse protein-DNA interaction by Chip assay according to the manufacturer's specifications. 3×106 HCT116 cells were collected and fixed with 1% formaldehyde. After the shearing of DNA by sonication, chromatin was reacted with anti-CHOP antibody (#2895, Cell Signaling Technology, 0.8 µm/well), anti-RNA Polymerase II antibody (0.8 µm/well) as positive control and Non-immune IgG (0.8 µm/well) as negative control for overnight. After the collection of captured chromatin-DNA complex, DNA was purified. Binding site of transcription factor was estimated using TFBIND. Target DNA sequence was detected by PCR followed by electrophoresis. Primer sequence is shown in supplementary data (Supplementary Table 2).

Enhancer analyses using FANTOM5 database and UCSC genome browser: Original data including enhancer activity was obtained from FANTOM5 database; Expression (TPM and RLE normalized) matrix of enhancers across all considered FANTOM libraries (http://enhancer.binfku.dk/Predefined_tracks.html). The formula of relative activation level of enhancer is as below: [(CACO2–colon adult donor1)+(COLO320–colon adult donor1)]/2+[(MKN1–stomach fetal donor1)+(MKN45–stomach fetal donor1)]/2+[(MCF7–breast adult donor1)+(MDA-MB-453–breast adult donor1)]/2+[(A549–lung right lower lobe adult donor1)+(PC-14–lung right lower lobe adult donor1)]/2+[(DU145–Prostate Epithelial Cells (polarized) donor1)+(PC-3–Prostate Epithelial Cells (polarized) donor1)]/2+[(COL0679–Melanocyte light donor1)+(G361–Melanocyte light donor1)]/2. Information of ChIA-PET was obtained from UCSC genome browser.

Methylation analyses: The information of promoter methylation in TMCO3 gene was obtained from the human pan-cancer methylation database, MethHC.

Structure prediction of TMCO3: Sequence of amino acid was obtained from UCSC genome browser. SACS TMHMM Transmembrane Prediction was used to predict transmembrane segments in a protein. Swiss model powered by Biozentrum, University of Basel was used to predict 3D structure of TMCO3 protein.

Statistical analyses: Results are expressed as means±standard errors (SE). JMP software (ver. 10.0, SAS Institute Inc., Cary, N.C., USA) was used to perform the statistical analyses. The Wilcoxon rank sum test was used to compare continuous variables, and Fisher's exact test was used to analyse categorical variables. Disease-free survival (DFS) was measured from the operation date to the date of recurrence or cancer related death. The Kaplan-Meier method with the log-rank test was used to estimate distributions of DFS in each patient group through univariate analyses. Cut-off value of TMCO3 high expression was determined as the level which can eliminate 75% of normal area using 15 matched normal-cancer pairs in TCGA database with partially matched cancer-normal tissues. In cohort2 with absolutely matched cancer-normal tissues, TMCO3 high group was determined as patients whose cancerous tissue showed higher TMCO3 expression than adjacent normal mucosa. Cox proportional hazard models were used to calculate hazard ratios (HR) with corresponding 95% confidence intervals (CI) for each group in a univariate and multivariate analysis. All calculated P values are two-sided, and a P value of <0.05 was considered to indicate statistical significance.

B. Results

1. Enhancer in TMCO3 is Activated in Many Types of Cancer

Figure 7A:
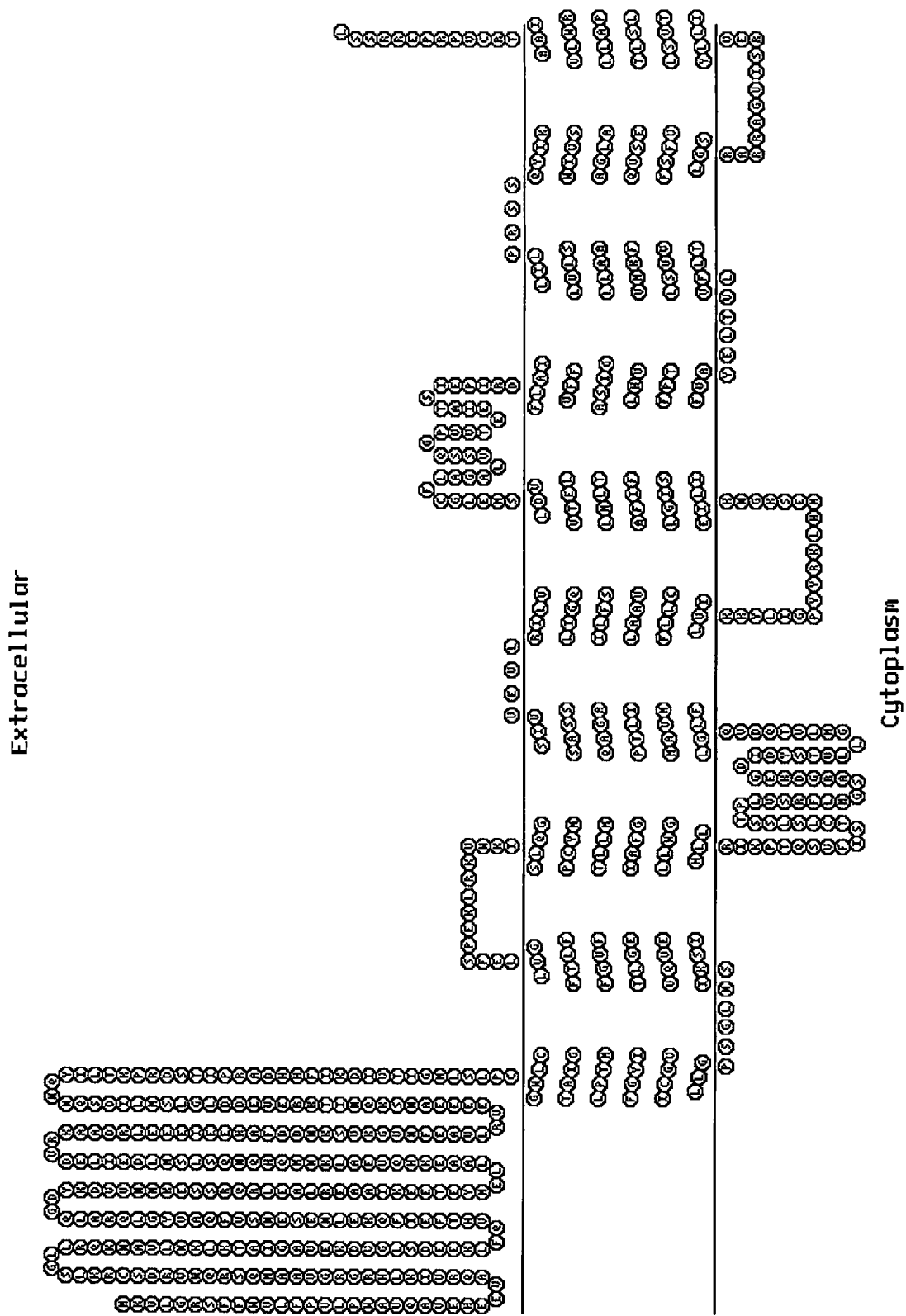
FIGS. 7A-B—Enhancer activity and structure of TMCO3. TMCO3 has a $Na^+$-$H^+$ antiporter domain including 10 transmembrane domains [SEQ ID NO. 2].
Figures 7B, 8A, 8B:
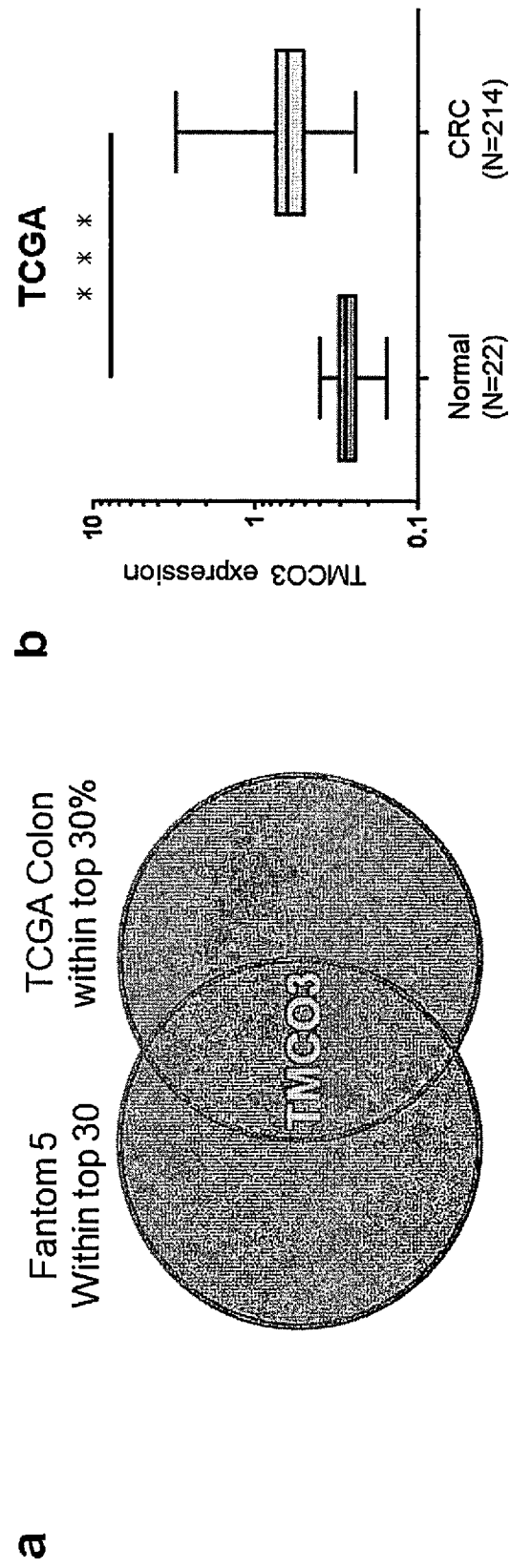
FIGS. 8A-H—TMCO3 expression and clinicopathological features: (a) Patients in TCGA were categorised into 2 subgroups; TMCO3 high or low group. Cut-off value of TMCO3 high expression was determined as the level which can eliminate most of normal using 15 matched normal-cancer pairs. 75% of patients was categorised into TMCO3 high group and 25% was categorized into TMCO3 low group. (b) TMCO3 was upregulated in CRC in stage dependent manner in TCGA. (c) The TMCO3 expression level was significantly higher in Stage III or IV CRC lesions relative to Stage I or II CRC lesions (P=0.03) in TCGA. (d) The TMCO3 expression level was also higher in lymph node metastasis-positive CRC lesions than in negative CRC lesions (P=0.01) in TCGA. (e) The high-TMCO3 group had worse DFS than the low-TMCO3 group (P=0.02) in TCGA. (f) High TMCO3 group showed worse DFS (P<0.01) in cohort 2.

Cancer specific enhancer activation level is analysed in FANTOM5 database. Enhancer in TMCO3 gene is 23th activated enhancer in 43011 enhancers in many cancer types including colorectal cancer, gastric cancer, breast cancer, lung cancer and prostate cancer. TMCO3 gene has enhancer element between exon 1 and exon 2, which was detected in chr13:114147699-114148153. Additionally, TMCO3 has a Na+-H+ antiporter domain including 10 transmembrane domains (FIG. 7A-B). Immunofluorescence cell staining showed that TMCO3 was located in cellular membrane (data not shown). These results suggest that TMCO3 is a potential ion exchanger with oncogenic enhancer activity.

2. TMCO3 is Upregulated in Many Types of Cancer: Testing Set

Figures 14A, 14B:
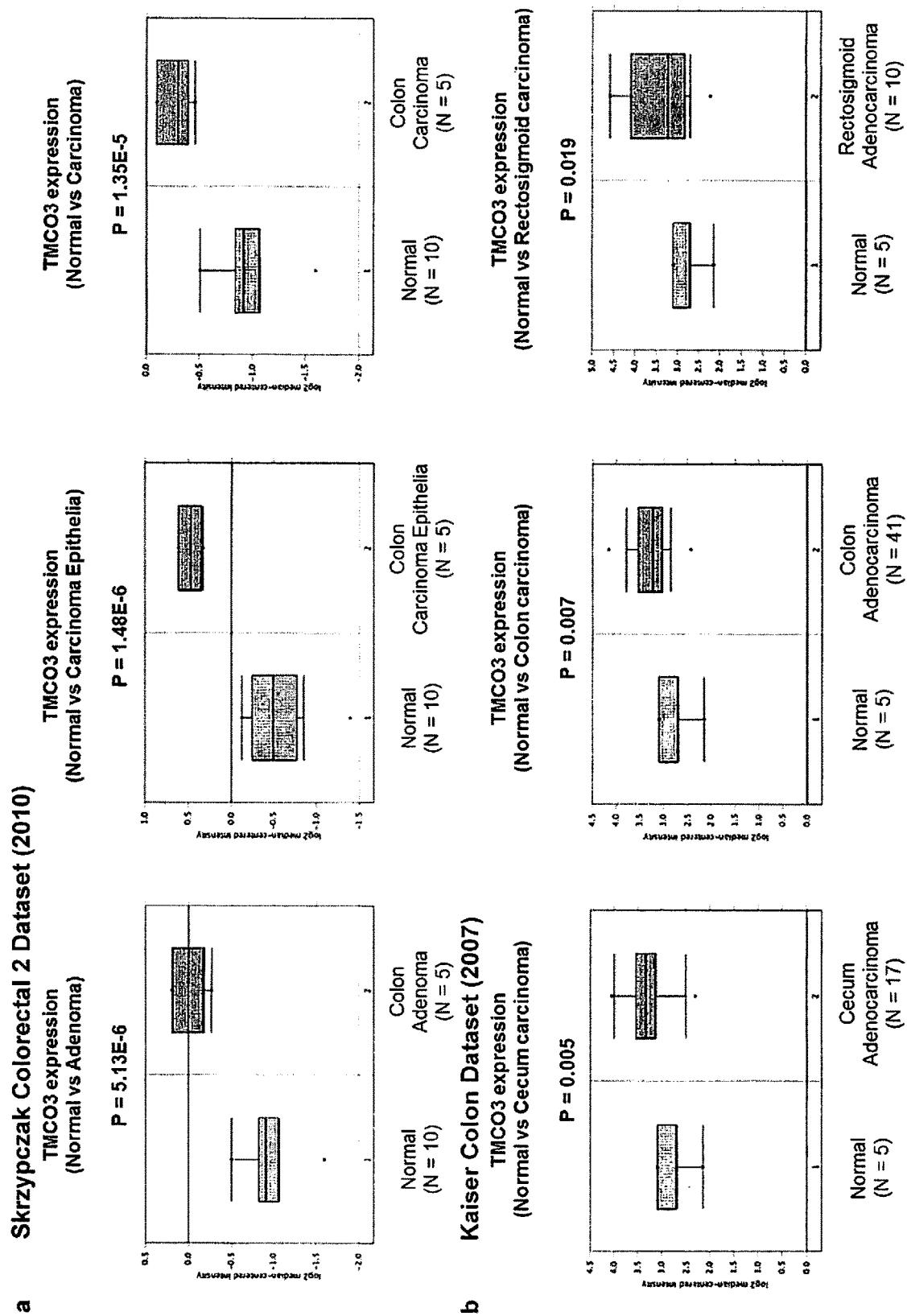
FIGS. 14A-B: TMCO3 expression in CRC: (a) TMCO3 was upregulated in colorectal neoplastic lesions compared with normal mucosa in Skrzypczak Colorectal 2 Dataset (normal vs adenoma: P=5.13E-6, normal vs colon carcinoma epithelia: P=1.48E-6, normal vs colon carcinoma: P=1.35E-5). (b) TMCO3 was upregulated in colorectal neoplastic lesions compared with normal mucosa in Kaiser Colon Dataset (normal vs cecum carcinoma: P=0.005, normal vs colon carcinoma: P=0.007, normal vs rectosigmoid carcinoma: P=0.019).

At first, TMCO3 expression levels in Oncomine database were analyzied. TMCO3 was upregulated in many types of cancers. In two dataset, Skrzypczak Colorectal 2 Dataset (normal vs adenoma: P=5.13E-6, normal vs colon carcinoma epithelia: P=1.48E-6, normal vs colon carcinoma: P=1.35E-5) and Kaiser Colon Dataset (normal vs cecum carcinoma: P=0.005, normal vs colon carcinoma: P=0.007, normal vs rectosigmoid carcinoma: P=0.019), TMCO3 was upregulated in colorectal neoplastic lesions compared with normal mucosa (FIG. 14A-C). This means that TMCO3 may play a significant role in carcinogenesis.

3. TMCO3 is Upregulated in CRC and Results in Worse DFS in TCGA Cohort

Figures 8C, 8D, 8E, 8F:
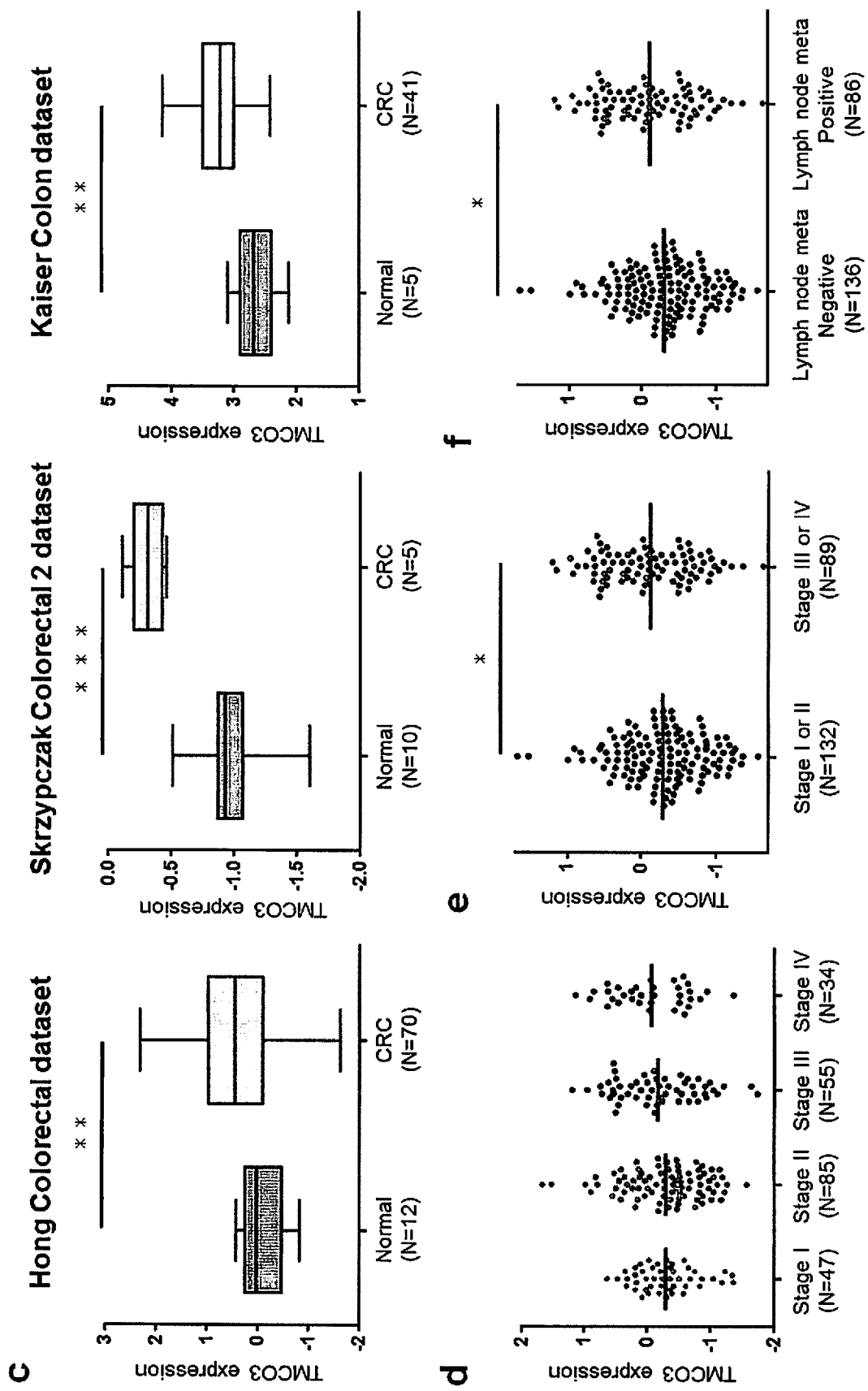
Figures 8G, 8H:
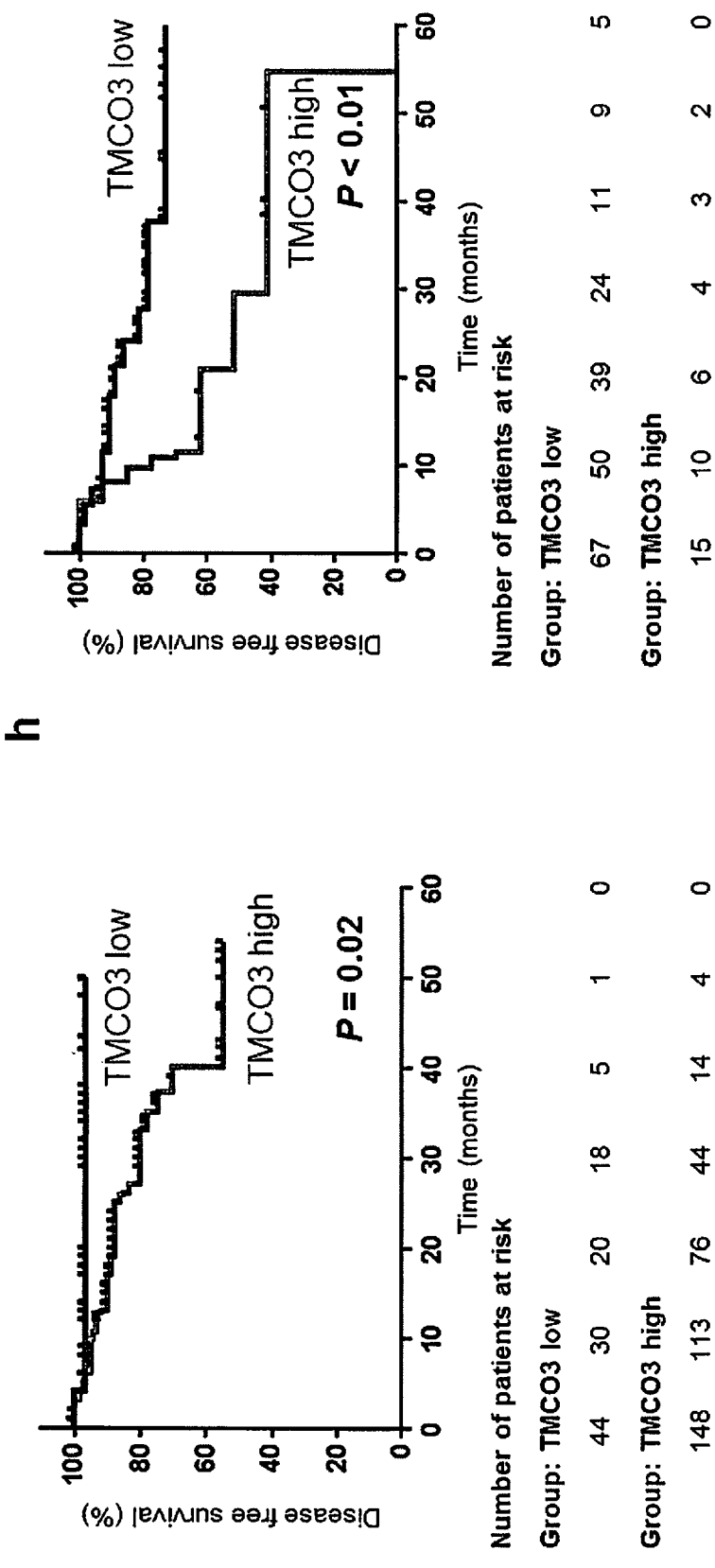

In order to determine whether TMCO3 expression is correlated with clinicopathological features in CRC, TMCO3 expression levels in TCGA database were analyzed. At first we categorised patients into 2 subgroups; TMCO3 high or low group. Cut-off value of TMCO3 high expression was determined as the level which can eliminate normal using 15 matched normal-cancer pairs. 75% of patients was categorised into TMCO3 high group and 25% was categorized into TMCO3 low group (FIG. 8A). TMCO3 was upregulated in CRC in stage dependent manner (FIG. 8B). The TMCO3 expression level was significantly higher in Stage III or IV CRC lesions relative to Stage I or II CRC lesions (P=0.03) (FIG. 8C). The TMCO3 expression level was also higher in lymph node metastasis-positive CRC lesions than in negative CRC lesions (P=0.01) (FIG. 8D). Collectively these data indicate that TMCO3 may act as oncogene.

Next, relationship between TMCO3 expression and DFS was analysed. The high-TMCO3 group had worse DFS than the low-TMCO3 group (P=0.02) (FIG. 8E).

Figure 15A:
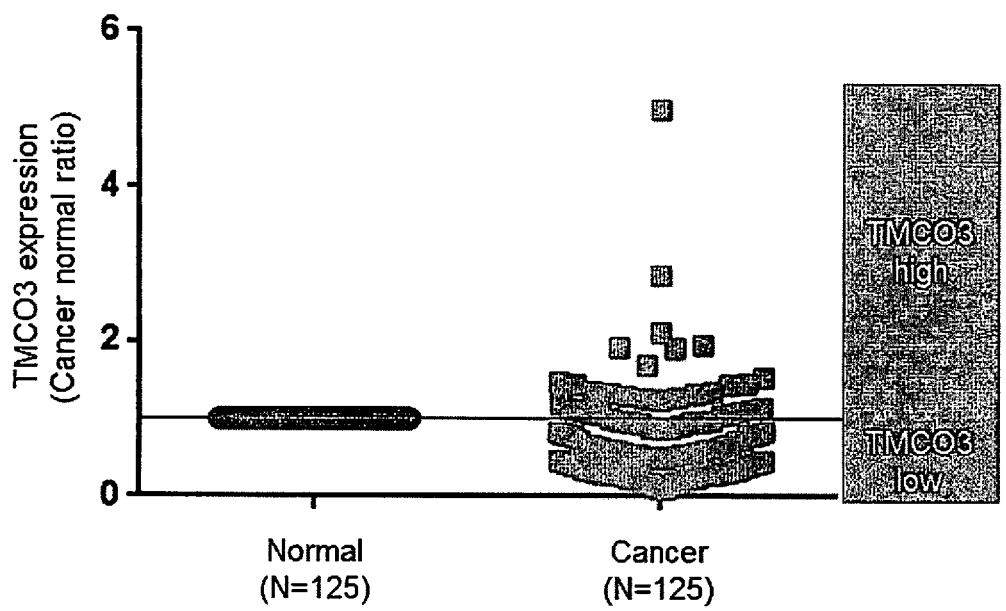
FIG. 15A-C: (a) TMCO3 expression in cohort 2 (b) TMCO3 was upregulated in CRC in stage dependent manner. (c) The high TMCO3 group had a significantly greater distant metastasis positive rate than the low-TMCO3 group (P=0.04).
Figure 15B:
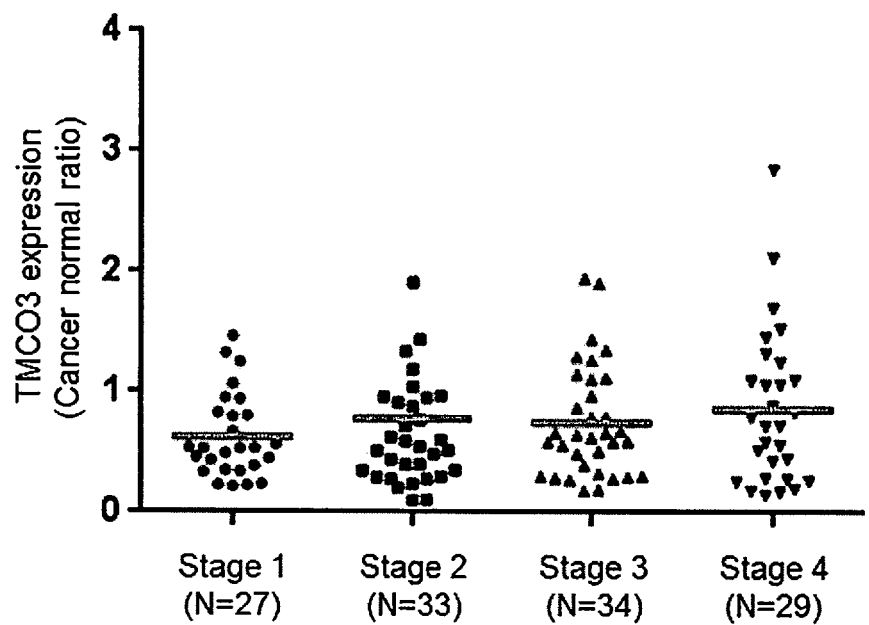
Figure 15C:
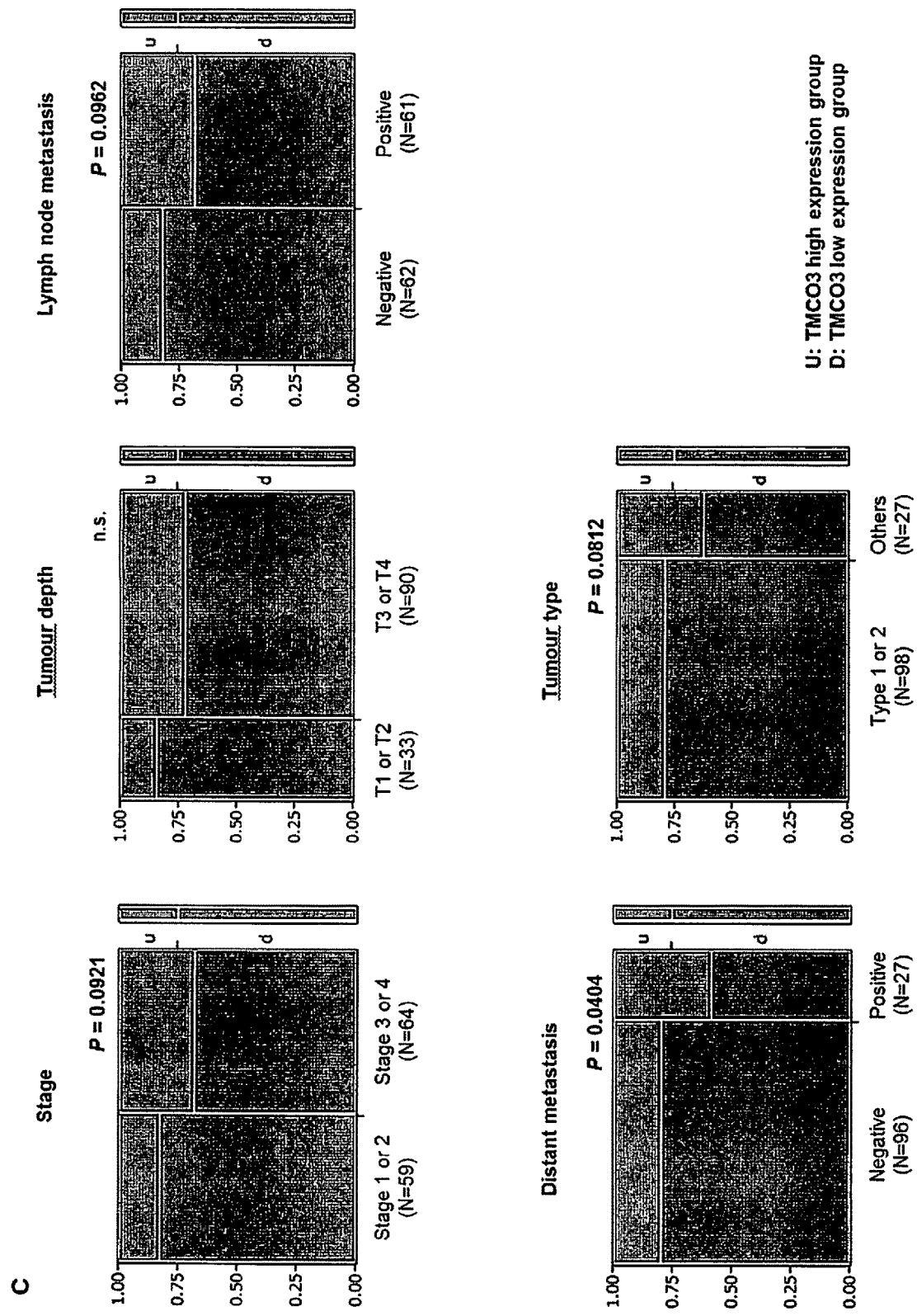

4. High TMCO3 Group Showed Worse Clinicopathological Status in Cohort2 CRC Patients The original cohort 2 was analyzed. TMCO3 high group was determined as patients whose cancerous tissue showed higher TMCO3 expression than adjacent normal mucosa. TMCO3 was upregulated in CRC in stage dependent manner (FIG. 15A). Additionally the relationship between TMCO3 expression level and clinicopathological features was analysed. The high TMCO3 group had a significantly greater distant metastasis positive rate than the low-TMCO3 group (P=0.04) (FIG. 15B). High TMCO3 group showed worse DFS (P<0.01) in Kaplan-Meyer analysis (FIG. 8F).

5. TMCO3 Expression Level is an Independent Prognostic Factor of DFS in Stage II and III CRC Patients in TCGA and Cohort 2

From the clinical viewpoint, the information about recurrence risk is useful to determine the eligibility to adjuvant chemotherapy because high risk Stage II and III need chemotherapy after the surgery to reduce the recurrent risk. It was analysed whether TMCO3 expression level can be a good biomarker to estimate the recurrent risk in Stage II and III CRC patients using DFS information in both cohorts. We analysed two cohorts using Cox proportional hazard model. In TCGA cohort, Cox proportional hazard analysis demonstrated that high-TMCO3 expression was an independent prognostic factor in patients with Stage II or III CRC (P=0.05) (Table 1). In cohort 2, the same result was obtained (P=0.01), suggesting that the expression level of TMCO3 can be an independent risk marker in post-operative Stage II and III CRC patients (Table 2). This information will be helpful to determine patient's eligibility to adjuvant chemotherapy.

TABLE 1

Univariate and multivariate analysis of outcome (DFS) predictors in cohort 1 (TCGA) with Stage II or III CRCs

| Characteristic | Univariate | | | Multivariate | | |
|---|---|---|---|---|---|---|
| | HR | 95% CI | P | HR | 95% CI | P |
| Tumour depth | | | | | | |
| T3 or T4/T1 or T2 | 1.23 | 0.38-7.50 | 0.77 | 0.93 | 0.15-17.88 | 0.95 |
| Lymph node metastasis | | | | | | |
| Positive/Negative | 1.45 | 0.88-2.40 | 0.15 | 1.28 | 0.39-3.86 | 0.65 |
| TMCO3 | | | | | | |
| High/Low | 5.10 | 1.01-92.62 | 0.05 | 5.00 | 0.98-91.05 | 0.05 |

TABLE 2

Univariate and multivariate analysis of outcome (DFS) predictors in cohort 2 with Stage II or III CRCs

| Characteristic | Univariate | | | Multivariate | | |
|---|---|---|---|---|---|---|
| | HR | 95% CI | P | HR | 95% CI | P |
| Tumour depth | | | | | | |
| T3 or T4/T1 or T2 | 9.30 | 1.93-167.10 | <0.01 | 2.91 | 0.50-55.26 | 0.27 |
| Lymph node metastasis | | | | | | |
| Positive/Negative | 7.72 | 2.97-23.83 | <0.0001 | 5.73 | 2.07-18.84 | 0.001 |
| TMCO3 | | | | | | |
| High/Low | 3.73 | 1.44-9.27 | 0.01 | 3.59 | 1.34-9.31 | 0.01 |

Figures 9A, 9B, 9C, 9D:
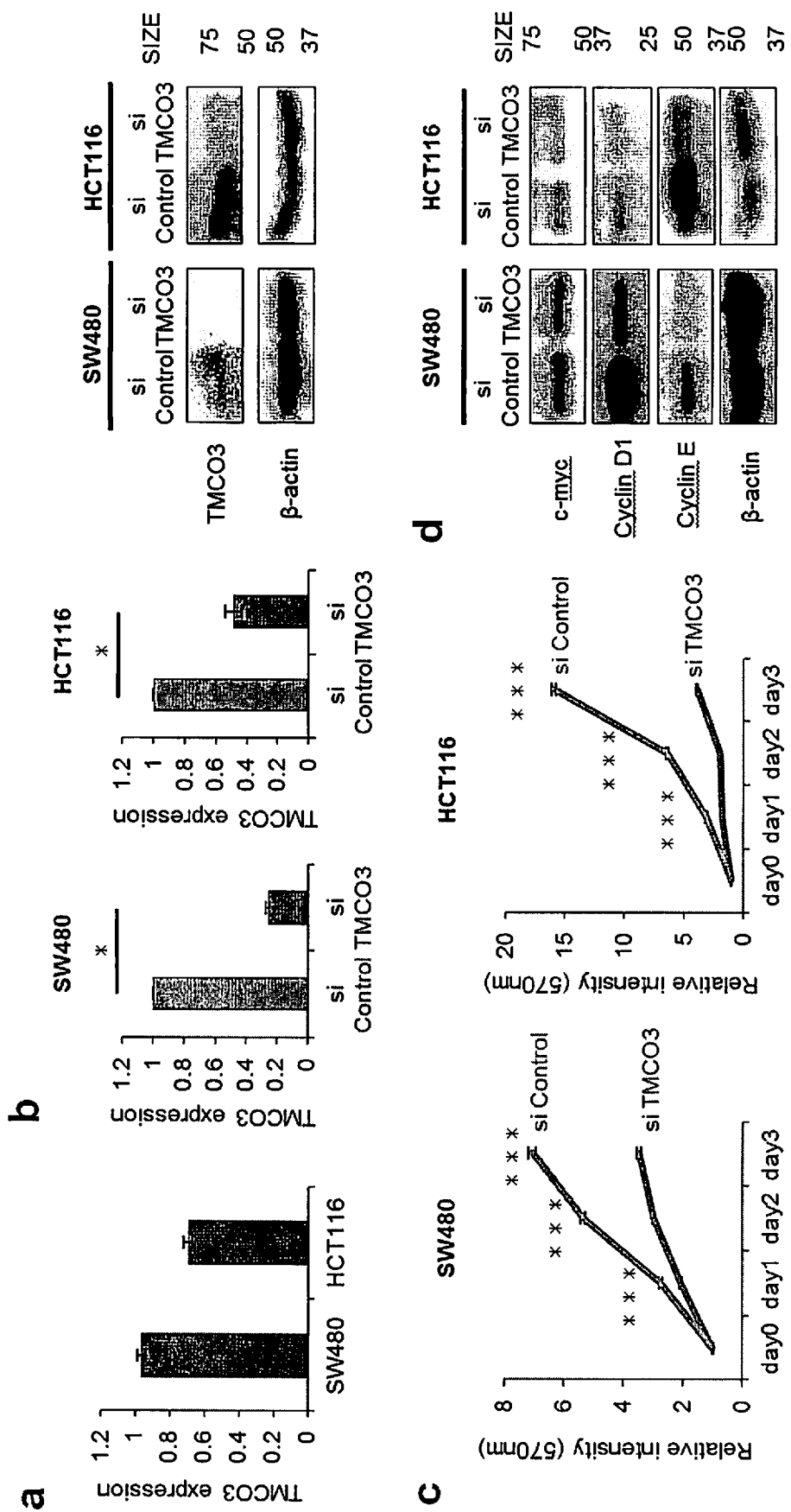
FIGS. 9A-G—in vitro analyses of TMCO3: (a) TMCO3 expression was confirmed in SW480 (Microsatellite stable CRC, KRAS G12V mutant) and HCT116 (Microsatellite instable CRC, KRAS G13V mutant). (b) siRNA knockdown efficiency was confirmed using qRT-PCR and Western blotting. Both CRC cell lines showed significant suppression of TMCO3 protein expression following TMCO3 knockdown. (c) c-Myc, Cyclin D1 and Cyclin E were all downregulated in siTMCO3 cells in SW480 and HCT116 cell lines. (d) SW480 and HCT116 cells transfected with siTMCO3 exhibited remarkably suppressed proliferation, compared with siControl-transfected cells in MTT assay. (e) SW480 and HCT116 cells transfected with siTMCO3 produced a significantly lower number of colonies, compared with siControl-transfected cells. (f) siTMCO3 transfection resulted in significantly decreased invasiveness relative to siControl-transfected cells in both the SW480 and HCT116 CRC cell lines. (g) siTMCO3 transfection resulted in significantly decreased migration relative to siControl-transfected cells in both the SW480 and HCT116 CRC cell lines.

6. Inhibition of TMCO3 Results in Decreased Cell Proliferation, Attenuated Tumorigenicity, and Lower Invasive Potential in Colorectal Cancer Cells To determine whether TMCO3 modulates biological characteristics of CRC cells, TMCO3 expression was transiently knocked-down in SW480 and HCT116 cell lines via siRNA transfection. At first, TMCO3 expression in SW480 (Microsatellite stable CRC, KRAS G12V mutant) and HCT116 (Microsatellite instable CRC, KRAS G13V mutant) was confirmed using qRT-PCR (FIG. 9A). Each cell lines showed effective reduction in TMCO3 mRNA by siTMCO3 knockdown. This knockdown efficiency was further validated at protein level using western blotting. Both CRC cell lines showed significant suppression of TMCO3 protein expression following TMCO3 knockdown (FIG. 9B).

Next, in order to determine whether downregulation of TMCO3 resulted in suppression of cell proliferation in human cancer cell lines, the expression of key regulator of cell proliferation was analysed using western blotting. c-Myc, Cyclin D1 and Cyclin E were all downregulated in siTMCO3 cells in SW480 and HCT116 cell lines (FIG. 9C). Cell proliferation ability was additionally analysed by MTT assays using siTMCO3 transfected cell lines. In both SW480 and HCT116 cell lines, siTMCO3-transfected cells exhibited remarkably suppressed proliferation, compared with siControl-transfected cells (FIG. 9D). Colony formation assays were then used to evaluate the effect of siTMCO3 on the colony-forming abilities of single cancer cells. SW480 and HCT116 cells transfected with siTMCO3 produced a significantly lower number of colonies, compared with siControl-transfected cells (FIG. 9E).

Figures 9E, 9F, 9G:
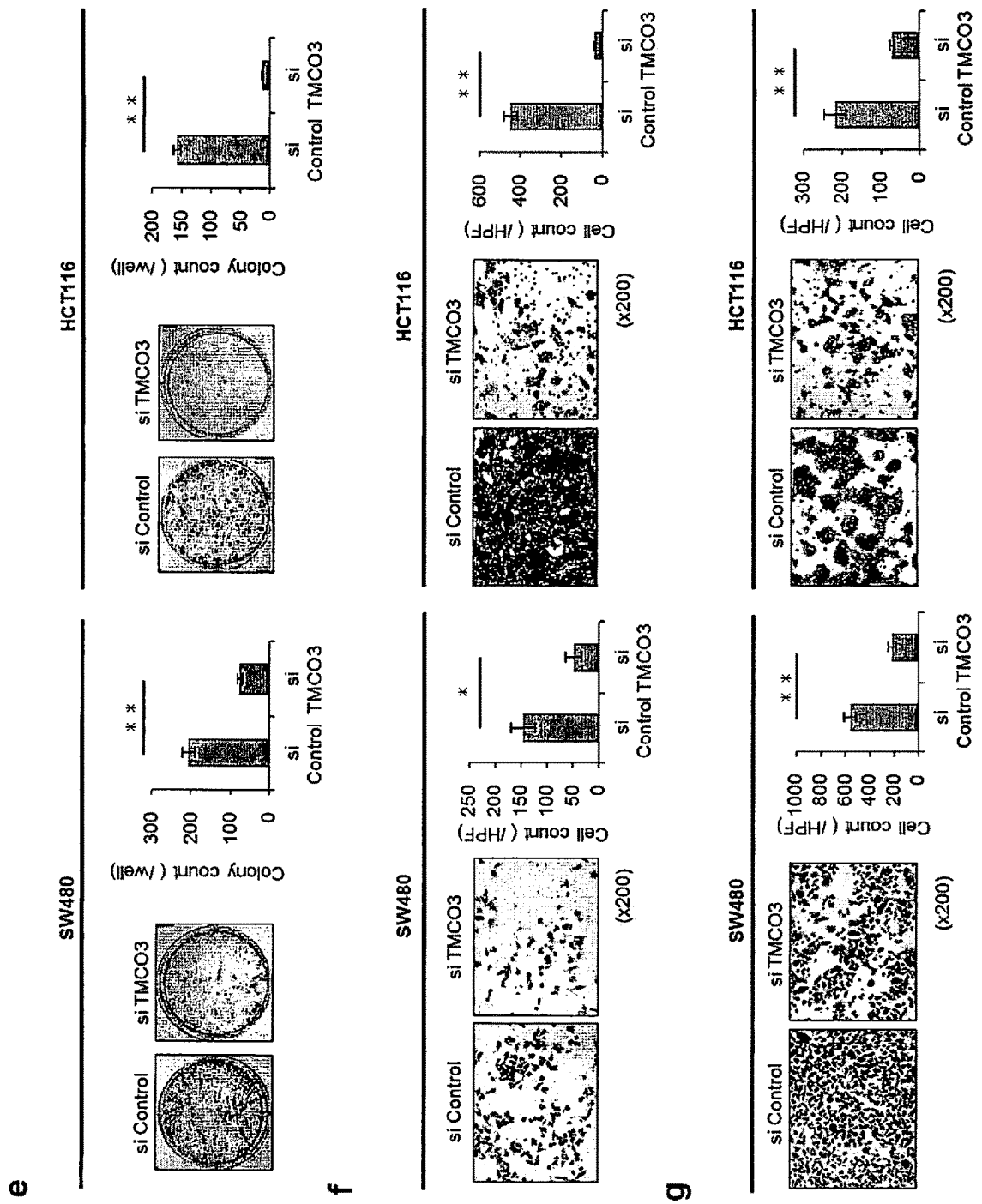

Considering that the clinical data indicated TMCO3 overexpression as a potential risk factor for invasion and corresponding metastasis of CRCs, we investigated whether TMCO3 knockdown inhibits invasive capacity of CRC cells using in vitro trans-well invasion assays. siTMCO3 transfection resulted in significantly decreased invasiveness relative to siControl-transfected cells in both the SW480 and HCT116 CRC cell lines (FIG. 9F). The same tendency was obtained from migration assay (FIG. 9G). Interestingly, the same results were obtained from HCT116 (p53−/−) and HCT116 (p21−/−) cells, suggesting that p53 and p21 are not involved in these phenomenon caused by siTMCO3 (Data not shown).

Figures 10A, 10B:
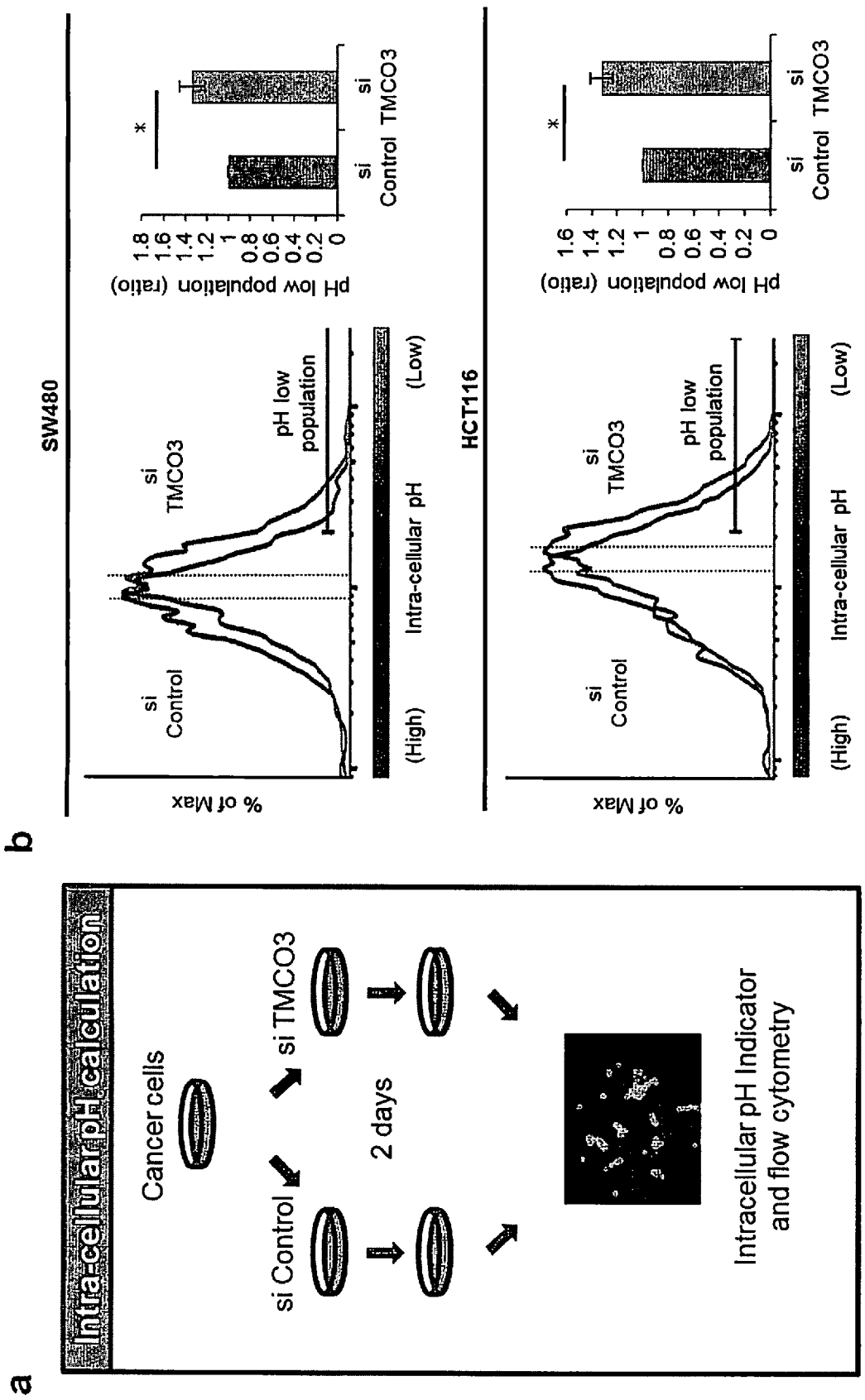

7. Knockdown of TMCO3 Lead to Intracellular Acidification Followed by Induction of Apoptosis Next, intracellular pH level in siTMCO3 CRC cells was analysed using intracellular pH Indicator based on flow cytometry technology because TMCO3 is a potential cation—H+ antiporter (FIG. 10A). Cancer cell generate much lactate because of Warburg effect and it was hypothesised that si RNA knockdown of TMCO3 may lead to acidification in intra-cellular environment. In siTMCO3 transfected cells, intra-cellular pH significantly decreased as expected (FIG. 10B). This intracellular acidification finally induces apoptosis. The rate of apoptotic cells appeared to be raised in siTMCO3 cells in both SW480 and HCT116 cell lines (FIG. 10C). Activation of caspase-3 in siTMCO3 cells supports induction of apoptosis in siTMCO3 CRC cells (FIG. 10D). These in vitro analyses showed that TMCO3 has oncogenic potential with intra-cellular pH controller and inactivation of TMCO3 leads to attenuated tumorigenicity because of intracellular acidification and simultaneous apoptosis. These results support oncogenic role of TMCO3 obtained from two clinical cohorts. On the other hand, in non-cancerous WI38 cells, suppression effect of cell proliferation and induction of apoptosis were not so severe compared with that of cancer cells in siTMCO3. This means that the role of TMCO3 is not essential in normal cells because normal cells don't have the potential of Warburg effect (data not shown).

8. TMCO3 Inhibits Xenograft Tumour Growth

To confirm the in vitro findings, xenograft tumours were generated using HCT116 cells transfected with either siTMCO3 or siControl injected 3×106 cells subcutaneously to the flanks nude mice. 10 days following the initial injection, the tumour volume and weight were significantly lower in recipients of siTMCO3-transfected cells, compared with recipients of siControl-transfected cells (FIG. 11A). In order to determine the efficacy of TMCO3 siRNA knockdown, we extracted RNA from the xenograft tumours and evaluated TMCO3 expression by qRT-PCR. TMCO3 expression level was significantly lower in siTMCO3 tumours than in scramble control transfected tumours (FIG. 11B). This in vivo experiment showed completely consistent results with in vitro experiment.

Figure 6:
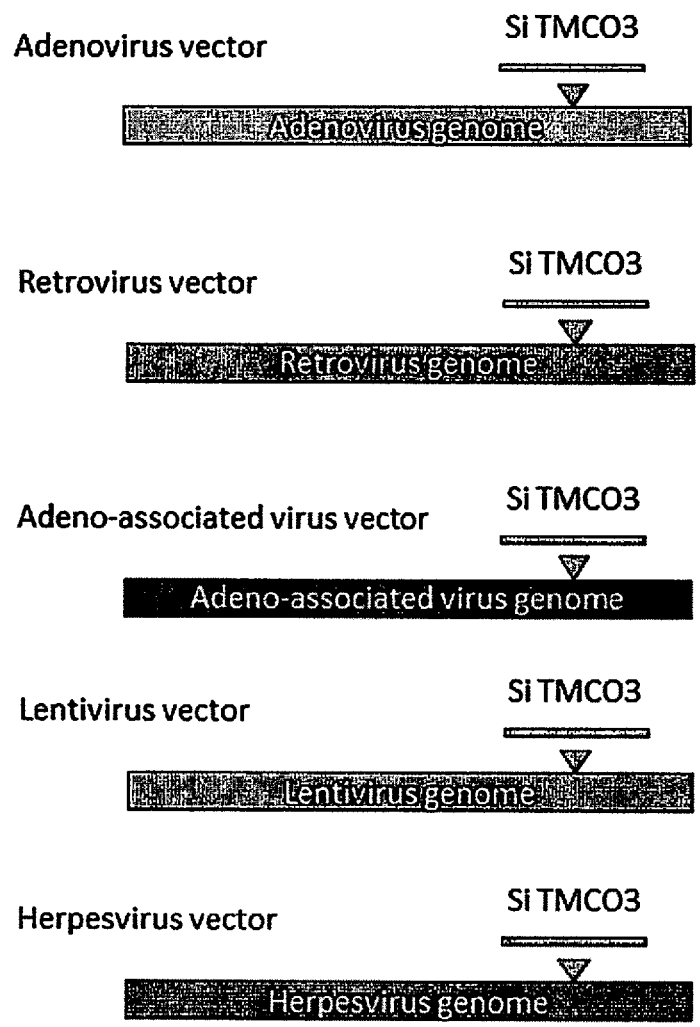
FIG. 6—Establishment of viral vectors for delivery of siRNA against TMCO3 (siTMCO3).
Figures 12A, 12B, 12C, 12D, 12E, 12F, 12G:
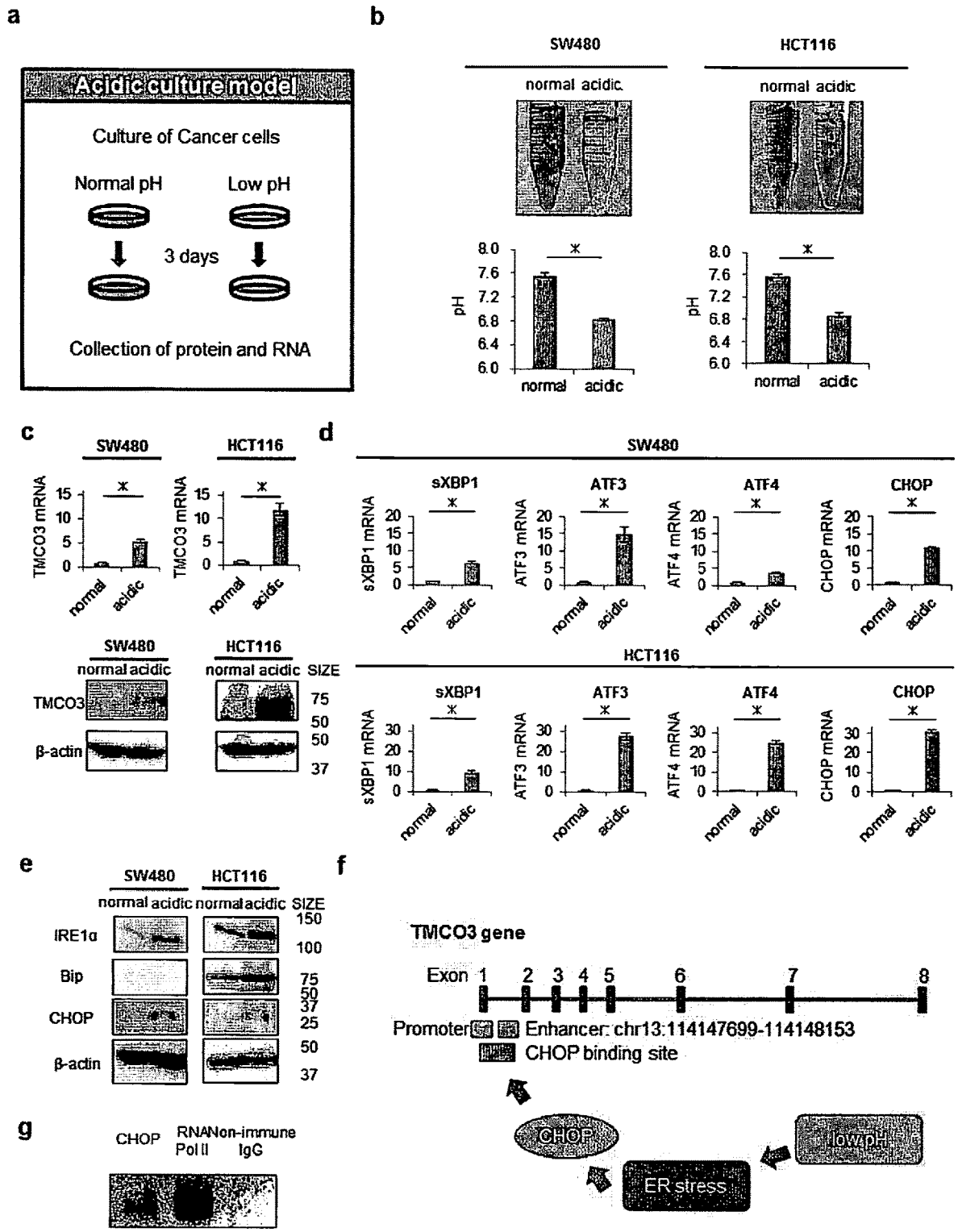
FIGS. 12A-G—TMCO3 overexpression in acidic environment: (a) SW480 and HCT116 cells were kept in acidic medium for 3 days and compared with cells cultured in normal pH medium. (b) pH in acidic medium was kept significantly lower than that of normal medium during this experiment. (c) TMCO3 mRNA expression is up regulated in acidic culture in both SW480 and HCT116 cells. TMCO3 protein expression is also up regulated in acidic culture in both SW480 and HCT116 cells. (d) The key modulators of ER stress including sXBP1, ATF3, ATF4 and CHOP mRNAs were up-regulated. (e) IRE1α, Bip and CHOP protein were upregulated in the western blotting, suggesting that acidic environment induce ER stress in cancer cells. (f) CHOP is a key transcription factor in ER stress and TMCO3 has multiple CHOP binding sites in its promoter-enhancer sequence. (g) CHIP assay showed binding of CHOP to promoter-enhancer sequence in TMCO3.

9. Acidic Environment Induce TMCO3 Overexpression by Means of Endoplasmic Reticulum (ER) Stress In cancerous tissue, pH is often down-regulated mainly because of Warburg effect. The effect of acidic environment in CRC cells was analyzed. SW480 and HCT116 cells were kept in acidic medium for 3 days and compared with cells cultured in normal pH medium (FIG. 12A). pH level in culture medium was checked using pH calculator. pH in acidic medium was kept significantly lower than that of normal medium during this experiment (FIG. 12B). TMCO3 mRNA expression is up regulated in acidic culture in both SW480 and HCT116 cells. TMCO3 protein expression is also up regulated in acidic culture in both cells (FIG. 6C). This upregulation of TMCO3 will be helpful to pump off proton from cytoplasm. In the next step, the overexpression mechanism of TMCO3 was analyzed. Intracellular acidification induces endoplasmic reticulum (ER) stress. The key modulators of ER stress including sXBP1, ATF3, ATF4 and CHOP mRNAs were up-regulated in acidic culture (FIG. 12D). Additionally, in the western blotting, IRE1α, Bip, CHOP were upregulated, suggesting that acidic environment induce ER stress in cancer cells (FIG. 12E). In these molecules, CHOP is a key transcription factor and TMCO3 has its multi-binding sites in its promoter-enhancer sequence (FIG. 12F). CHIP assay showed binding of CHOP to promoter-enhancer sequence in TMCO3, suggesting that CHOP can regulate the activation of TMCO3 gene in acidic environment (FIG. 12G-H).

10. Protein Expression of TMCO3 in Colorectal Cancer and Normal Mucosa

TMCO3 has a transmembrane domain and act as ion exchanger. However, the localization of TMCO3 protein in cancer lesion remains unknown. TMCO3 protein expression was then analysed using public database and our original cohort. At first, Localization of TMCO3 was analysed using the Human Protein Atlas database. TMCO3 was detected in microvilli in normal colon epithelium and this localization was kept in well differentiated adenocarcinoma. However, in the moderate or poor differentiated adenocarcinoma, this localization of TMCO3 was dysregulated and TMCO3 expression was detected in all sides of CRC cells. Dysregulation of the localisation of TMCO3 was also detected in the original cohort (Data not shown). This phenomenon may lead to acidification of CRC microenvironment because cancer cell cannot pump out proton to the lumen side of colon.

11. Enhancer in TMCO3 is a Key Regulator of Oncogenic Transcription Factor TFDP1

Figure 13A:
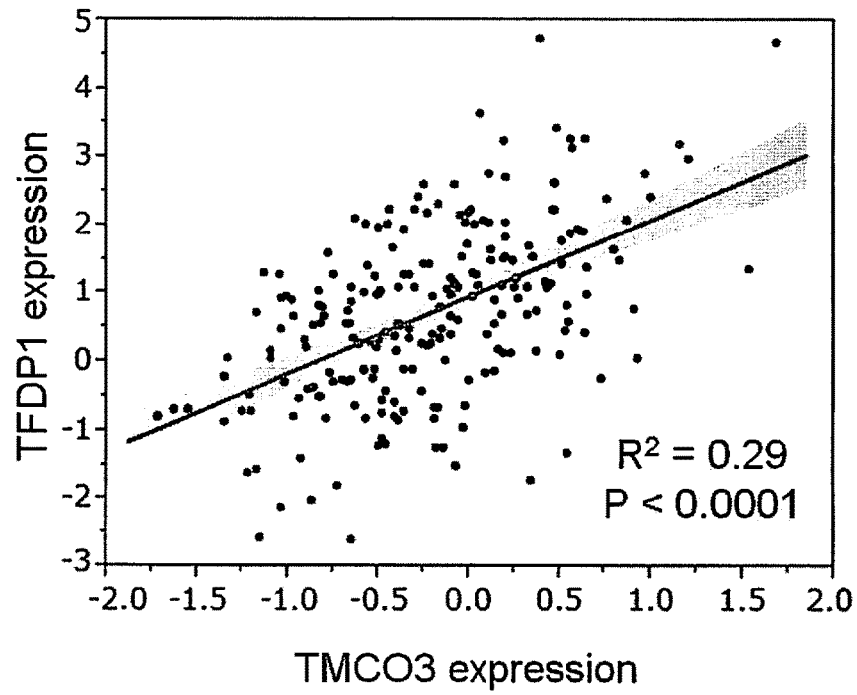
FIGS. 13A-B—Relation between enhancer and target promoter: (a) The expression levels of TMCO3 and TFDP1 have a positive correlation in TCGA database (P<0.0001). (b) The expression of oncogenic transcription factor, TFDP1 is also upregulated in the acidic environment, in which TMCO3 is upregulated.
Figure 13B:
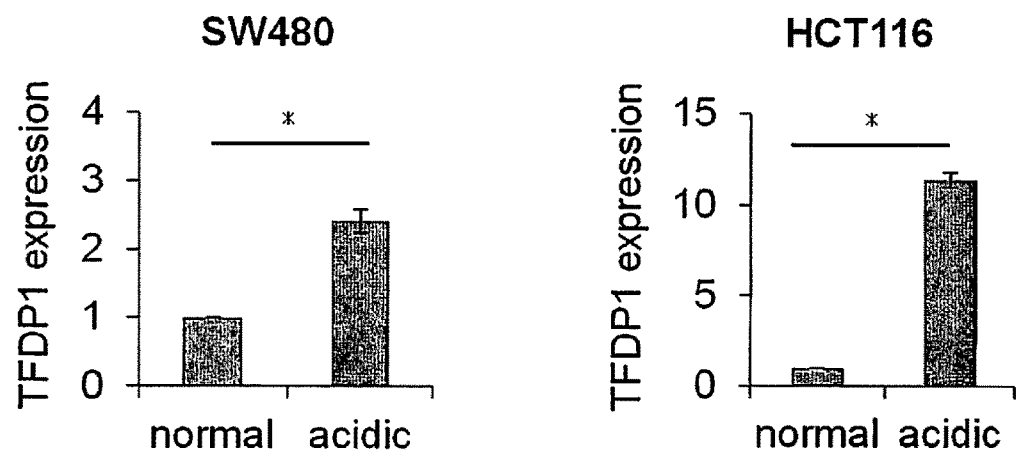
Figure 16A:
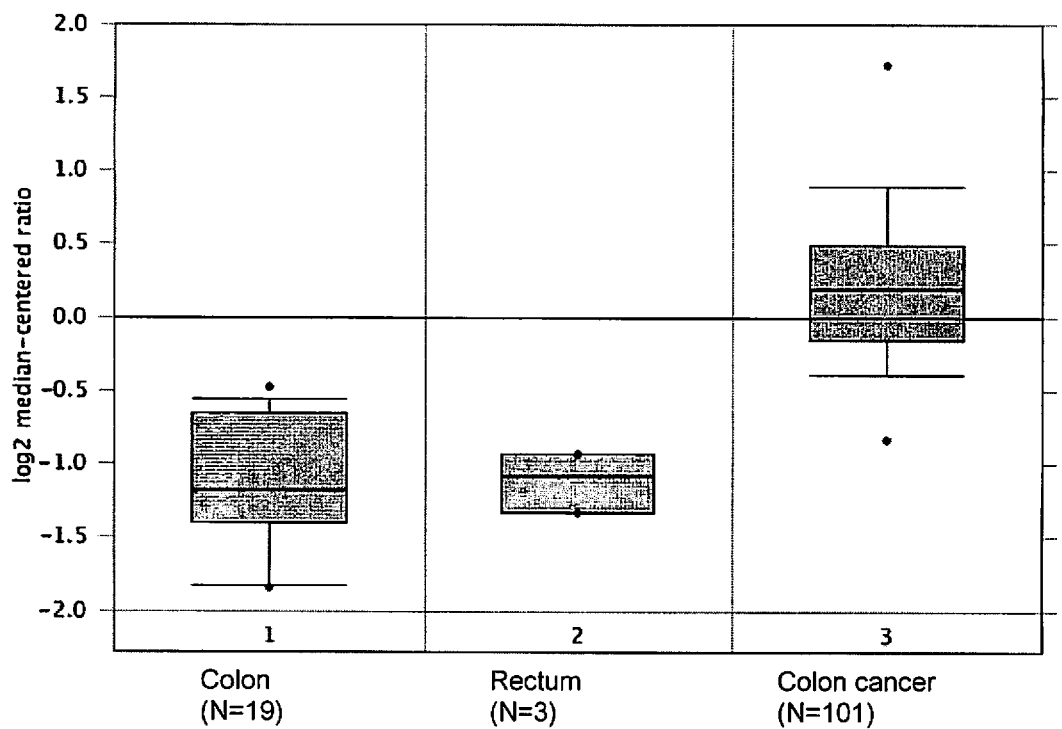
FIG. 16A-G: TFDP1 mRNA expression in TCGA and Protein Atlas database: (a) TFDP1 was upregulated in CRC compared with normal mucosa. (b) TFDP1 was upregulated in CRC in stage dependent manner. (c) The TFDP1 expression level was significantly higher in Stage III or IV CRC lesions relative to Stage I or II CRC lesions (P=0.01) in TCGA. (d) The TFDP1 expression level was also higher in lymph node metastasis-positive CRC lesions than in negative CRC lesions (P=0.01) in TCGA. (e) The TFDP1 expression level was also higher in distant metastasis-positive CRC lesions than in negative CRC lesions (P=0.04) in TCGA. (f) High TMCO3 group showed worse DFS (P=0.04) in TCGA. (g) The TFDP1 protein expression was significantly higher in CRCs compared with normal area in Protein Atlas database (P=0.04).
Figure 16A:
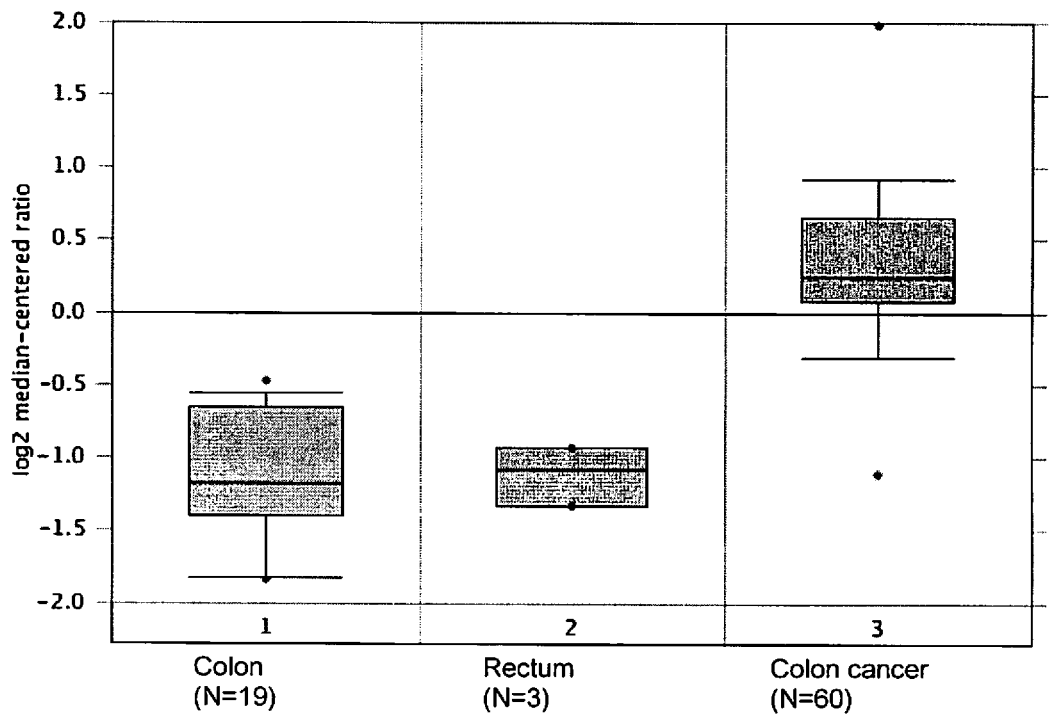
Figure 16B:
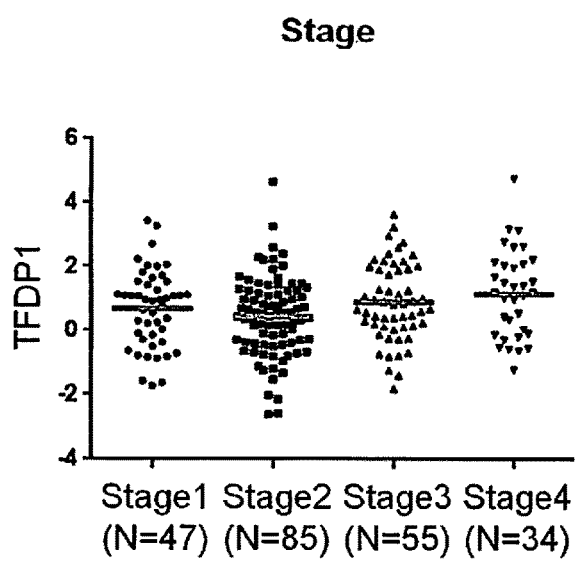
Figure 16C:
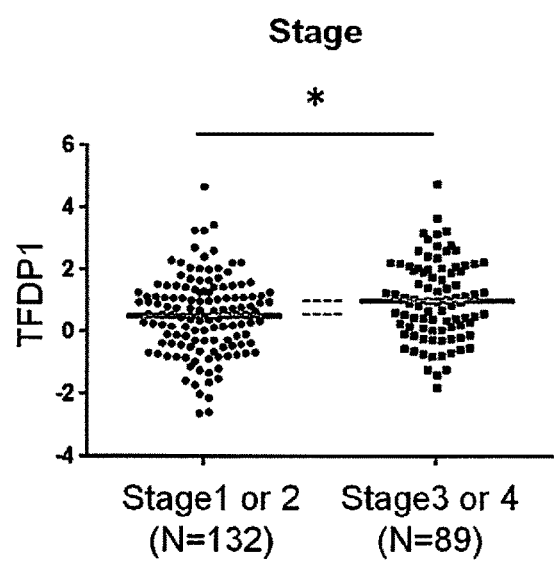
Figure 16D:
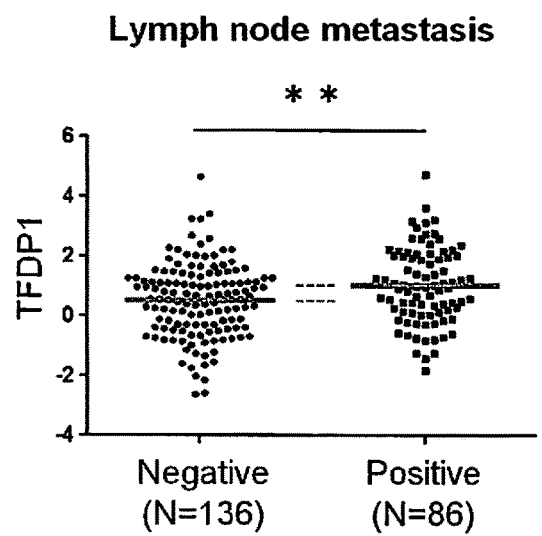
Figure 16E:
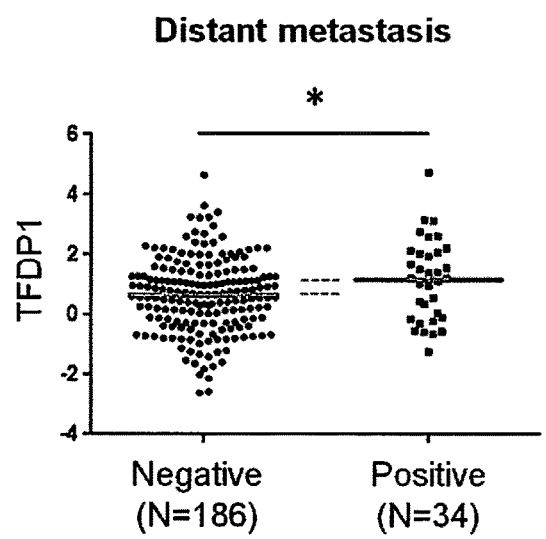
Figure 16F:
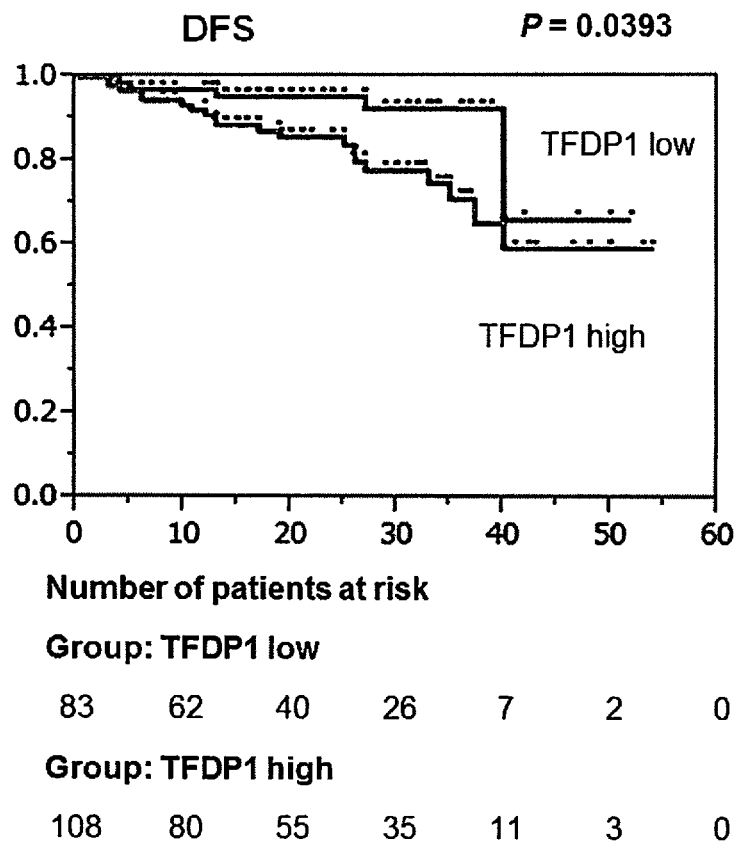
Figure 16G:
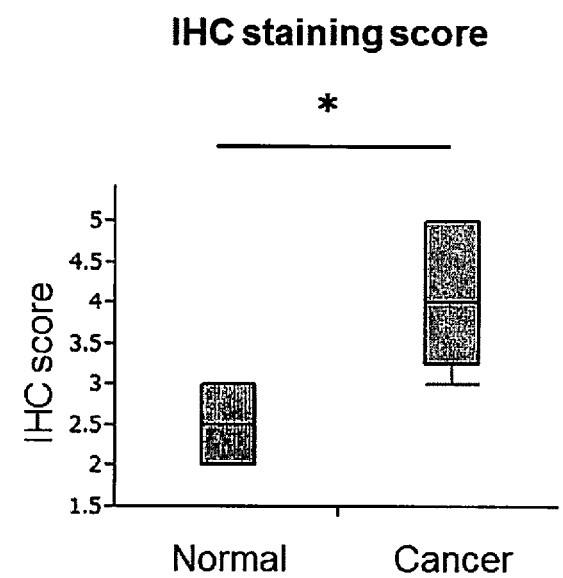

Finally, to clarify the target of the enhancer in TMCO3, the data of ChIA-PET was analysed using UCSC genome browser. The enhancer which was detected in FANTOM5 database was also detected in ChIA-PET data. Interestingly, this enhancer can activate promoter of TFDP1. TFDP1 is already reported as oncogenic transcription factor in cancer. Additionally, expression level in TCGA and Protein Atlas database was analyzed. TFDP1 was upregulated in CRCs and high TFDP1 group showed significant correlation with worse Stage (P=0.01), positive lymph node metastasis (P=0.01), positive distant metastasis (P=0.04) and worse DFS (P=0.04) (FIG. 16A-F). Additionally, TFDP1 protein was also upregulated in CRC (P=0.04) (FIG. 16G). Interestingly, the expression levels of TMCO3 and TFDP1 have a significant positive correlation in TCGA database (P<0.0001) (FIG. 13A). In the acidic environment in which TMCO3 is upregulated, TFDP1 is also upregulated (FIG. 13B). This means that enhancer of TMCO3 is activated in cancer cells and promote transcription of oncogenic TFDP1. Additionally, promoter of TMCO3 was hypo-methylated in CRCs compared with normal mucosa, suggesting that methylation of promoter in TMCO3 may also be a key regulator of TMCO3 expression (data not shown).

C. Discussion

In this study, it was at first planned to reveal cancer specific enhancer activation using FANTOM5 database. Inventors then selected the candidates which are in the lncRNA or protein coding gene upregulated in many types of cancer. Interestingly, TMCO3 enhancer has shown to be able to activate the promoter of oncogenic transcription factor, TFDP1 in the ChIA-PET of UCSC genome browser. Additionally, TMCO3 has the role as cation/proton anti transporter in homology analysis. Using these steps, the inventors selected TMCO3 and hypothesised that TMCO3 has a cancer specific enhancer activity which can activate oncogenic TFDP1 and play a key role to maintain ion homeostasis in cancer lesion. At first, the role of TMCO3 as cation/proton anti transporter was analyzed.

It was first demonstrated here that TMCO3 has oncogenic activities and has an important role in the maintenance of pH in cancer environment. When TMCO3 was knocked down, intracellular pH decreased in both SW480 and HCT116 CRC cells. Subsequently, proliferation, invasion, migration ability was suppressed and apoptosis was induced. On the other hand, TMCO3 is upregulated in acidic environment, suggesting that TMCO3 is required to pump out proton which is oversupplied by Warburg effect.

Next, TFDP1 was analysed, which was defined as the target of this enhancer in ChIA-PET. TFDP1 was upregulated in CRCs in Oncomine database. High expression of TFDP1 related to worse stage, positive distant metastasis and worse DFS in TCGA database. Additionally, expression level of TFDP1 was significantly correlated with that of TMCO3 in analysis of variance. TFDP1 protein was also upregulated in CRC in Protein Atlas database. In acidic culture in which TMCO3 was upregulated, TFDP1 was also upregulated, suggesting that this expression correlation is because of the related expression-control manner, maybe because of enhancer-promoter connection shown in ChIA-PET. In acidic environment cancer cell not only stimulate proton pomp-out system but also accelerate malignant potential by upregulation of TFDP1, in order to put up with this stressful environment and escape from there. In fact, acidic environment can promote metastatic potential by activation of matrix metalloproteinase, assisting the results.

Finally, the question about the relation between expression level of TMCO3 itself and its enhancer activity remains unclear. The relationship between enhancer derived RNA and target promoter can be explained by three patterns; (A) by directly recruiting a transcriptional activator or activator complex, (B) via mediating chromatin looping, (C) through evicting transcriptional repressors. Enhancer in TMCO3 has a connection to promoter of TFDP1 in ChIA-PET, suggesting that TMCO3 derived RNA may be able to activate TFDP1 promoter using the type B manner. Now the significance of enhancer derived RNA is discussed mainly in lnc RNA. However, protein coding genes also have enhancer, like TMCO3. These findings suggest that protein coding RNA may act as enhancer-derived RNA in the activation of target gene.

In conclusion, TMCO3 can play an oncogenic role in carcinogenesis using its oncogenic enhancer and the ability as intra-cellular pH regulator. TMCO3 may be a hopeful biomarker and target of treatment.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Akhtar-Zaidi B, Cowper-Sal-lari R, Corradin O, Saiakhova A, Bartels C F, Balasubramanian D, et al. Epigenomic enhancer profiling defines a signature of colon cancer. Science 2012; 336:736-9.

Andersson R, Gebhard C, Miguel-Escalada I, Hoof I, Bornholdt J, Boyd M, et al. An atlas of active enhancers across human cell types and tissues. Nature 2014; 507:455-61.

Aranda-Sicilia M N, Cagnac O, Chanroj S, Sze H, Rodriguez-Rosales M P, Venema K. *Arabidopsis* KEA2, a homolog of bacterial KefC, encodes a K(+)/H(+) antiporter with a chloroplast transit peptide. Biochimica et biophysica acta 2012; 1818:2362-71.

Aronson P S, Nee J, Suhm M A. Modifier role of internal H+ in activating the Na+-H+ exchanger in renal microvillus membrane vesicles. Nature 1982; 299:161-3.

Ausubel, *Current Protocols in Molecular Biology*, John Wiley & Sons, 1987-2006.

Banerji J, Rusconi S, Schaffner W. Expression of a beta-globin gene is enhanced by remote SV40 DNA sequences. Cell 1981; 27:299-308.

Bateman J R, Johnson J E, Locke M N. Comparing enhancer action in cis and in trans. Genetics 2012; 191:1143-55.

Berglund L, Bjorling E, Oksvold P, Fagerberg L, Asplund A, Szigyarto C A, et al. A genecentric Human Protein Atlas for expression profiles based on antibodies. Molecular & cellular proteomics: MCP 2008; 7:2019-27.

Biasini M, Bienert S, Waterhouse A, Arnold K, Studer G, Schmidt T, et al. SWISS-MODEL: modelling protein tertiary and quaternary structure using evolutionary information. Nucleic acids research 2014; 42:W252-8.

Blaveri E, Simko J P, Korkola J E, Brewer J L, Baehner F, Mehta K, et al. Bladder cancer outcome and subtype classification by gene expression. Clinical cancer research: an official journal of the American Association for Cancer Research 2005; 11:4044-55.

Booth I R, Epstein W, Giffard P M, Rowland G C. Roles of the Trkb and Trkc Gene-Products of *Escherichia-Coli* in K+-Transport. Biochimie 1985; 67:83-90.

Bourguignon L Y, Singleton P A, Diedrich F, Stern R, Gilad E. CD44 interaction with Na+-H+ exchanger (NHE1) creates acidic microenvironments leading to hyaluronidase-2 and cathepsin B activation and breast tumor cell invasion. The Journal of biological chemistry 2004; 279: 26991-7007.

Boussif et al., *Proc. Natl. Acad. Sci. USA*, 92(16):7297-7301, 1995.

Brett C L, Donowitz M, Rao R. Evolutionary origins of eukaryotic sodium/proton exchangers. American journal of physiology Cell physiology 2005; 288:C223-39.

Caley et al., *J. Virology*, 71(4):3031-3038, 1997.

Cardone R A, Casavola V, Reshkin S J. The role of disturbed pH dynamics and the Na+/H+ exchanger in metastasis. Nature reviews Cancer 2005; 5:786-95.

cBioPortal. http://www.cbioportal.org/index.do. Accessed in Dec. 1, 2014.

Cerami E, Gao J, Dogrusoz U, Gross B E, Sumer S O, Aksoy B A, et al. The cBio cancer genomics portal: an open platform for exploring multidimensional cancer genomics data. Cancer discovery 2012; 2:401-4.

Chanroj S, Wang G, Venema K, Zhang M W, Delwiche C F, Sze H. Conserved and diversified gene families of monovalent cation/h(+) antiporters from algae to flowering plants. Frontiers in plant science 2012; 3:25.

Chen and Okayama, Mol. Cell Biol., 7(8):2745-2752, 1987.

Cheng J H, Pan D Z, Tsai Z T, Tsai H K. Genome-wide analysis of enhancer RNA in gene regulation across 12 mouse tissues. Scientific reports 2015; 5:12648.

Coffin, In: *Virology*, Fields et al. (Eds.), Raven Press, N Y, 1437-1500, 1990.

Curtis C, Shah S P, Chin S F, Turashvili G, Rueda O M, Dunning M J, et al. The genomic and transcriptomic architecture of 2,000 breast tumours reveals novel subgroups. Nature 2012; 486:346-52.

Davis et al, *Curr. Biol.*, 6:146-148, 1996.

Derrien T, Guigo R. Long non-coding RNAs with enhancer-like function in human cells. M S-Med Sci 2011; 27:359-61.

FANTOM5. http://fantom.gsc.riken.jp/. Accessed in Jul. 1, 2014.

Fechheimer, et al., *Proc Natl. Acad. Sci. USA*, 84:8463-8467, 1987.

Fraley et al., *Proc. Natl. Acad. Sci. USA*, 76:3348-3352, 1979.

Gao J, Aksoy B A, Dogrusoz U, Dresdner G, Gross B, Sumer S O, et al. Integrative analysis of complex cancer genomics and clinical profiles using the cBioPortal. Science signaling 2013; 6:pl1.

Glorioso et al., *Mol. Biotechnol.*, 4(1):87-99, 1995.

Graham and Van Der Eb, *Virology*, 52:456-467, 1973.

Griffiths J R. Are cancer cells acidic? British journal of cancer 1991; 64:425-7.

Grunhaus and Horwitz, *Seminar in Virology*, 3:237-252, 1992.

Grutzmann R, Pilarsky C, Ammerpohl O, Luttges J, Bohme A, Sipos B, et al. Gene expression profiling of microdissected pancreatic ductal carcinomas using high-density DNA microarrays. Neoplasia 2004; 6:611-22.

Halama, et al., *Anticancer Res.* 28(6B):4111-5, 2008

Hao Y, Triadafilopoulos G, Sahbaie P, Young H S, Omary M B, Lowe A W. Gene expression profiling reveals stromal genes expressed in common between Barrett's esophagus and adenocarcinoma. Gastroenterology 2006; 131:925-33.

Harguindey S, Arranz J L, Wahl M L, Orive G, Reshkin S J. Proton transport inhibitors as potentially selective anticancer drugs. Anticancer research 2009; 29:2127-36.

Harguindey S, Orive G, Luis Pedraz J, Paradiso A, Reshkin S J. The role of pH dynamics and the Na+/H+ antiporter in the etiopathogenesis and treatment of cancer. Two faces of the same coin—one single nature. Biochimica et biophysica acta 2005; 1756:1-24.

Harland and Weintraub, J. Cell Biol., 101(3):1094-1099, 1985.

Herz H M, Hu D, Shilatifard A. Enhancer malfunction in cancer. Molecular cell 2014; 53:859-66.

Huang W Y, Hsu S D, Huang H Y, Sun Y M, Chou C H, Weng S L, et al. MethHC: a database of DNA methylation and gene expression in human cancer. Nucleic acids research 2015; 43:D856-61.

Jones J, Otu H, Spentzos D, Kolia S, Ivan M, Beecken W D, et al. Gene signatures of progression and metastasis in renal cell cancer. Clinical cancer research: an official journal of the American Association for Cancer Research 2005; 11:5730-9.

Kaiser S, Park Y K, Franklin J L, Halberg R B, Yu M, Jessen W J, et al. Transcriptional recapitulation and subversion of embryonic colon development by mouse colon tumor models and human colon cancer. Genome biology 2007; 8:R131.

Kato Y, Ozawa S, Miyamoto C, Maehata Y, Suzuki A, Maeda T, et al. Acidic extracellular microenvironment and cancer. Cancer cell international 2013; 13:89.

Kent W J, Sugnet C W, Furey T S, Roskin K M, Pringle T H, Zahler A M, et al. The human genome browser at UCSC. Genome research 2002; 12:996-1006.

Krogh A, Larsson B, von Heijne G, Sonnhammer E L. Predicting transmembrane protein topology with a hidden Markov model: application to complete genomes. Journal of molecular biology 2001; 305:567-80.

Lai F, Orom U A, Cesaroni M, Beringer M, Taatjes D J, Blobel G A, et al. Activating RNAs associate with Mediator to enhance chromatin architecture and transcription. Nature 2013; 494:497-501.

Lam M T, Li W, Rosenfeld M G, Glass C K. Enhancer RNAs and regulated transcriptional programs. Trends in biochemical sciences 2014; 39:170-82.

Laughlin et al., *J Virol.*, 60(2):515-524, 1986.

Lebkowski et al., *Mol. Cell. Biol.*, 8(10):3988-3996, 1988.

Lieberman, *Gastroenterology.* 142(2):194-6, 2012 Lusche D F, Wessels D, Ryerson D E, Soll D R. Nhel Is Essential for Potassium but Not Calcium Facilitation of Cell Motility and the Monovalent Cation Requirement for Chemotactic Orientation in Dictyostelium discoideum. Eukaryot Cell 2011; 10:320-31.

Ma X J, Dahiya S, Richardson E, Erlander M, Sgroi D C. Gene expression profiling of the tumor microenvironment during breast cancer progression. Breast cancer research: BCR 2009; 11:R7.

Martinez-Zaguilan R, Seftor E A, Seftor R E, Chu Y W, Gillies R J, Hendrix M J. Acidic pH enhances the invasive behavior of human melanoma cells. Clinical & experimental metastasis 1996; 14:176-86.

Masereel, et al., *Eur J Med Chem.* 38(6):547-54, 2003

McCarty et al., *J Virol.*, 65(6):2936-2945, 1991.

McLaughlin et al., *J. Virol.*, 62(6):1963-1973, 1988.

Meima M E, Webb B A, Witkowska H E, Barber D L. The sodium-hydrogen exchanger NHE1 is an Akt substrate necessary for actin filament reorganization by growth factors. The Journal of biological chemistry 2009; 284: 26666-75.

Melchor L, Saucedo-Cuevas L P, Munoz-Repeto I, Rodriguez-Pinilla S M, Honrado E, Campoverde A, et al. Comprehensive characterization of the DNA amplification at 13q34 in human breast cancer reveals TFDP1 and CUL4A as likely candidate target genes. Breast cancer research: BCR 2009; 11:R86.

Meropol, et al., *Oncologist.* 12(1):38-50, 2007

MethHC. http://MethHC.mbc.nctu.edu.tw. Accessed in Jul. 1, 2015.

Moller S, Croning M D, Apweiler R. Evaluation of methods for the prediction of membrane spanning regions. Bioinformatics 2001; 17:646-53.

Muzyczka, *Curr. Topics Microbiol. Immunol.*, 158:97-129, 1992.

Nakamura N, Tanaka S, Teko Y, Mitsui K, Kanazawa H. Four Na+/H+ exchanger isoforms are distributed to Golgi and post-Golgi compartments and are involved in organelle pH regulation. The Journal of biological chemistry 2005; 280:1561-72.

Nicolau and Sene, *Biochim. Biophys. Acta*, 721:185-190, 1982.

Nikou et al., *Hepatogastroenterology*, 52:731-741, 2005.

Nindl I, Dang C, Forschner T, Kuban R J, Meyer T, Sterry W, et al. Identification of differentially expressed genes in cutaneous squamous cell carcinoma by microarray expression profiling. Molecular cancer 2006; 5:30.

Oncomine_database. https://www.oncomine.org/. Accessed in Jun. 1, 2015.

Orom U A, Derrien T, Guigo R, Shiekhattar R. Long noncoding RNAs as enhancers of gene expression. Cold Spring Harbor symposia on quantitative biology 2010; 75:325-31.

Orom U A, Shiekhattar R. Long non-coding RNAs and enhancers. Current opinion in genetics & development 2011; 21:194-8.

Orom U A, Shiekhattar R. Long Noncoding RNAs Usher In a New Era in the Biology of Enhancers. Cell 2013; 154:1190-3.

Orom U A, Shiekhattar R. Noncoding RNAs and enhancers: complications of a long-distance relationship. Trends in Genetics 2011; 27:433-9.

Piccaluga P P, Agostinelli C, Califano A, Rossi M, Basso K, Zupo S, et al. Gene expression analysis of peripheral T cell lymphoma, unspecified, reveals distinct profiles and new potential therapeutic targets. The Journal of clinical investigation 2007; 117:823-34.

Ponten F, Jirstrom K, Uhlen M. The Human Protein Atlas—a tool for pathology. The Journal of pathology 2008; 216: 387-93.

Potter et al., *Proc. Natl. Acad. Sci. USA*, 81:7161-7165, 1984.

Ramzy, *Ibrahim Clinical Cytopathology and Aspiration Biopsy*, McGraw Hill Professional, 2001

Remington's Pharmaceutical Sciences, 18th Ed. Mack Printing Company, 1990, pp. 1289-1329

Reshkin S J, Bellizzi A, Caldeira S, Albarani V, Malanchi I, Poignee M, et al. Na+/H+ exchanger-dependent intracellular alkalinization is an early event in malignant transformation and plays an essential role in the development of subsequent transformation-associated phenotypes. FASEB journal: official publication of the Federation of American Societies for Experimental Biology 2000; 14:2185-97.

Reshkin S J, Cardone R A, Harguindey S. Na+-H+ exchanger, pH regulation and cancer.

Recent patents on anti-cancer drug discovery 2013; 8:85-99.

Reshkin, et al., *Recent Pat Anticancer Drug Discov.* 8(1): 85-99, 2013

Riker A I, Enkemann S A, Fodstad O, Liu S, Ren S, Morris C, et al. The gene expression profiles of primary and metastatic melanoma yields a transition point of tumor progression and metastasis. BMC medical genomics 2008; 1:13.

Rippe, et al., *Mol. Cell Biol.*, 10:689-695, 1990.

Roessler S, Jia H L, Budhu A, Forgues M, Ye Q H, Lee J S, et al. A unique metastasis gene signature enables prediction of tumor relapse in early-stage hepatocellular carcinoma patients. Cancer research 2010; 70:10202-12.

Roux et al., *Proc. Natl. Acad. Sci. USA*, 86:9079-9083, 1989.

SACS_TMHMM_Transmembrane_Prediction. http://www.sacs.ucsfedu/cgi-bin/tmhmm.py. Accessed in Oct. 1, 2014.

Saier M H, Jr. A functional-phylogenetic classification system for transmembrane solute transporters. Microbiology and molecular biology reviews: MA/MR 2000; 64:354-411.

Sambrook and Russell, Molecular Cloning: A Laboratory Manual 3$^{rd}$ Ed., Cold Spring Harbor Laboratory Press, 2001.

Sambrook and Russell, Molecular Cloning: A Laboratory Manual, 3rd Edition, 2000.

Samulski et al., *J. Virol.*, 63:3822-3828, 1989.

Sanchez-Carbayo M, Socci N D, Lozano J, Saint F, Cordon-Cardo C. Defining molecular profiles of poor outcome in patients with invasive bladder cancer using oligonucleotide microarrays. Journal of clinical oncology: official journal of the American Society of Clinical Oncology 2006; 24:778-89.

Sardet C, Franchi A, Pouyssegur J. Molecular cloning, primary structure, and expression of the human growth factor-activatable Na+/H+ antiporter. Cell 1989; 56:271-80.

Siegel, et al., *Cancer Epidemiol Biomarkers Prev.* 21(3): 411-6, 2012.

Skrzypczak M, Goryca K, Rubel T, Paziewska A, Mikula M, Jarosz D, et al. Modeling oncogenic signaling in colon tumors by multidirectional analyses of microarray data directed for maximization of analytical reliability. PloS one 2010; 5.

SWISS-MODEL. http://swissmodel.expasy.org/. Accessed in Oct. 1, 2014.

Talantov D, Mazumder A, Yu J X, Briggs T, Jiang Y, Backus J, et al. Novel genes associated with malignant melanoma but not benign melanocytic lesions. Clinical cancer research: an official journal of the American Association for Cancer Research 2005; 11:7234-42.

TCGA_Research_Network. http://cancergenome.nih.gov/. Accessed in Oct. 1, 2014.

TFBIND. http://tfbind.hgc.jp/. Accessed in Jun. 1, 2015.

The_Human_Protein_Atlas. www.proteinatlas.org. Accessed in Jun. 1, 2015.

Toden S, Okugawa Y, Buhrmann C, Nattamai D, Anguiano E, Baldwin N, et al. Novel Evidence for Curcumin and Boswellic Acid-Induced Chemoprevention through Regulation of miR-34a and miR-27a in Colorectal Cancer. Cancer Prev Res (Phila) 2015; 8:431-43.

Tratschin et al., *Mol. Cell. Biol.*, 4:2072-2081, 1984.

Trompeter et al, *J. Immunol. Methods,* 274(1-2):245-56, 2003.

Tur-Kaspa et al., *Mol. Cell Biol.*, 6:716-718, 1986.

UCSC_Genome_Browser. http://genome.ucsc.edu/. Accessed in Jun. 1, 2015.

Uhlen M, Bjorling E, Agaton C, Szigyarto C A, Amini B, Andersen E, et al. A human protein atlas for normal and cancer tissues based on antibody proteomics. Molecular & cellular proteomics: MCP 2005; 4:1920-32.

Uhlen M, Fagerberg L, Hallstrom B M, Lindskog C, Oksvold P, Mardinoglu A, et al. Proteomics. Tissue-based map of the human proteome. Science 2015; 347:1260419.

Uhlen M, Oksvold P, Fagerberg L, Lundberg E, Jonasson K, Forsberg M, et al. Towards a knowledge-based Human Protein Atlas. Nature biotechnology 2010; 28:1248-50.

Valk P J, Verhaak R G, Beijen M A, Erpelinck C A, Barjesteh van Waalwijk van Doorn-Khosrovani S, Boer J M, et al. Prognostically useful gene-expression profiles in acute myeloid leukemia. The New England journal of medicine 2004; 350:1617-28.

Vaupel P, Okunieff P, Neuringer L J. Blood flow, tissue oxygenation, pH distribution, and energy metabolism of murine mammary adenocarcinomas during growth. Advances in experimental medicine and biology 1989; 248:835-45.

Vucicevic D, Corradin O, Ntini E, Scacheri P C, Orom U A. Long ncRNA expression associates with tissue-specific enhancers. Cell Cycle 2015; 14:253-60.

Wallace T A, Prueitt R L, Yi M, Howe T M, Gillespie J W, Yfantis H G, et al. Tumor immunobiological differences in prostate cancer between African-American and European-American men. Cancer research 2008; 68:927-36.

Wang D, Russell J, Xu H, Johnson D G. Deregulated expression of DP1 induces epidermal proliferation and enhances skin carcinogenesis. Molecular carcinogenesis 2001; 31:90-100.

Warburg O. On respiratory impairment in cancer cells. Science 1956; 124:269-70.

Wu and Wu, *Biochemistry,* 27: 887-892, 1988.

Wu and Wu, *J. Biol. Chem.*, 262:4429-4432, 1987.

Yang and Russell, *Proc. Natl. Acad. Sci. USA,* 87:4144-4148, 1990.

Yasui K, Arii S, Zhao C, Imoto I, Ueda M, Nagai H, et al. TFDP1, CUL4A, and CDC16 identified as targets for amplification at 13q34 in hepatocellular carcinomas. Hepatology 2002; 35:1476-84.

Yasui K, Okamoto H, Arii S, Inazawa J. Association of over-expressed TFDP1 with progression of hepatocellular carcinomas. Journal of human genetics 2003; 48:609-13.

Yusenko M V, Kuiper R P, Boethe T, Ljungberg B, van Kessel A G, Kovacs G. High-resolution DNA copy number and gene expression analyses distinguish chromophobe renal cell carcinomas and renal oncocytomas. BMC cancer 2009; 9:152.

---

The invention claimed is:

1. A method of treating an advanced colorectal cancer in a patient determined to have an elevated TMCO3 expression level in a biological sample from the patient as compared to a biological sample from a patient with early colorectal cancer, the method comprising treating the patient with a TMCO3 inhibitor or with adjuvant therapy.

2. The method of claim 1, wherein treating the patient with the adjuvant therapy or TMCO3 inhibitor comprises providing to the patient a pharmaceutical composition comprising an advanced colorectal cancer treatment, wherein the pharmaceutical composition further comprises a lipid component.

3. The method of claim 1, wherein the advanced colorectal cancer comprises one or more of category T3 or T4 colorectal cancer; lymph node metastasis; N1 and/or N2 colorectal cancer; distant metastasis; distant liver metastasis; and M1 colorectal cancer.

4. The method of claim 1, wherein the advanced colorectal cancer comprises Stage and/or Stage IV colorectal cancer.

5. The method of claim 1, wherein the method comprises treating the patient with adjuvant therapy and wherein the adjuvant therapy comprises one or more of cetuximab, fluorouracil, oxaliplatin, irinotecan, bevacizumab, panitumumab, afibercept, leucovorin, capecitabine, and radiotherapy.

6. The method of claim 1, wherein the method further comprises surgical removal of one or more secondary tumors.

7. The method of claim 1, wherein the method comprises treating the patient with an effective amount of a TMCO3 inhibitor.

8. The method of claim 7, wherein the TMCO3 inhibitor is an isolated nucleic acid molecule that hybridizes with a nucleic acid molecule encoding TMCO3.

9. The method of claim 8, wherein the TMCO3 inhibitor is an siRNA, a double stranded RNA, a short hairpin RNA, or an antisense oligonucleotide.

10. The method of claim 9 wherein the TMCO3 inhibitor is an siRNA.

11. The method of claim 7, wherein the TMCO3 inhibitor is an antibody that binds to a TMCO3 protein and inhibits the activity of TMCO3.

12. The method of claim 7, wherein the TMCO3 inhibitor is a small molecule compound.

13. The method of claim 1, wherein the biological sample from the patient and the biological sample from the patient with early colorectal cancer each comprise a tissue sample comprising colorectal cancer cells.

14. A method of treating Stage II colorectal cancer in a patient determined to have colorectal cancer cells with elevated TMCO3 expression level as compared to colorectal cancer cells from a patient having Stage I colorectal cancer, the method comprising administering a therapy to the patient, wherein the therapy comprises cetuximab, fluorouracil, oxaliplatin, irinotecan, bevacizumab, panitumumab, afibercept, leucovorin, capecitabine, radiotherapy, or a combination thereof.

15. The method of claim 14, wherein the method further comprises providing a TMCO3 inhibitor.

16. The method of claim 5, wherein the adjuvant therapy comprises fluorouracil, leucovorin, and oxaliplatin.

17. The method of claim 5, wherein the adjuvant therapy comprises capecitabine and oxaliplatin.

18. The method of claim 14, wherein the therapy comprises fluorouracil, leucovorin, and oxaliplatin.

19. The method of claim 14, wherein the therapy comprises capecitabine and oxaliplatin.

* * * * *

SEQUENCE LISTING

```
<160> NUMBER OF SEQ ID NOS: 16

<210> SEQ ID NO 1
<211> LENGTH: 3102
<212> TYPE: DNA
<213> ORGANISM: Artificial Sequence
<220> FEATURE:
<223> OTHER INFORMATION: Synthetic Primer

<400> SEQUENCE: 1 ttaaagggggg cagtgactgc ggctgggcgg gagtccgggt cggcttggct gagcggggggc      60 ggtgctgggc agggcggcgg ccgctccctc ccggactccc ggcctcccgg cctccctggt     120
cccgcctggg aagggatgca aggaagccct ccggcgctgc gctccgaggc gggagacagc     180
```

```
gtcccctcc gccctcggg tcctggcgcc tcagagcccg gcccaggccg cggaacggtg      240
atgctcgggc cggacgggcg ggcgcggatc cctgcgtccc gctgaaaatg tgtgtctgac      300
atgcaagctc agtggggcag agaccgtggg attgctgtgc cctgccctcc ggacctggat      360
catgaaggtt ttgggaagaa gcttcttctg ggtgctgttt cccgtccttc cctgggcggt      420
gcaggctgtg gagcacgagg aggtggcgca gcgtgtgatc aaactgcacc gcgggcgagg      480
ggtggctgcc atgcagagcc ggcagtgggt ccgggacagc tgcaggaagc tctcagggct      540
tctccgccag aagaatgcag ttctgaacaa actgaaaact gcaattggag cagtggagaa      600
agacgtgggc ctgtcggatg aagagaaact gtttcaggtg cacacgtttg aaattttcca      660
gaaagagctg aatgaaagtg aaaattccgt tttccaagct gtctacggac tgcagagagc      720
cctgcagggg gattacaaag atgtcgtgaa catgaaggag agcagccggc agcgcctgga      780
ggccctgaga gaggctgcaa taaaggaaga aacagaatat atggaacttc tggcagcaga      840
aaaacatcaa gttgaagccc ttaaaaatat gcaacatcaa aaccaaagtt tatccatgct      900
tgacgagatt cttgaagatg taagaaaggc agcggatcgt ctggaggaag agatagagga      960
acatgctttt gacgacaata aatcagtcaa gggggtcaat tttgaggcag ttctgagggt     1020
ggaggaagaa gaggccaatt ctaagcaaaa tataacaaaa cgagaagtgg aggatgactt     1080
gggtcttagc atgctgattg actcccagaa caaccagtat attttgacca gcccagaga     1140 ttcaaccatc ccacgtgcag atcaccactt tataaaggac attgttacca taggaatgct     1200
gtccttgcct tgtggctggc tatgtacagc cataggattg cctacaatgt ttggttatat     1260
tatttgtggt gtacttctgg gaccttcagg actaaatagt attaagtcta ttgtgcaagt     1320
ggagacatta ggagaatttg gggtgttttt tactcttttt cttgttggct tagaattttc     1380
tccagaaaag ctaagaaagg tgtggaagat ttccttacaa gggccgtgtt acatgacact     1440
gttaatgatt gcatttggct tgctgtgggg gcatctcttg cggatcaaac ccacgcagag     1500
cgtcttcatt tccacgtgtc tgtccttgtc aagcacaccc ctcgtgtcca ggttcctcat     1560
gggcagtgct cggggtgaca agaaggcga cattgactac agcaccgtgc tcctcggcat     1620
gctggtgacg caggacgtgc agctcgggct cttcatggcc gtcatgccga ctctcataca     1680
ggcgggcgcc agtgcatctt ctagcattgt cgtggaagtt ctccgaatcc tggttttgat     1740
tggtcagatt cttttttcac tagcggcggt ttttctttta tgtcttgtta taagaagta     1800 tctcattgga ccctattatc ggaagctgca catggaaagc aaggggaaca agaaatcct     1860 gatcttggga atatctgcct ttatcttctt aatgttaacg gtcacggagc tgctggacgt     1920
ctccatggag ctgggctgtt tcctggctgg agcgctcgtc tcctcagg gccccgtggt     1980 caccgaggag atcgccacct ccatcgaacc catccgcgac ttcctggcca tcgttttctt     2040
cgcctccata gggctccacg tgttccccac gtttgtggcg tacgagctca cggtgctggt     2100
gttcctcacc ttgtcagtgg tggtgatgaa gtttctcctg cgcgcgctgg tcctgtctct     2160
cattctgccg aggagcagcc agtacatcaa gtggatcgtc tctgcggggc ttgcccaggt     2220
cagcgagttt tcctttgtcc tggggagccg ggcgcgaaga gcgggcgtca tctctcggga     2280
ggtgtacctc cttatactga gtgtgaccac gctcagcctc ttgctcgccc ggtgctgtg      2340 gagagctgca atcacgaggt gtgtgcccag accggagaga cggtccagcc tctgatggct     2400
cggagatgat ggaccgtgga agggaagcgt ctgtggggag tgagcgctta gatggccagc     2460
agctgctcct tctgggaagc tcgcaccttg gcaacagaac agccctctag cagagcgtca     2520
gtgcagtcgt gttatcccgg cttttacaga atattcttgt cctattttag aatttttccgg     2580
```

```
agtagtttat ttgcagtctg ttgattatgt gcagtagacc cgggacactg cgttttaccg    2640
atcaccttga atgtggtgcc tggatgtgcc ttttttttt ttccctgaaa ttattattaa    2700
ttttctattg tgagttcatc agttcatagt ttttttagta aagaagcaaa attaaaaggc    2760
ttttaaaaat gtacaacttc agaattataa tctgttagtc aaatatttgt tattaaacat    2820
ttctgtaata tgaagttgta atcctggccg tgagcttgga agcttacttt tgattcttaa    2880
agcctatgtt ttctaaaatg agacaaatac ggatgtctat ttgccttta ttgtaacttt    2940 taaatgaaat aatttcatgt caatttctat tagatatatc acttaaaata tttggtttta    3000
aatcacaaga atatgtattc tttaataaag ataatttatg atcatggtat aattaattga    3060
aatttattaa aatctgtttt tattaaaaaa aaaaaaaaaa aa                       3102
```

<210> SEQ ID NO 2
<211> LENGTH: 677
<212> TYPE: PRT
<213> ORGANISM: Artificial Sequence
<220> FEATURE:
<223> OTHER INFORMATION: Synthetic Peptide

<400> SEQUENCE: 2

```
Met Lys Val Leu Gly Arg Ser Phe Phe Trp Val Leu Phe Pro Val Leu
1               5                   10                  15

Pro Trp Ala Val Gln Ala Val Glu His Glu Glu Val Ala Gln Arg Val
            20                  25                  30

Ile Lys Leu His Arg Gly Arg Gly Val Ala Ala Met Gln Ser Arg Gln
        35                  40                  45

Trp Val Arg Asp Ser Cys Arg Lys Leu Ser Gly Leu Leu Arg Gln Lys
    50                  55                  60

Asn Ala Val Leu Asn Lys Leu Lys Thr Ala Ile Gly Ala Val Glu Lys
65                  70                  75                  80

Asp Val Gly Leu Ser Asp Glu Glu Lys Leu Phe Gln Val His Thr Phe
                85                  90                  95

Glu Ile Phe Gln Lys Glu Leu Asn Glu Ser Glu Asn Ser Val Phe Gln
            100                 105                 110

Ala Val Tyr Gly Leu Gln Arg Ala Leu Gln Gly Asp Tyr Lys Asp Val
        115                 120                 125

Val Asn Met Lys Glu Ser Ser Arg Gln Arg Leu Glu Ala Leu Arg Glu
    130                 135                 140

Ala Ala Ile Lys Glu Glu Thr Glu Tyr Met Glu Leu Leu Ala Ala Glu
145                 150                 155                 160

Lys His Gln Val Glu Ala Leu Lys Asn Met Gln His Gln Asn Gln Ser
                165                 170                 175

Leu Ser Met Leu Asp Glu Ile Leu Glu Asp Val Arg Lys Ala Ala Asp
            180                 185                 190

Arg Leu Glu Glu Glu Ile Glu Glu His Ala Phe Asp Asp Asn Lys Ser
        195                 200                 205

Val Lys Gly Val Asn Phe Glu Ala Val Leu Arg Val Glu Glu Glu Glu
    210                 215                 220

Ala Asn Ser Lys Gln Asn Ile Thr Lys Arg Glu Val Glu Asp Asp Leu
225                 230                 235                 240

Gly Leu Ser Met Leu Ile Asp Ser Gln Asn Asn Gln Tyr Ile Leu Thr
                245                 250                 255

Lys Pro Arg Asp Ser Thr Ile Pro Arg Ala Asp His His Phe Ile Lys
            260                 265                 270
```

```
Asp Ile Val Thr Ile Gly Met Leu Ser Leu Pro Cys Gly Trp Leu Cys
            275                 280                 285

Thr Ala Ile Gly Leu Pro Thr Met Phe Gly Tyr Ile Ile Cys Gly Val
        290                 295                 300

Leu Leu Gly Pro Ser Gly Leu Asn Ser Ile Lys Ser Ile Val Gln Val
305                 310                 315                 320

Glu Thr Leu Gly Glu Phe Gly Val Phe Phe Thr Leu Phe Leu Val Gly
                325                 330                 335

Leu Glu Phe Ser Pro Glu Lys Leu Arg Lys Val Trp Lys Ile Ser Leu
            340                 345                 350

Gln Gly Pro Cys Tyr Met Thr Leu Leu Met Ile Ala Phe Gly Leu Leu
        355                 360                 365

Trp Gly His Leu Leu Arg Ile Lys Pro Thr Gln Ser Val Phe Ile Ser
    370                 375                 380

Thr Cys Leu Ser Leu Ser Ser Thr Pro Leu Val Ser Arg Phe Leu Met
385                 390                 395                 400

Gly Ser Ala Arg Gly Asp Lys Glu Gly Asp Ile Asp Tyr Ser Thr Val
                405                 410                 415

Leu Leu Gly Met Leu Val Thr Gln Asp Val Gln Leu Gly Leu Phe Met
            420                 425                 430

Ala Val Met Pro Thr Leu Ile Gln Ala Gly Ala Ser Ala Ser Ser Ser
        435                 440                 445

Ile Val Val Glu Val Leu Arg Ile Leu Val Leu Ile Gly Gln Ile Leu
    450                 455                 460

Phe Ser Leu Ala Ala Val Phe Leu Leu Cys Leu Val Ile Lys Lys Tyr
465                 470                 475                 480

Leu Ile Gly Pro Tyr Tyr Arg Lys Leu His Met Glu Ser Lys Gly Asn
                485                 490                 495

Lys Glu Ile Leu Ile Leu Gly Ile Ser Ala Phe Ile Phe Leu Met Leu
            500                 505                 510

Thr Val Thr Glu Leu Leu Asp Val Ser Met Glu Leu Gly Cys Phe Leu
        515                 520                 525

Ala Gly Ala Leu Val Ser Ser Gln Gly Pro Val Val Thr Glu Glu Ile
    530                 535                 540

Ala Thr Ser Ile Glu Pro Ile Arg Asp Phe Leu Ala Ile Val Phe Phe
545                 550                 555                 560

Ala Ser Ile Gly Leu His Val Phe Pro Thr Phe Val Ala Tyr Glu Leu
                565                 570                 575

Thr Val Leu Val Phe Leu Thr Leu Ser Val Val Met Lys Phe Leu
            580                 585                 590

Leu Ala Ala Leu Val Leu Ser Leu Ile Leu Pro Arg Ser Ser Gln Tyr
        595                 600                 605

Ile Lys Trp Ile Val Ser Ala Gly Leu Ala Gln Val Ser Glu Phe Ser
    610                 615                 620

Phe Val Leu Gly Ser Arg Ala Arg Arg Ala Gly Val Ile Ser Arg Glu
625                 630                 635                 640

Val Tyr Leu Leu Ile Leu Ser Val Thr Thr Leu Ser Leu Leu Leu Ala
                645                 650                 655

Pro Val Leu Trp Arg Ala Ala Ile Thr Arg Cys Val Pro Arg Pro Glu
            660                 665                 670

Arg Arg Ser Ser Leu
            675
```

```
<210> SEQ ID NO 3
<211> LENGTH: 21
<212> TYPE: DNA
<213> ORGANISM: Artificial Sequence
<220> FEATURE:
<223> OTHER INFORMATION: Synthetic Primer

<400> SEQUENCE: 3
ctgagtccga atcaggtgca g                                      21

<210> SEQ ID NO 4
<211> LENGTH: 21
<212> TYPE: DNA
<213> ORGANISM: Artificial Sequence
<220> FEATURE:
<223> OTHER INFORMATION: Synthetic Primer

<400> SEQUENCE: 4
atccatgggg agatgttctg g                                      21

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
gccgaaacaa gaagaaggag a                                      21

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
tcgttcttga gctcctcaat c                                      21

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
gttctccagc gacaaggcta                                        20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
atcctgcttg ctgttgttgg                                        20

<210> SEQ ID NO 9
<211> LENGTH: 22
<212> TYPE: DNA
<213> ORGANISM: Artificial Sequence
<220> FEATURE:
<223> OTHER INFORMATION: Synthetic Primer
```

-continued

<400> SEQUENCE: 9
agaaccagga aacggaaaca ga                                              22

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
tctccttcat gcgctgcttt                                                 20

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11 acaccccag cactcactttt                                                 20

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
ggcccttgcc attcttctct                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
ctgcaccacc aactgcttag                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
gtcttctggg tggcagtgat                                                 20

<210> SEQ ID NO 15
<211> LENGTH: 19
<212> TYPE: DNA
<213> ORGANISM: Artificial Sequence
<220> FEATURE:
<223> OTHER INFORMATION: Synthetic Primer

<400> SEQUENCE: 15
gaggcccacg ttctaacct                                                  19

<210> SEQ ID NO 16

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
cgttaggagt cacaggaggg                                                    20
```